(12) United States Patent
Gardella et al.

(10) Patent No.: US 7,795,220 B2
(45) Date of Patent: Sep. 14, 2010

(54) CONFORMATIONALLY CONSTRAINED PARATHYROID HORMONES WITH ALPHA-HELIX STABILIZERS

(75) Inventors: Thomas J. Gardella, Needham, MA (US); John T. Potts, Jr., Charlestown, MA (US); Henry M. Kronenberg, Boston, MA (US); Naoto Shimizu, Shizuoka (JP)

(73) Assignees: The General Hospital Corporation, Boston, MA (US); Bristol-Myers Squibb Company, Princeton, NJ (US)

( * ) Notice: Subject to any disclaimer, the term of this patent is extended or adjusted under 35 U.S.C. 154(b) by 879 days.

(21) Appl. No.: 10/549,592

(22) PCT Filed: Mar. 19, 2003

(86) PCT No.: PCT/US03/08261

§ 371 (c)(1),
(2), (4) Date: Jan. 12, 2007

(87) PCT Pub. No.: WO2004/093902

PCT Pub. Date: Nov. 4, 2004

(65) Prior Publication Data

US 2007/0161569 A1    Jul. 12, 2007

(51) Int. Cl.
*A61K 38/10* (2006.01)
(52) U.S. Cl. .......................................... 514/14; 530/326
(58) Field of Classification Search ........................ None
See application file for complete search history.

(56) References Cited

U.S. PATENT DOCUMENTS

| | | | |
|---|---|---|---|
| 4,086,196 A | 4/1978 | Tregear | |
| 4,366,241 A | 12/1982 | Tom et al. | |
| 4,423,037 A | 12/1983 | Rosenblatt et al. | |
| 4,511,502 A | 4/1985 | Builder et al. | |
| 4,512,922 A | 4/1985 | Jones et al. | |
| 4,518,526 A | 5/1985 | Olson | |
| 4,620,948 A | 11/1986 | Builder et al. | |
| 4,675,189 A | 6/1987 | Kent et al. | |
| 4,698,328 A | 10/1987 | Neer et al. | |
| 4,736,866 A | 4/1988 | Leder et al. | |
| 4,761,406 A | 8/1988 | Flora et al. | |
| 4,843,000 A | 6/1989 | Litman et al. | |
| 4,849,338 A | 7/1989 | Litman et al. | |
| 5,010,010 A | 4/1991 | Gautvik et al. | |
| 5,208,041 A | 5/1993 | Sindrey | |
| 5,217,896 A | 6/1993 | Kramer et al. | |
| 5,227,487 A | 7/1993 | Haugland et al. | |
| 5,274,113 A | 12/1993 | Kang et al. | |
| 5,326,692 A | 7/1994 | Brinkley et al. | |
| 5,350,836 A | 9/1994 | Kopchick et al. | |
| 5,382,658 A | 1/1995 | Kronis et al. | |
| 5,393,869 A | 2/1995 | Nakagawa et al. | |
| 5,405,975 A | 4/1995 | Kuhn et al. | |
| 5,433,896 A | 7/1995 | Kang et al. | |
| 5,442,045 A | 8/1995 | Haugland et al. | |
| 5,451,663 A | 9/1995 | Kang et al. | |
| 5,453,517 A | 9/1995 | Kuhn et al. | |
| 5,457,034 A | 10/1995 | della Valle et al. | |
| 5,459,276 A | 10/1995 | Kuhn et al. | |
| 5,462,856 A | 10/1995 | Lerner et al. | |
| 5,494,806 A | 2/1996 | Segre et al. | |
| 5,496,801 A | 3/1996 | Holthuis et al. | |
| 5,501,979 A | 3/1996 | Geller et al. | |
| 5,516,864 A | 5/1996 | Kuhn et al. | |
| 5,527,772 A | 6/1996 | Holick | |
| 5,556,940 A | 9/1996 | Willick et al. | |
| 5,573,909 A | 11/1996 | Singer et al. | |
| 5,578,461 A | 11/1996 | Sherwin et al. | |
| 5,589,452 A | 12/1996 | Krstenansky et al. | |
| 5,605,815 A | 2/1997 | Broadus et al. | |
| 5,616,560 A | 4/1997 | Geddes et al. | |
| 5,648,270 A | 7/1997 | Kuhn et al. | |
| 5,656,465 A | 8/1997 | Panicali et al. | |
| 5,693,616 A | 12/1997 | Krstenansky et al. | |
| 5,695,955 A | 12/1997 | Krstenansky et al. | |
| 5,717,062 A | 2/1998 | Chorev et al. | |
| 5,723,218 A | 3/1998 | Haugland et al. | |
| 5,723,577 A | 3/1998 | Dong | |

(Continued)

FOREIGN PATENT DOCUMENTS

AU    668118    4/1996

(Continued)

OTHER PUBLICATIONS

Shimizu et al., J. of Bio. Chem., 2001, vol. 278, pp. 49003-49012.*

(Continued)

*Primary Examiner*—Christopher R. Tate
*Assistant Examiner*—Roy Teller
(74) *Attorney, Agent, or Firm*—Clark & Elbing LLP

(57) ABSTRACT

The present invention relates to conformationally constrained parathyroid hormone (PTH) analogs and derivatives of those analogs. The invention also provides methods of preparing and using the PTH analogs. Further, the invention encompasses compositions and methods for use in limiting undesired bone loss in a vertebrate at risk of such bone loss, in treating conditions that are characterized by undesired bone loss or by the need for bone growth, e.g. in treating fractures or cartilage disorders and for raising camp levels in cells where deemed necessary.

29 Claims, 9 Drawing Sheets

U.S. PATENT DOCUMENTS

| | | | |
|---|---|---|---|
| 5,741,486 A | 4/1998 | Pathak et al. | |
| 5,763,416 A | 6/1998 | Bonadio et al. | |
| 5,798,225 A | 8/1998 | Krstenansky et al. | |
| 5,807,823 A | 9/1998 | Krstenansky et al. | |
| 5,814,603 A | 9/1998 | Oldenburg et al. | |
| 5,821,225 A | 10/1998 | Vickery | |
| 5,836,905 A | 11/1998 | Lemelson et al. | |
| 5,840,690 A | 11/1998 | Holick | |
| 5,840,837 A | 11/1998 | Krstenansky et al. | |
| 5,840,853 A | 11/1998 | Segre et al. | |
| 5,854,004 A | 12/1998 | Czernilofsky et al. | |
| 5,871,486 A | 2/1999 | Huebner et al. | |
| 5,874,086 A | 2/1999 | Krstenansky et al. | |
| 5,880,093 A | 3/1999 | Bagnoli | |
| 5,886,148 A | 3/1999 | Segre et al. | |
| 5,917,123 A | 6/1999 | McTiernan et al. | |
| 5,922,927 A | 7/1999 | Bujard et al. | |
| 5,977,070 A | 11/1999 | Piazza et al. | |
| 6,030,709 A | 2/2000 | Adermann et al. | |
| 6,030,790 A | 2/2000 | Adermann et al. | |
| 6,051,686 A | 4/2000 | Krstenansky et al. | |
| 6,066,618 A | 5/2000 | Holick | |
| 6,147,186 A | 11/2000 | Gardella et al. | |
| 6,183,974 B1 | 2/2001 | Bringhurst et al. | |
| 6,362,163 B1 | 3/2002 | Gardella et al. | |
| 6,417,333 B1 | 7/2002 | Bringhurst et al. | |
| 6,495,662 B1 | 12/2002 | Gardella et al. | |
| 6,537,965 B1 | 3/2003 | Bringhurst et al. | |
| 6,541,220 B1 | 4/2003 | Jüppner et al. | |
| 6,756,480 B2 | 6/2004 | Kostenuik et al. | |
| 6,803,213 B2 | 10/2004 | Bringhurst et al. | |
| 7,022,815 B1 | 4/2006 | Gardella et al. | |
| 7,033,773 B1 | 4/2006 | Bringhurst et al. | |
| 7,057,012 B1 | 6/2006 | Gardella et al. | |
| 7,078,487 B2 | 7/2006 | Jüppner et al. | |
| 7,132,260 B2 | 11/2006 | Segre et al. | |
| 7,150,974 B1 | 12/2006 | Segre et al. | |
| 7,153,951 B2 | 12/2006 | Gardella et al. | |
| 7,169,567 B1 | 1/2007 | Gardella et al. | |
| 7,244,834 B2 | 7/2007 | Gardella et al. | |
| 7,253,264 B1 | 8/2007 | Lauffer et al. | |
| 7,371,844 B2 | 5/2008 | Gardella et al. | |
| 7,479,478 B2 | 1/2009 | Bringhurst et al. | |
| 7,521,528 B2 | 4/2009 | Gardella et al. | |
| 7,572,765 B2 | 8/2009 | Gardella | |
| 2002/0110871 A1 | 8/2002 | Zahradnik et al. | |
| 2003/0144209 A1 | 7/2003 | Bringhurst et al. | |
| 2003/0162256 A1 | 8/2003 | Juppner et al. | |
| 2003/0166838 A1 | 9/2003 | Gardella et al. | |
| 2003/0171288 A1 | 9/2003 | Stewart | |
| 2004/0176285 A1 | 9/2004 | Juppner et al. | |
| 2005/0026839 A1* | 2/2005 | Gardella | 514/14 |
| 2005/0124537 A1 | 6/2005 | Kostenuik et al. | |
| 2005/0203012 A1 | 9/2005 | Bringhurst et al. | |
| 2005/0282749 A1 | 12/2005 | Henriksen et al. | |
| 2006/0078559 A1 | 4/2006 | Migeotte et al. | |
| 2007/0111946 A1 | 5/2007 | Gardella et al. | |
| 2007/0161569 A1 | 7/2007 | Gardella | |
| 2007/0203071 A1 | 8/2007 | Gardella | |

FOREIGN PATENT DOCUMENTS

| | | |
|---|---|---|
| CA | 2126132 | 12/1995 |
| CA | 2126299 | 12/2000 |
| EP | 0 341 962 | 11/1989 |
| EP | 0 464 533 | 1/1992 |
| EP | 0 477 885 | 4/1992 |
| EP | 0 561 412 | 9/1993 |
| EP | 0 748 817 | 12/1996 |
| EP | 0 783 522 | 7/1997 |
| GB | 2 269 176 | 2/1994 |
| JP | 58-96052 | 7/1983 |
| JP | 59-204159 | 11/1984 |
| JP | 5-32696 | 2/1993 |
| JP | 9-157294 | 6/1997 |
| WO | WO 87/01130 | 2/1987 |
| WO | WO 91/05050 | 4/1991 |
| WO | WO 92/01810 | 2/1992 |
| WO | WO 92/17581 | 10/1992 |
| WO | WO 92/17602 | 10/1992 |
| WO | WO 93/06121 | 4/1993 |
| WO | WO 93/06846 | 4/1993 |
| WO | WO 93/09222 | 5/1993 |
| WO | WO 93/11257 | 6/1993 |
| WO | WO 94/02510 | 2/1994 |
| WO | WO 94/12650 | 6/1994 |
| WO | WO 95/02610 | 1/1995 |
| WO | WO 95/11988 | 5/1995 |
| WO | WO 96/03437 | 2/1996 |
| WO | WO 96/10041 | 4/1996 |
| WO | WO 96/19206 | 6/1996 |
| WO | WO 97/02834 * | 1/1997 |
| WO | WO 98/05683 | 2/1998 |
| WO | WO 98/30590 | 7/1998 |
| WO | WO 99/18945 | 4/1999 |
| WO | WO 00/23594 | 4/2000 |
| WO | WO 00/31137 | 6/2000 |
| WO | WO 00/31266 | 6/2000 |
| WO | WO 00/32771 | 6/2000 |
| WO | WO 00/32775 | 6/2000 |
| WO | WO 00/39278 | 7/2000 |
| WO | WO 00/40698 | 7/2000 |
| WO | WO 01/23427 | 4/2001 |
| WO | WO 01/23521 | 4/2001 |
| WO | WO 03/09804 | 2/2003 |
| WO | WO 2004/067021 | 8/2004 |
| WO | WO 2004/093902 | 11/2004 |
| WO | WO 2005/009358 | 2/2005 |
| WO | WO 2008/019062 | 2/2008 |
| WO | WO 2009/017809 | 2/2009 |

OTHER PUBLICATIONS

Barden, J.A. and Kemp, B.E., "NMR Solution Structure of Human Parathyroid Hormone(1-34)," *Biochemistry* 32:7126-7132, American Chemical Society (1993).

Behar, V., et al., "Photoaffinity Cross-linking Identifies Differences in the Interactions of an Agonist and an Antagonist with the Parathyroid Hormone/Parathyroid Hormone-related Protein Receptor," *J. Biol. Chem.* 275:9-17, American Society for Biochemistry and Molecular Biology, Inc. (2000).

Bergwitz, C., et al., "Full Activation of Chimeric Receptors by Hybrids between Parathyroid Hormone and Calcitonin," *J. Biol. Chem.* 271:26469-26472, The American Society for Biochemistry and Molecular Biology, Inc. (1996).

Berridge, M.J., et al., "Changes in the levels of inositol phosphates after agonist-dependent hydrolysis of membrane phosphoinositides," *Biochem. J.* 212:473-482, The Biochemical Society (1983).

Bowen, W.P. and Jerman, J.C., "Nonlinear regression using spreadsheets," *Trends Pharmacol Sci* 16:413-417, Elsevier, Science Ltd. (1995).

Carter, P.H., et al., "Studies of the N-Terminal Region of a Parathyroid Hormone-Related Peptide(1-36) Analog: Receptor Subtype-Selective Agonists, Antagonists, and Photochemical Cross-Linking Agents," *Endocrinol.* 140:4972-4981, The Endocrine Society (1999).

Chen, Z., et al., "Solution Structure of the Osteogenic 1-31 Fragment of Human Parathyroid Hormone," *Biochemistry* 39:12766-12777, American Chemical Society (2000).

Chorev, M., et al., "Modifications of Position 12 in Parathyroid Hormone and Parathyroid Hormone Related Protein: Toward the Design of Highly Potent Antagonists," Biochemistry 29:1580-1586, American Chemical Society (1990).

Dempster, D.W., et al., "Anabolic Actions of Parathyroid Hormone on Bone," *Endocrine Rev. 14*:690-709, The Endocrine Society (1993).

Dempster, D.W., et al., "Erratum: Anabolic Actions of Parathyroid Hormone on Bone," *Endocrine Rev. 15*:261, The Endocrine Society (1994).

Fairwell, T., et al., "Total Solid-Phase Synthesis, Purification, and Characterization of Human Parathyroid Hormone-(1-84)," *Biochemistry 22*:2691-2697, American Chemical Society (1983).

Gronwald, W., et al., "Structure of Recombinant Human Parathyroid Hormone in Solution Using Multidimensional NMR Spectroscopy," *Chem. Hoppe-Seyler 377*:175-186, Walter de Gruyter & Co. (1996).

Goud, N.A., et al., "Solid-Phase Synthesis and Biologic Activity of Human Parathyroid Hormone(1-84)," *J. Bone Min. Res. 6*:781-789, Mary Ann Liebert, Inc. (1991).

Hoare, S.R.J., et al., "Evaluating the Signal Transduction Mechanism of the Parathyroid Hormone 1 Receptor," *J. Biol. Chem. 276*:7741-7753, American Society for Biochemistry and Molecular Biology, Inc. (2001).

Jüppner, H., et al., "A G Protein-Linked Receptor for Parathyroid Hormone and Parathyroid Hormone-Related Peptide," *Science 254*:1024-1026, American Society for the Advancement of Science (1991).

Kaul, R and Balram, P., "Stereochemical Control of Peptide Folding," *Bioorg. Med. Chem. 7*:105-117, Elsevier Science Ltd. (1999).

Kronenberg, H.M., et al., "Parathyroid Hormone: Biosynthesis, Secretion, Chemistry, and Action" in: *Handbook of Experimental Pharmacology*, Mundy, G.R., and Martin, T.J., eds., Springer-Verlag, Berlin, Germany, pp. 507-567 (1993).

Luck, M.D., et al., "The (1-14) Fragment of Parathyroid Hormone (PTH) Activates Intact and Amino-Terminally Truncated PTH-1 Receptors," *Mol. Endocrinol. 13*:670-680, The Endocrine Society (1999).

Marx, U.C., et al., "Structure of Human Parathyroid Hormone 1-37 in Solution," *J. Biol. Chem. 270*:15194-15202, The American Society for Biochemistry and Molecular Biology, Inc. (1995).

Marx, U.C., et al., "Structure-Activity Relation of $NH_2$-terminal Human Parathyroid Hormone Fragments," *J. Biol. Chem 273*:4308-4316, American Society for Biochemistry and Molecular Biology, Inc. (1998).

Marx, U.C., et al., "Solution Structures of Human Parathyroid Hormone Fragments hPTH(1-34) and hPTH (1-39) and Bovine Parathyroid Hormone Fragment bPTH(1-37)," *Biochem. Biophys. Res. Commun. 267*:213-220, Academic Press (2000).

Neer, R.M., et al., "Effect of Parathyroid Hormone (1-34) on Fractures and Bone Mineral Density in Postmenopausal Women with Osteoporosis," *N. Eng. J. Med. 344*:1434-1441, Massachusetts Medical Society (2001).

Pellegrini, M., et al., "Binding Domain of Human Parathyroid Hormone Receptor: From Conformation to Function," *Biochemistry 37*:12737-12743, American Chemical Society (1998).

Robinson J.R. ed., "Methods to Achieve Controlled Drug Delivery," in: *Sustained and Controlled Release Drug Delivery Systems*, Marcel Dekker, New York,NY, pp. 557-593 (1978).

Shen, V., et al., "Effects of Combined and Separate Intermittent Administration of Low-Dose Human Parathyroid Hormone Fragment (1-34) and 17β-Estradiol on Bone Histomorphometry in Ovariectomized Rats with Established Osteopenia," *Calcif Tissue Intl. 50*:214-220, Springer-Verlag Inc. (1992).

Shimizu, M., et al., "Autoactivation of Type-1 Parathyroid Hormone Receptors Containing a Tethered Ligand," *J. Biol. Chem. 275*:19456-19460, The American Society for Biochemistry and Molecular Biology, Inc. (2000).

Shimizu, M., et al., "Minimization of Parathyroid Hormone," *J. Biol. Chem. 275*:21836-21843, The American Society for Biochemistry and Molecular Biology, Inc. (2000).

Shimizu, M., et al., "Enhanced Activity in Parathyroid Hormone-(1-14) and -(1-11): Novel Peptides for Probing Ligand-Receptor Interactions," *Endocrinol. 142*:3068-3074, Endocrine Society (2001).

Shimizu, N., et al., "Parathyroid Hormone (PTH)-(1-14) and -(1-11) Analogs Conformationally Constrained by α-Aminosobutyric Acid Mediate Full Agonist Responses via the Juxtamembrane Region of the PTH-1 Receptor," *J. Biol. Chem. 276*:49003-49012, The American Society for Biochemistry and Molecular Biology, Inc. (2001).

Slovik, D.M., et al., "Restoration of Spinal Bone in Osteoporotic Men by Treatment with Human Parathyroid Hormone (1-34) and 1,25-Dihydroxyvitamin D," *J. Bone Min. Res. 1*:377-381, Mary Ann Liebert, Inc. (1986).

Takasu, H., et al., "Amino Terminal Modifications of Human Parathyroid Hormone (PTH) Selectively Alter Phospholipase C Signaling via the Type 1 PTH Receptor: Implications for Design for Signal-Specific PTH Ligands," *Biochemistry 38*:13453-13460, American Chemical Society (1999).

Takasu, H., et al., "Dual Signaling and Ligand Selectivity of the Human PTH/PTHrP Receptor," *J. Bone Min. Res. 14*:11-20, Blackwell Science, Inc. (1999).

Tregear, G.W., et al., "Bovine Parathyroid Hormone: Minimum Chain Length of Synthetic Peptide Required for Biological Activity," *Endocrinol. 93*:1349-1353, The Endocrine Society (1973).

Whitefield, J.F., et al., "Restoration of Severely Depleted Femoral Trabecular Bone in Ovariectomized Rats by Parathyroid Hormone-(1-34)," *Calcif. Tissue Int. 56*:227-231, Springer-Verlag Inc. (1995).

Whitfield, J.F., et al., "Comparison of the Ability of Recombinant Human Parathyroid Hormone, rhPTH-(1-84), and hPTH-(1-31)$NH_2$ Stimulate Femoral Trabecular Bone Growth in Ovariectomized Rats," *Calcif. Tissue Int. 60*:26-29, Springer-Verlag Inc. (1997).

Wold, F., "Posttranslational Protein Modifications: Perspectives and Prospects," in *Posttranslational Covalent Modifications of Proteins*, B.C. Johnson, eds., Academic Press, Inc., New York, pp. 1-12 (1983).

Abou-Samra et al., "Expression Cloning of a Common Receptor for Parathyroid Hormone and Parathyroid Hormone-related Peptide From Rat Osteoblast-like Cells: A Single Receptor Stimulates Intracellular Accumulation of Both cAMP and Inositol Trisphosphates and Increases Intracellular Free Calcium," *Proc Natl Acad Sci U S A. 89*:2732-2736 (1992).

Azarani et al., "Structurally Diverse N-terminal Peptides of Parathyroid Hormone (PTH) and PTH-related Peptide (PTHRP) Inhibit the $Na^+/H^+$ Exchanger NHE3 Isoform by Binding to the PTH/PTHRP Receptor Type I and Activating Distinct Signaling Pathways," *J Biol Chem. 271*:14931-14936 (1996).

Bergwitz et at, "Residues in the Membrane-spanning and Extracellular Loop Regions of the Parathyroid Hormone (PTH)-2 Receptor Determine Signaling Selectivity for PTH and PTH-related Peptide," *J Biol Chem. 272*:28861-28868 (1997).

Born et al., "Inhibition of Parathyroid Hormone Bioactivity by Human Parathyroid Hormone (PTH)-(3-84) and PTH-(8-84) Synthesized in *Escherichia coli*," *Endocrinology. 123*:1848-1853 (1988).

Bryant et al., "Helix-inducing α-aminoisobutyric Acid in Opioid Mimetic Deltorphin C Analogues," *J Med Chem. 40*:2579-2587 (1997).

Cervini et al., "Human Growth Hormone-releasing hGHRH(1-29)-$NH_2$: Systematic Structure-activity Relationship Studies," *J Med Chem. 41*:717-727 (1998).

Chakravarthy et al., "Parathyroid Hormone Fragment [3-34] Stimulates Protein Kinase C (PKC) Activity in Rat Osteosarcoma and Murine T-lymphoma Cells," *Biochem Biophys Res Commun. 171*:1105-1110 (1990).

Civitelli et al., "PTH Elevates Inositol Polyphosphates and Diacylglycerol in a Rat Osteoblast-like Cell Line," *Am J Physiol. 255*:E660-667 (1988).

Cohen et al., "Analogues of Parathyroid Hormone Modified at Positions 3 and 6. Effects on Receptor Binding and Activation of Adenylyl Cyclase in Kidney and Bone," *J Biol Chem. 266*:1997-2004 (1991).

Cole et al., "Regulation of Sodium-dependent Phosphate Transport by Parathyroid Hormone in Opossum Kidney Cells: Adenosine 3′, 5′-Monophosphate-dependent and -Independent Mechanisms," *Endocrinology. 122*:2981-2989 (1988).

Cunningham et al., "High-resolution Epitope Mapping of hGH-receptor Interactions by Alanine-scanning Mutagenesis," *Science. 244*:1081-1085 (1989).

Donahue et al., "Differential Effects of Parathyroid Hormone and Its Analogues on Cytosolic Calcium Ion and cAMP Levels in Cultured Rat Osteoblast-like Cells," *J Biol Chem. 263*:13522-13527 (1988).

Dunlay et al., "PTH Receptor Coupling to Phospholipase C is an Alternate Pathway of Signal Transduction in Bone and Kidney," *Am J Physiol*. 258:F223-F231 (1990).

Fujimori et al., "Structure-function Relationship of Parathyroid Hormone: Activation of Phospholipase-C, Protein Kinase-A and -C in Osteosarcoma Cells," *Endocrinology*. 130:29-36 (1992).

Gaich et al., "Amino-terminal Parathyroid Hormone-related Protein: Specific Binding and Cytosolic Calcium Responses in Rat Insulinoma Cells," *Endocrinology*. 132:1402-1409 (1993).

Gardella et al., "Analysis of Parathyroid Hormone's Principal Receptor-binding Region by Site-directed Mutagenesis and Analog Design," *Endocrinology*. 132:2024-2030 (1993).

Gardella et al., "Converting Parathyroid Hormone-related Peptide (PTHrP) Into a Potent PTH-2 Receptor Agonist," *J Biol Chem*. 271:19888-19893 (1996).

Gardella et al., "Determinants of [Arg$^2$]PTH-(1-34) Binding and Signaling in the Transmembrane Region of the Parathyroid Hormone Receptor," *Endocrinology*. 135:1186-1194 (1994).

Gardella et al., "Mutational Analysis of the Receptor-activating Region of Human Parathyroid Hormone," *J Biol Chem*. 266:13141-13146 (1991).

Gardella et al., "Parathyroid Hormone (PTH)-PTH-related Peptide Hybrid Peptides Reveal Functional Interactions Between the 1-14 and 15-34 Domains of the Ligand," *J Biol Chem*. 270:6584-6588 (1995).

Gardella et al., "Transmembrane Residues of the Parathyroid Hormone (PTH)/PTH-related Peptide Receptor That Specifically Affect Binding and Signaling by Agonist Ligands," *J Biol Chem*. 271:12820-12825 (1996).

Goltzmann et al., "Analysis of the Requirements for Parathyroid Hormone Action in Renal Membranes with the Use of Inhibiting Analogues," *J Biol Chem*. 250:3199-3203 (1975).

Gombert et al., "Alanine and D-amino Acid Scan of Human Parathyroid Hormone," *Peptides: Chemistry Structure and Biology. Proceedings of the 14$^{th}$ American Peptide Symposium*, Jun. 18-23, Kaumaya, P.T.P., and Hodges, Editors 661-662 (1996).

Guo et al., "Parathyroid Hormone (PTH)/PTH-related Peptide Receptor Density Modulates Activation of Phospholipase C and Phosphate Transport by PTH in LLC-PK1 Cells," *Endocrinology*. 136:3884-3891 (1995).

Hilliker et al., "Truncation of the Amino Terminus of PTH Alters Its Anabolic Activity on Bone in Vivo," *Bone*. 19:469-477 (1996).

Horiuchi et al., "A Parathyroid Hormone Inhibitor In Vivo: Design and Biological Evaluation of a Hormone Analog," *Science*. 220:1053-1055 (1983).

Hruska et al., "Stimulation of Inositol Trisphosphate and Diacylglycerol Production in Renal Tubular Cells by Parathyroid Hormone," *J Clin Invest*. 79:230-239 (1987).

Iida-Klein et al., "Mutations in the Second Cytoplasmic Loop of the Rat Parathyroid Hormone (PTH)/PTH-related Protein Receptor Result in Selective Loss of PTH-stimulated Phospholipase C Activity," *J Biol Chem*. 272:6882-6889 (1997).

Iida-Klein et al., "Truncation of the Carboxyl-terminal Region of the Rat Parathyroid Hormone (PTH)/PTH-related Peptide Receptor Enhances PTH Stimulation of Adenylyl Cyclase but Not Phospholipase C," *J Biol Chem*. 270:8458-8465(1995).

Jobert et al., "Parathyroid Hormone-induced Calcium Release from Intracellular Stores in a Human Kidney Cell Line in the Absence of Stimulation of Cyclic Adenosine 3',5'-monophosphate Production," *Endocrinology*. 138:5282-5292 (1997).

Jouishomme et al., "Further Definition of the Protein Kinase C Activation Domain of the Parathyroid Hormone," *J Bone Miner Res*. 9:943-949 (1994).

Joun et al., "Tissue-specific Transcription Start Sites and Alternative Splicing of the Parathyroid Hormone (PTH)/PTH-related Peptide (PTHrP) Receptor Gene: A New PTH/PTHrP Receptor Splice Variant that Lacks the Signal Peptide," *Endocrinology*. 138:1742-1749 (1997).

Jüppner et al., "Properties of Amino-terminal Parathyroid Hormone-related Peptides Modified at Positions 11-13," *Peptides*. 11:1139-1142 (1990).

Jüppner et al., "The Extracellular Amino-terminal Region of the Parathyroid Hormone (PTH)/PTH-related Peptide Receptor Determines the Binding Affinity for Carboxyl-terminal Fragments of PTH-(1-34)," *Endocrinology*. 134:879-884 (1994).

Jüppner et al., "The Parathyroid Hormone-like Peptide Associated with Humoral Hypercalcemia of Malignancy and Parathyroid Hormone Bind to the Same Receptor on the Plasma Membrane of ROS 17/2.8 Cells," *J Biol Chem*. 263:8557-8560 (1988).

Kong et al., "The Rat, Mouse and Human Genes Encoding the Receptor for Parathyroid Hormone and Parathyroid Hormone-related Peptide are Highly Homologous," *Biochem Biophys Res Commun*. 200:1290-1299 (1994).

Kovacs et al., "Parathyroid Hormone-related Peptide (PTHrP) Regulates Fetal-placental Calcium Transport Through a Receptor Distinct from the PTH/PTHrP Receptor," *Proc Natl Acad Sci U S A*. 93:15233-15238 (1996).

Lee et al., "Homolog-scanning Mutagenesis of the Parathyroid Hormone (PTH) Receptor Reveals PTH-(1-34) Binding Determinants in the Third Extracellular Loop," *Mol Endocrinol*. 9:1269-1278 (1995).

Lee et al., "Role of the Extracellular Regions of the Parathyroid Hormone (PTH)/PTH-related Peptide Receptor in Hormone Binding," *Endocrinology*. 135:1488-1495 (1994).

Mannstadt et al., "Evidence for a Ligand Interaction Site at the Amino-terminus of the Parathyroid Hormone (PTH)/PTH-related Protein Receptor from Cross-linking and Mutational Studies," *J Biol Chem*. 273:16890-16896 (1998).

Moretto et al., "(αMe)Nva: Stereoselective Syntheses and Preferred Conformations of Selected Model Peptides," *J Pept Res*. 56:283-97 (2000).

Neugebauer et al., "Solution Structure and Adenylyl Cyclase Stimulating Activities of C-terminal Truncated Human Parathyroid Hormone Analogues," *Biochemistry*. 34:8835-8842 (1995).

Nussbaum et al., "Parathyroid Hormone Renal Receptor Interactions. Demonstration of Two Receptor-binding Domains," *J Biol Chem*. 255:10183-10187 (1980).

Nutt et al., "Removal of Partial Agonism from Parathyroid Hormone (PTH)-related Protein-(7-34)NH$_2$ by Substitution of PTH Amino Acids at Positions 10 and 11," *Endocrinology*. 127:491-493 (1990).

Orloff et al., "Analysis of PTHRP Binding and Signal Transduction Mechanisms in Benign and Malignant Squamous Cells," *Am J Physiol*. 262:E599-E607 (1992).

Orloff et al., "Further Evidence for a Novel Receptor for Amino-terminal Parathyroid Hormone-related Protein on Keratinocytes and Squamous Carcinoma Cell Lines," *Endocrinology*. 136:3016-3023 (1995).

Orloff et al., "A Midregion Parathyroid Hormone-related Peptide Mobilizes Cytosolic Calcium and Stimulates Formation of Inositol Trisphosphate in a Squamous Carcinoma Cell Line," *Endocrinology*. 137:5376-5385 (1996).

Plotkin et al., "Dissociation of Bone Formation from Resorption During 2-week Treatment with Human Parathyroid Hormone-related Peptide-(1-36) in Humans: Potential as an Anabolic Therapy for Osteoporosis," *J Clin Endocrinol Metab*. 83:2786-2791 (1998).

Potts, Jr. et al., "Structure Based Design of Parathyroid Hormone Analogs," *J Endocrinol*. 154:S15-S21 (1997).

Reid et al., "Parathyroid Hormone Acutely Elevates Intracellular Calcium in Osteoblastlike Cells," *Am J Physiol*. 253:E45-E51 (1987).

Rixon et al., "Parathyroid Hormone Fragments May Stimulate Bone Growth in Ovariectomized Rats by Activating Adenylyl Cyclase," *J Bone Miner Res*. 9:1179-1189 (1994).

Roe et al., "Parathyroid Hormone 1-34 (hPTH 1-34) and Estrogen Produce Dramatic Bone Density Increases in Postmenopausal Osteoporosis-Results from a Placebo-controlled Randomized Trial," *J Bone Miner Res*. 14:S137 (1999) (Abstract 1019).

Schipani et al., "Identical Complementary Deoxyribonucleic Acids Encode a Human Renal and Bone Parathyroid Hormone (PTH)/PTH-related Peptide Receptor," *Endocrinology*. 132:2157-2165 (1993).

Schneider et al., "A C-terminally Truncated Human Parathyroid Hormone Receptor Is Functional and Activates Multiple G Proteins," *FEBS Lett*. 351:281-285 (1994).

Schneider et al., "Cloning and Functional Expression of a Human Parathyroid Hormone Receptor," *Eur J Pharmacol*. 246:149-155 (1993).

Segre et al., "Characterization of Parathyroid Hormone Receptors in Canine Renal Cortical Plasma Membranes Using a Radioiodinated Sulfur-free Hormone Analogue. Correlation of Binding with Adenylate Cyclase Activity," *J Biol Chem*. 254:6980-6986 (1979).

Seuwen et al., "Heparin-insensitive Calcium Release from Intracellular Stores Triggered by the Recombinant Human Parathyroid Hormone Receptor," *Br J Pharmacol*. 114:1613-1620 (1995).

Shimada et al., "Purification and Characterization of a Receptor for Human Parathyroid Hormone and Parathyroid Hormone-related Peptide," *J Biol Chem*. 277:31774-31780 (2002).

Shimizu et al., "Functional Evidence for an Intramolecular Side Chain Interaction Between Residues 6 and 10 of Receptor-bound Parathyroid Hormone Analogues," *Biochemistry*. 42:2282-2290 (2003).

Shimizu et al., "Structurally Varied Conformationally Constrained Amino Acids Substitutions at Positions 1 and 3 of PTH(1-14) Preserve or Enhance P1R Binding Affinity and cAMP-signaling Potency," *J Bone Miner Res*. 17:S389 (2002).

Shimizu et al., "Type-substitution Analysis of the Amino-terminal Fragment of Parathyroid Hormone, PTH(1-14): An Approach Toward New Low Molecular Weight PTH Agonists," *J Bone Miner Res*. 14:S289 (1999) (Abstract F398).

Shukunami et al., "Chondrogenic Differentiation of Clonal Mouse Embryonic Cell Line ATDC5 In Vitro: Differentiation-dependent Gene Expression of Parathyroid Hormone (PTH)/PTH-related Peptide Receptor," *J Cell Biol*. 133:457-468 (1996).

Suva et al., "A Parathyroid Hormone-related Protein Implicated in Malignant Hypercalcemia: Cloning and Expression," *Science*. 237:893-896 (1987).

Takasu et al., "Type-1 Parathyroid Hormone (PTH)/PTH-related Peptide (PTHrP) Receptors Activate Phospholipase C in Response to Carboxyl-truncated Analogs of PTH(1-34)," *Endocrinology*. 139:4293-4299 (1998).

Takasu et al., "The 69-84 Amino Acid Region of the Parathyroid Hormone Molecule Is Essential for the Interaction of the Hormone with the Binding Sites with Carboxyl-terminal Specificity," *Endocrinology*. Dec. 1996;137:5537-5543 (1996).

Tamura et al., "Parathyroid Hormone 1-34, but Not 3-34 or 7-34, Transiently Translocates Protein Kinase C in Cultured Renal (OK) Cells," *Biochem Biophys Res Commun*. 159:1352-1358 (1989).

Tregear et al., "Synthetic Analogues of Residues 1-34 of Human Parathyroid Hormone: Influence of Residue No. 1 on Biological Potency In Vitro," *Endocr Res Commun*. 2:561-570 (1975).

Turner et al., "Single Mutations Allow the PTH2 Receptor to Respond to PTHrP," *J Bone Miner Res*. 12:S133 (1997) (Abstract 121).

Turner et al., "Transmembrane Residues Together with the Amino Terminus Limit the Response of the Parathyroid Hormone (PTH) 2 Receptor to PTH-related Peptide," *J Biol Chem*. 273:3830-3837 (1998).

Ureña at al., "Regulation of Parathyroid Hormone (PTH)/PTH-related Peptide Receptor Messenger Ribonucleic; Acid by Glucocorticoids and PTH in ROS 17/2.8 and OK Cells," *Endocrinology*. 134:451-456 (1994).

Usdin et al., "Identification and Functional Expression of a Receptor Selectively Recognizing Parathyroid Hormone, the PTH2 Receptor." *J Biol Chem*. 270:15455-15458 (1995).

Whitfield et al., "Stimulation of the Growth of Femoral Trabecular Bone in Ovariectomized Rats by the Novel Parathyroid Hormone Fragment, hPTH-(1-31)NH$_2$ (Ostabolin)," *Calcif Tissue Int*. 58:81-87 (1996).

Wu et al., "Structural and Physiologic Characterization of the Midregion Secretory Species of Parathyroid Hormone-related Protein," *J Biol Chem*. 271:24371-24381 (1996).

Yamamoto et al., "Centrally Administered Parathyroid Hormone (PTH)-related Protein(1-34) but Not PTH(1-34) Stimulates Arginine-vasopressin Secretion and Its Messenger Ribonucleic Acid Expression in Supraoptic Nucleus of the Conscious Rats," *Endocrinology*. 139:383-388 (1998).

Yamamoto et al., "Parathyroid Hormone-related Peptide-(1-34) [PTHrP-(1-34)] Induces Vasopressin Release from the Rat supraoptic Nucleus in Vitro Through a Novel Receptor Distinct from a Type I or Type II PTH/PTHrP Receptor," *Endocrinology*. 138:2066-2072 (1997).

Zhou et al., "Direct Mapping of an Agonist-binding Domain within the Parathyroid Hormone/parathyroid Hormone-related Protein Receptor by Photoaffinity Crosslinking," Proc Natl Acad Sci U S A 94:3644-3649 (1997).

Communication and Supplementary European Search Report mailed Jun. 3, 2009 (EP 03 71 6681).

Abou-Samra et al., "Phorbol 12-Myristate 13-Acetate and Vasopressin Potentiate the Effect of Corticotropin-Releasing Factor on Cyclic AMP Production in Rat Anterior Pituitary Cells. Mechanisms of Action," *J. Biol. Chem*. 262: 1129-1136 (1987).

Abou-Samra et al., "Non-Homologous Sequences of Parathyroid Hormone and the Parathyroid Hormone Related Peptide Bind to a Common Receptor on ROS 17/2.8 Cells," *Endocrinology* 125: 2215-2217 (1989).

Abou-Samra et al., "Cyclic Adenosine 3', 5'-Monophosphate (cAMP)-Dependent and cAMP-Independent Regulation of Parathyroid Hormone Receptors on UMR 106-01 Osteoblastic Osteosarcoma Cells," *Endocrinology* 129: 2547-2554 (1991).

Abou-Samra et al., "Down-Regulation of Parathyroid (PTH)/PTH-Related Peptide Receptor Immunoreactivity and PTH Binding in Opossum Kidney Cells by PTH and Dexamethasone," *Endocrinology* 135: 2588-2594 (1994).

Adams et al., "Probing the Bimolecular Interactions of Parathyroid Hormone and the Human Parathyroid Hormone/Parathyroid Hormone-Related Protein Receptor. 2. Cloning, Characterization, and Photoaffinity Labeling of the Recombinant Human Receptor," *Biochemistry* 34: 10553-10559 (1995).

Alberts et al., "Chapter 6: Basic Genetic Mechanisms" in: *Molecular Biology of the Cell*, 3rd Edition, pp. 234-237 and the Genetic Code Table (Garland Pub., New York, NY, 1994).

Azarani et al., "Parathyroid Hormone and Parathyroid Hormone-Related Peptide Activate the Na+ /H+ Exchanger NHE-1 Isoform in Osteoblastic Cells (UMR-106) via a cAMP-dependent Pathway," *J. Biol. Chem*. 270: 23166-23172 (1995).

Barbier et al., "Bioactivities and Secondary Structures of Constrained Analogues of Human Parathyroid Hormone: Cyclic Lactams of the Receptor Binding Region," *J. Med. Chem*. 40:1373-1380 (1997).

Barbier et al., "Structural Requirements for Conserved Arginine of Parathyroid Hormone," *Biochemistry* 40: 8955-8961 (2001).

Barbier et al "Backbone-Methylated Analogues of the Principle Receptor Binding Region of Human Parathyroid Hormone. Evidence for Binding to Both the N-Terminal Extracellular Domain and Extracellular Loop Region," *J. Biol. Chem*. 280: 23771-23777 (2005).

Barden et al., "NMR Study of a 34-Residue N-Terminal Fragment of a Parathyroid Hormon-Related Protein Secreted During Humoral Hypercalcemia of Malignancy," *Eur. J. Biochem*. 184: 379-394 (1989).

Barden et al., "Stabilized NMR Structure of the Hypercalcemia of Malignancy Peptide PTHrP[Ala-26](1-34)Amide," *Biochim. Biophys. Acta* 1208: 256-262 (1994).

Becker et al., "Procedure Guideline for Thyroid Scintigraphy: 1.0. Society of Nuclear Medicine," *J. Nucl. Med*. 37: 1264-1266 (1996).

Behar et al., "Histidine at Position 5 is the Specificity "Switch" between Two Parathyroid Hormone Receptor Subtypes," *Endocrinology* 137: 4217-4224 (1996).

Bergwitz et al., "Identification, Functional Characterization, and Developmental Expression of Two Nonallelic Parathyroid Hormone (PTH)/PTH-Related Peptide Receptor Isoforms in *Xenopus laevis* (Daudin)," *Endocrinology* 139: 723-732 (1998).

Berlot, "A Highly Effective Dominant Negative Alpha s Construct Containing Mutations that Affect Distinct Functions Inhibits Multiple Gs-Coupled Receptor Signaling Pathways," *J. Biol. Chem*. 277: 21080-21085 (2002).

Bettoun et al., "Cloning and Characterization of the Promoter Regions of the Human Parathyroid Hormone (PTH)/PTH-Related Peptide Receptor Gene: Analysis of Deoxyribonucleic Acid from Normal Subjects and Patients with Pseudohypoparathyroidism Type 1b," *J. Clin. Endocrinol. Metab*. 82: 1031-1040 (1997).

Bettoun et al., "Developmental Upregulation of Human Parathyroid Hormone (PTH)/PTH-Related Peptide Receptor Gene Expression from Conserved and Human-specific Promoters," *J. Clin. Invest.* 102: 958-967 (1998).

Bisello et al., "Parathyroid Hormone-Receptor Interactions Identified Directly by Photocross-Linking and Molecular Modeling Studies," *J. Biol. Chem.* 273: 22498-22505 (1998).

Bisello et al., "Selective Ligand-Induced Stabilization of Active and Desensitized Parathyroid Hormone Type 1 Receptor Conformations," *J. Biol. Chem.* 277: 38524-38530 (2002).

Bork et al., "Go Hunting in Sequence Databases but Watch Out for the Traps," *Trends Genet.* 12: 425-427 (1996).

Bork, "Powers and Pitfalls in Sequence Analysis: The 70% Hurdle," *Genome Res.* 10: 398-400 (2000).

Bos et al., "Expression of the Parathyroid Hormone Receptor and Correlation with Other Osteoblastic Parameters in Fetal Rat Osteoblasts," *Calcif. Tisse Int.* 58:95-100 (1996).

Brenner, "Errors in Genome Annotation," *Trends Genet.* 15: 132-133 (1999).

Bringhurst et al., "Cloned, Stably Expressed Parathyroid Hormone (PTH)/PTH-Related Peptide Receptors Activate Multiple Messenger Signals and Biological Responses in LLC-PK1 Kidney Cells," *Endocrinology* 132: 2090-2098 (1993).

Broadus et al., "Parathyroid Hormone-Related Protein: Structure, Processing, and Physiological Actions," in: *The Parathyroids* (eds. J. P. Bilezikan et al.), pp. 259-294 (Raven Press Ltd., New York, NY, 1994).

Bundi et al., "Characterisation of a Local Structure in the Synthetic Parathyroid Hormone Fragment 1-34 by 1H Nuclear-Magnetic-Resonance Techniques," *Eur. J. Biochem.* 91: 201-208 (1978).

Campbell et al., "Totipotency or Multipotentiality of Cultured Cells: Applications and Progress," *Theriogenology* 47: 63-72 (1997).

Carter et al., "Zinc(II)-Mediated Enhancement of the Agonist Activity of Histidine-Substituted Parathyroid Hormone (1-14) Analogues," *Biochem. Biophys. Acta* 1538: 290-304 (2001).

Castro et al., "Dual Regulation of the Parathyroid Hormone (PTH)/PTH-Related Peptide Receptor Signaling by Protein Kinase C and Beta-Arrestins," *Endocrinology* 143: 3854-3865 (2002).

Castro et al., "Turn-On Switch in Parathyroid Hormone Receptor by a Two-Step Parathyroid Hormone Binding Mechanism," *Proc. Natl. Acad. Sci. USA* 102: 16084-16089 (2005).

Catanzariti et al., "A Novel Expression System for Gs-Coupled Receptors," *Bio Techniques* 15: 474-479 (1993).

Caulfield et al., "The Bovine Renal Parathyroid Hormone (PTH) Receptor has Equal Affinity for Two Different Amino Acid Sequences: The Receptor Binding Domains of PTH and PTH-related Protein are Located within the 14-34 Region," *Endocrinology* 127: 83-87 (1990).

Caulfield et al., "Parathyroid Hormone-Receptor Interactions," *Trends Endocrinol. Metab.* 1: 164-168 (1990).

Chakrabartty, "Large Differences in the Helix Propensities of Alanine and Glycine," *Nature* 351: 586-588 (1991).

Chauvin et al., "Parathyroid Hormone Receptor Recycling: Role of Receptor Dephosphorylation and Beta-Arrestin," *Mol. Endocrinol.* 16: 2720-2732 (2002).

Chorev et al., "Cyclic Parathyroid Hormone Related Protein Antagonists: Lysine 13 to Aspartic Acid 17 [i to (i+4)] Side Chain to Side Chain Lactamization," *Biochemistry* 30: 5968-5974 (1991).

Chu et al, "Porcine Proparathyroid Hormone. Identification, Biosynthesis, and Partial Amino Acid Sequence," *Biochemistry* 14: 3631-3635 (1975).

Civitelli et al., "Parathyroid Hormone-Related Peptide Transiently Increases Cytosolic Calcium in Osteoblast-Like Cells: Comparison with Parathyroid Hormone," *Endocrinology* 125: 1204-1210 (1989).

Colquhoun, "Binding, Gating, Affinity, and Efficacy: The Interpretation of Structure-Activity Relationships for Agonists and of the Effects of Mutating Receptors," *Br. J. Pharmacol.* 125: 924-947 (1998).

Condon et al., "The Bioactive Conformation of Human Parathyroid Hormone. Structural Evidence for the Extended Helix Postulate," *J. Am. Chem. Soc.* 122: 3007-3014 (2000).

Cwirla et al., "Peptide Agonist of the Thrombopoietin Receptor as Potent as the Natural Cytokine," *Science* 276: 1696-1699 (1997).

Dang et al., "Gene Therapy and Translational Cancer Research," *Clin. Cancer Res.* 5: 471-474 (1999).

Dautzenberg et al., "Mapping of the Ligand-Selective Domain of the *Xenopus laevis* Corticotropin-Releasing Factor Receptor 1: Implications for the Ligand-Binding Site," *Proc. Natl. Acad. Sci. USA* 95: 4941-4946 (1998).

DeAlmeida et al., "Identification of Binding Domains of the Growth Hormone-Releasing Hormone Receptor by Analysis of Mutant and Chimeric Receptor Proteins," *Mol. Endocrinol.* 12: 750-765 (1998).

Dean et al., "Mechanisms of Ligand Binding to the Parathyroid Hormone (PTH)/PTH-Related Protein Receptor: Selectivity of a Modified PTH(1-15) Radioligand for GalphaS-Coupled Receptor Conformations," *Mol. Endocrinol.* 20: 931-943 (2006).

Dempster et al., "On the Mechanism of Cancellous Bone Preservation in Postmenopausal Women with Mild Primary Hyperparathyroidism," *J. Clin. Endocrinol. Metab.* 84: 1562-1566 (1999).

Ding et al., "A Single Amino Acid Determines the Immunostimulatory Activity of Interleukin 10," *J. Exp. Med.* 191:213-223 (2000).

Doerks et al., "Protein Annotation: Detective Work for Function Prediction," *Trends Genet.* 14: 248-250 (1998).

Dohlman et al., "Model Systems for the Study of Seven-Transmembrane-Segment Receptors," *Annu. Rev. Biochem.* 60: 653-688 (1991).

Dong et al., "Demonstration of a Direct Interaction between Residue 22 in the Carboxyl-Terminal Half of Secretin and the Amino-Terminal Tail of the Secretin Receptor Using Photoaffinity Labeling," *J. Biol. Chem.* 274: 903-909 (1999).

Ebert et al., "A Moloney MLV-Rat Somatotropin Fusion Gene Produces Biologically Active Somatotropin in a Transgenic Pig," *Mol. Endocrinol.* 2: 277-283 (1988).

Epand, "Relationships Among Several Different Non-Homologous Polypeptide Hormones," *Mol. Cell Biochem.* 57: 41-47 (1983).

Fischer et al., "Human Parathyroid Hormone. Immunological Characterization of Antibodies Against a Glandular Extract and the Synthetic Amino-Terminal Fragments 1-12 and 1-34 and their Use in the Determination of Immunoreactive Hormone in Human Sera," *J. Clin. Invest.* 54: 1382-1394 (1974).

Freyaldenhoven et al., "Protein Kinase C Differentially Modulates PTH- and PGE2 -Sensitive Adenylate Cyclase in Osteoblast-Like Cells," *Am. J. Physiol.* 262: E87-E95 (1992).

Fujimori et al., "Dissociation of Second Messenger Activation by Parathyroid Hormone Fragments in Osteosarcoma Cells," *Endocrinology* 128: 3032-3039 (1991).

Fukayama et al., "Mechanisms of Desensitization to Parathyroid Hormone in Human Osteoblast-Like SaOS-2 Cells," *Endocrinology* 131: 1757-1769 (1992).

Fukayama et al., "Role of Protein Kinase-A in Homologous Down-Regulation of Parathyroid Hormone (PTH)/PTH-Related Peptide Receptor Messenger Ribonucleic Acid in Human Osteoblast-Like SaOS-2 Cells," *Endocrinology* 134: 1851-1858 (1994).

Gardella et al., "Expression of Human Parathyroid Hormone-(1-84) in *Escherichia coli* as a Factor X-cleavable Fusion Protein," J. Biol. Chem. 265: 15854-15859 (1990).

Gardella et al., "Scanning Mutagenesis of the 23-35 Region of Parathyroid Hormone Reveals Important Determinants of Receptor Binding," in: *Calcium Regulating Hormones and Bone Metabolism: Basic and Clinical Aspects* (eds. D.V. Cohn et al.), vol. 11, pp. 218-222 (Excerpta Medica, Amsterdam, 1992).

Gensure et al., "Multiple Sites of Contact between the Carboxyl-Terminal Binding Domain of PTHrP-(1-36) Analogs and the Amino-Terminal Extracellular Domain of the PTH/PTHrP Receptor Identified by Photoaffinity Cross-Linking," *J. Biol. Chem.* 276: 28650-28658 (2001).

Gensure et al., "Identification of a Contact Site for Residue 19 of Parathyroid Hormone (PTH) and PTH-Related Protein Analogs in Transmembrane Domain Two of the Type 1 PTH Receptor," *Mol Endocrinol.* 17: 2647-2658 (2003).

Gensure et al., "Parathyroid Hormone and Parathyroid Hormone-Related Peptide, and their Receptors," *Biochem. Biophys. Res. Commun.* 328: 666-678 (2005).

Goltzman et al., "Influence of Guanyl Nucleotides on Parathyroid Hormone-Stimulated Adenylyl Cyclase Activity in Renal Cortical Membranes," *Endocrinology* 103: 1352-1360 (1978).

Grace et al., "NMR Structure and Peptide Hormone Binding Site of the First Extracellular Domain of a Type B1 G Protein-Coupled Receptor," *Proc. Natl. Acad. Sci. USA* 101: 12836-12841 (2004).

Greenberg et al. "Mapping the Bimolecular Interface of the Parathyroid Hormone (PTH)-PTH1 Receptor Complex: Spatial Proximity between Lys(27) (of the Hormone Principal Binding Domain) and Leu(261) (of the First Extracellular Loop) of the Human PTH1 Receptor," Biochemistry 39: 8142-8152 (2000).

Habashita et al., "Synthesis and Biological Activities of hPTH(1-34) Analogues: Modification of the Middle Part and C-terminal Alkylamides," in: *Peptide Science- Present and Future: Proceedings of the 1st International Peptide Symposium* (ed. Y. Shimonishi), pp. 711-713 (Kluwer Acad. Pub., Great Britain, 1997).

Hammer et al., "Genetic Engineering of Mammalian Embryos," *J. Anim. Sci.* 63: 269-278 (1986).

Heinrich et al., "Gene Encoding Parathyroid Hormone. Nucleotide Sequence of the Rat Gene and Deduced Amino Acid Sequence of Rat Preproparathyroid Hormone," *J. Biol. Chem.* 259: 3320-3329 (1984).

Heinrich et al., "Rat Parathyroid Hormone Gene, Exons II and III," Alignment result 8, SEQ ID No. 1, Database: GenEmbl, Accession No. K01268 (Apr. 27, 1993).

Hjorth et al., "Constitutive Activity of Glucagon Receptor Mutants," *Mol. Endocrinol.* 12:78-86 (1998).

Hoare et al., "Measurement of Agonist and Antagonist Ligand-Binding Parameters at the Human Parathyroid Hormone Type 1 Receptor: Evaluation of Receptor States and Modulation by Guanine Nucleotide," *J. Pharmacol. Exp. Ther.* 289: 1323-1333 (1999).

Holtmann et al., "Critical Contributions of Amino-terminal Extracellular Domains in Agonist Binding and Activation of Secretin and Vasoactive Intestinal Polypeptide Receptors. Studies of Chimeric Receptors," *J. Biol. Chem.* 270: 14394-14398 (1995).

Holtmann et al., "Molecular Basis and Species Specificity of High Affinity Binding of Vasoactive Intestinal Polypeptide by the Rat Secretin Receptor. Effec of Receptor-G-Protein Interaction on the Ligand Binding Mechanism and Receptor Conformation," *J. Pharmacol. Exp. Ther.* 279: 555-560 (1996).

Horiuchi et al., "Evaluation of a Parathyroid Hormone Antagonist in an In Vivo Multiparameter Bioassay," *Am. J. Physiol.* 253: E187-192 (1987).

Iida-Klein et al., "Structural Requirements of Parathyroid Hormone/Parathyroid Hormone-Related Peptide Receptors for Phospholipase C Activation and Regulation of Phosphate Uptake," *Miner. Electrolyte Metab.* 21: 177-179 (1995).

Inomata et al., "Characterization of a Novel Parathyroid Hormone (PTH) Receptor with Specificity for the Carboxyl-Terminal Region of PTH-(1-84)," *Endocrinology* 136: 4732-4740 (1995).

Ishihara et al., "Molecular Cloning and Expression of a cDNA Encoding the Secretin Receptor," *EMBO J.* 10: 1635-1641 (1991).

Iwakura et al., "Effects of the Length of a Glycine Linker Connecting the N-and C-Termini of a Circularly Permuted Dihydrofolate Reductase," *Protein Eng.* 11: 707-713 (1998).

Jans et al., "LLC-PK1 Cell Mutants in cAMP Metabolism Respond Normally to Phorbol Esters," *FEBS Lett.* 205: 127-131 (1986).

Janulis et al., "Structure-Function Requirements of Parathyroid Hormone for Stimulation of 1,25-Dihydroxyvitamin D3 Production by Rat Renal Proximal Tubules," *Endocrinology* 133: 713-719 (1993).

Ji et al., "Human Choriogonadotropin Binds to a Lutropin Receptor with Essentially No N-terminal Extension and Stimulates cAMP Synthesis," *J. Biol. Chem.* 266: 13076-13079 (1991).

Jin et al., "Crystal Structure of Human Parathyroid Hormone 1-34 at 0.9-A Resolution," *J. Biol. Chem.* 275: 27238-27244 (2000).

Jing et al., "GDNF-Induced Activation of the Ret Protein Tyrosine Kinase Is Mediated by GDNFR-alpha, a Novel Receptor for GDNF," *Cell* 85: 1113-1124 (1996).

Jouishomme et al., "The Protein Kinase-C Activation Domain of the Parathyroid Hormone," *Endocrinology* 130: 53-60 (1992).

Kappel et al., "Regulating Gene Expression in Transgenic Animals," *Curr. Op. Biotechnol.* 3: 548-553 (1992).

Karaplis et al., "Lethal Skeletal Dysplasia From Targeted Disruption of the Parathyroid Hormone-Related Peptide Gene," *Genes Dev.* 8: 277-289 (1994).

Kaufman et al., "Transgenic Analysis of a 100-kb Human Beta-Globin Cluster-Containing DNA Fragment Propagated as a Bacterial Artificial Chromosome," *Blood* 94: 3178-3184 (1999).

Kaufmann et al., "Functional Expression of a Stably Transfected Parathyroid Hormone/Parathyroid Hormone Related Protein Receptor Complementary DNA in CHO cells," *Mot Cell. Endocrinol.* 104: 21-27 (1994).

Kemp et al., "Parathyroid Hormone-Related Protein of Malignancy: Active Synthetic Fragments," *Science* 238: 1568-1570 (1987).

Kimura et al., "Strategy for the Synthesis of Large Peptides: An Application to the Total Synthesis of Human Parathyroid Hormone [hPTH)1-84)]," *Biopolymers* 20: 1823-1832 (1981).

Kimura et al., "Discovery of a Novel Thrombopoietin Mimic Agonist Peptide," *J. Biochem.* 122: 1046-1051 (1997).

Klaus et al., "Investigation of the Solution Structure of the Human Parathyroid Hormone Fragment (1-34) by 1H NMR Spectroscopy, Distance Geometry, and Molecular Dynamics Calculations," *Biochemistry* 30: 6936-6942 (1991).

Kolakowski, "GCRDb: A G-Protein-Coupled Receptor Database," *Receptors and Channels* 2: 1-7 (1994).

Kronenberg et al., "The PTH/PTHrP Receptor: One Receptor for Two Ligands," in: *Molecular Genetics of Endocrine Disorders* (ed. R.V. Thakker), pp. 389-420 (Chapman & Hall, New York, NY, 1997).

Lanske et al., "PTH/PTHrP Receptor in Early Development and Indian Hedgehog-Regulated Bone Growth," *Science* 273: 663-666 (1996).

Li et al., "Minimization of a Polypeptide Hormone," *Science* 270: 1657-1660 (1995).

Lin et al., "Expression Cloning of an Adenylate Cyclase-Coupled Calcitonin Receptor," *Science* 254: 1022-1024 (1991).

Livnah et al., "Functional Mimicry of a Protein Hormone by a Peptide Agonist: The EPO Receptor Complex at 2.8 A," *Science* 273: 464-471 (1996).

Majeska et al., "Parathyroid Hormone-Responsive Clonal Cell Lines from Rat Osteosarcoma," *Endocrinology* 107: 1494-1503 (1980).

Matsumoto et al., "Daily Nasal Spray of hPTH(1-34) for 3 Months Increases Bone Mass in Osteoporotic Subjects: A Pilot Study," *Osteoporos. Int.* 17: 1532-1538 (2006).

McCuaig et al., "Molecular Cloning of the Gene Encoding the Mouse Parathyroid Hormone/Parathyroid Hormone-Related Peptide Receptor," *Proc. Natl. Acad. Sci. USA* 91: 5051-5055 (1994).

Menniti et al., "Different Modes of Regulation for Receptors Activating Phospholipase C in the Rat Pancreatoma Cell Line AR4-2J," *Mol. Pharmacol.* 40: 727-733 (1991).

Mickle et al., "Genotype-Phenotype Relationships in Cystic Fibrosis," *Med. Clin. North Am.* 84: 597-607 (2000).

Mikayama et al., "Molecular Cloning and Functional Expression of a cDNA Encoding Glycosylation-Inhibiting Factor," *Proc. Natl. Acad. Sci USA* 90: 10056-10060 (1993).

Mitchell et al., "Mechanisms of Homologous and Heterologous Regulation of Parathyroid Hormone Receptors in the Rat Osteosarcoma Cell Line UMR-106," *Endocrinology* 126: 2650-2660 (1990).

Mullins et al., "Perspective Series: Molecular Medicine in Genetically Engineered Animals," *J. Clin. Invest.* 98:S37-S40 (1996).

Murray et al., "Dexamethasone-Treated ROS 17/2.8 Rat Osteosarcoma Cells are Responsive to Human Carboxylterminal Parathyroid Hormone Peptide hPTH (53-84): Stimulation of Alkaline Phosphatase," *Calcif. Tissue Int.* 49: 120-123 (1991).

Musso et al. "Renal Vasodilatation and Microvessel Adenylate Cyclase Stimulation by Synthetic Parathyroid Hormone-Like Protein Fragments," *Eur. J. Pharmacol.* 174: 139-151 (1989).

Nakamoto et al., "Probing the Bimolecular Interactions of Parathyroid Hormone with the Human Parathyroid Hormone/Parathyroid Hormone-Related Protein Receptor. 1. Design, Synthesis and Characterization of Photoreactive Benzophenone-Containing Analogs of Parathyroid Hormone," *Biochemistry* 34: 10546-10552 (1995).

Nakamura et al., "Action of Fragments of Human Parathyroid Hormone on Blood Pressure in Rats," *Endocrinol. Jpn.* 28: 547-549 (1981).

Neugebauer et al., "Structural Elements of Human Parathyroid Hormone and their Possible Relation to Biological Activities," *Biochemistry* 31: 2056-2063 (1992).

Ngo et al., "Chapter 14: Computational Complexity, Protein Structure Prediction, and the Levinthal Paradox," in: *The Protein Folding Problem and Tertiary Structure Prediction* (eds. K.M. Merz et al.), pp. 492-495 (Birkhäuser Verlag, Boston, MA, 1995).

Nielsen et al., "Identification of Prokaryotic and Eukaryotic Signal Peptides and Prediction of their Cleavage Sites," *Prot. Eng.* 10:1-6 (1997).

Nissenson et al., "Synthetic Peptides Comprising the Amino-Terminal Sequence of a Parathyroid Hormone-Like Protein from Human Malignancies. Binding to Parathyroid Hormone Receptors and Activation of Adenylate Cyclase in Bone Cells and Kidney," *J. Biol. Chem.* 263: 12866-12871 (1988).

Oldenburg et al., "Conformational Studies on Analogs of Recombinant Parathyroid Hormone and their Interactions with Phospholipids," *J. Biol. Chem.* 271: 17582-17591 (1996).

Orkin et al., "Report and Recommendations of the Panel to Assess the NIH Investment in Research on Gene Therapy," available online at http://www.nih.gov/news/panelrep.html, pp. 1-39 (1995).

Pang et al., "Purification of Unique alpha Subunits of GTP-Binding Regulatory Proteins (G Proteins) by Affinity Chromatography with Immobilized beta gamma Subunits," *J. Biol. Chem.* 265: 18707-18712 (1990).

Parsons et al., "Pharmacology of Parathyroid Hormone and Some of its Fragments and Analogues," in: *Calcium-regulating hormones. Proceedings of the Fifth Parathyroid Conference*, Oxford, United Kingdom, Jul. 21-26, 1974 (eds. R.V. Talmage et al.), pp. 33-39 (Am. Elsevier Pub. Co., New York, NY, 1975).

Peggion et al., "Structure-Function Studies of Analogues of Parathyroid Hormone (PTH)-1-34 Containing Beta-Amino Acid Residues in Positions 11-13," *Biochemistry* 41: 8162-8175 (2002).

Pellegrini et al., "Addressing the Tertiary Structure of Human Parathyroid Hormone-(1-34)," *J. Biol. Chem.* 273: 10420-10427 (1998).

Pettit et al., "The Development of Site-Specific Drug-Delivery Systems for Protein and Peptide Biopharmaceuticals," *Trends Biotechnol.* 16: 343-349 (1998).

Phillips et al., "The Challenge of Gene Therapy and DNA Delivery," *J. Pharm. Pharmacol.* 53: 1169-1174 (2001).

Pines et al., "Generation and Characterization of Human Kidney Cell Lines Stably Expressing Recombinant Human PTH/PTHrP Receptor: Lack of Interaction with a C-Terminal Human PTH Peptide," *Endocrinology* 135: 1713-1716 (1994).

Pines et al., "Inositol 1-,4-,5-Trisphosphate-Dependent Ca2+ Signaling by the Recombinant Human PTH/PTHrP Receptor Stably Expressed in a Human Kidney Cell Line," *Bone* 18: 381-389 (1996).

Potts et al., "Parathyroid Hormone and Parathyroid Hormone-Related Peptide in Calcium Homeostasis, Bone Metabolism, and Bone Development: The Proteins, Their Genes, and Receptors," in: *Metabolic Bone Disease*, 3rd Edition (eds. L.V. Avioli et al.), pp. 51-94 (Acad. Press, San Diego, CA, 1998).

Ray et al., "NMR Solution Structure of the [Ala26]Parathyroid-Hormone-Related Protein(1-34) Expressed in Humoral Hypercalcemia of Malignancy," *Eur. J. Biochem.* 211: 205-211 (1993).

Reidhaar-Olson et al., "Active Variants of Human Parathyroid Hormone (1-34) with Multiple Amino Acid Substitutions," *Mol. Cell. Endocrinol.* 160: 135-147 (2000).

Rölz et al., "Characterization of the Molecular Motions of Constitutively Active G Protein-Coupled Receptors for Parathyroid Hormone," *Biophys, Chem.* 89: 119-128 (2001).

Romano et al., "Latest Developments in Gene Transfer Technology: Achievements, Perspectives, and Controversies over Therapeutic Applications," *Stem Cells* 18: 19-39 (2000).

Rosenblatt et al., "Design and Synthesis of Parathyroid Hormone Analogues of Enhanced Biological Activity," *Endocr. Res. Commun.* 4: 115-133 (1977).

Rosenblatt et al., "Identification of a Receptor-binding Region in Parathyroid Hormone," *Endocrinology* 107: 545-550 (1980).

Rosenblatt, "Parathyroid Hormone: Chemistry and Structure-Activity Relations," *Pathobiol. Annu.* 11: 53-86 (1981).

Rosol et al., "Sequences of the cDNAs Encoding Canine Parathyroid Hormone-Related Protein and Parathyroid Hormone," *Gene* 160: 241-243 (1995).

Rubin et al., "Molecular Cloning and Expression of Receptors for Parathyroid Hormone (PTH) and PTH-Related (PTHrP) Protein in Zebrafish," *Am. Zoologist* 36: 97A, Abstract No. 373 (1996).

Rubin et al., "Parathyroid Hormone (PTH)/PTH-Related (PTHRP) Receptor Cloning and in Situ Hybridization in the Zebrafish, Danio Rerio," *Am. Zoologist* 37: 181A, Abstract No. 651 (1997).

Rubin et al., "Molecular Cloning of a Zebrafish cDNA Encoding a Novel Parathyroid Hormone (PTH)/PTH-Related Protein (PTHrP) Receptor (PPR)," *Bone* 23: S255, Abstract No. T224 (1998).

Rubin et al., "Zebrafish Express the Common Parathyroid Hormone/Parathyroid Hormone-Related Peptide Receptor (PTH1R) and a Novel Receptor (PTH3R) that is Preferentially Activated by Mammalian and Fugufish Parathyroid Hormone-Related Peptide," *J. Biol. Chem.* 274: 28185-28190 (1999).

Sacchetti et al., "Green Fluorescent Protein Variants Fold Differentially in Prokaryotic and Eukaryotic Cells," *J. Cell. Biochem. Suppl.* 36: 117-128 (2001).

Sargent et al., "Membrane Lipid Phase as Catalyst for Peptide-Receptor Interactions," *Proc. Natl. Acad. Sci. USA* 83: 5774-5778 (1986).

Schipani et al., "A Constitutively Active Mutant PTH-PTHrP Receptor in Jansen-Type Metaphyseal Chondrodysplasia," *Science* 268: 98-100 (1995).

Schipani et al., "Pseudohypoparathyroidism Type Ib is not Caused by Mutations in the Coding Exons of the Human Parathyroid Hormone (PTH)/PTH-Related Peptide Receptor Gene," *J. Clin. Endocrinol. Metab.* 80: 1611-1621 (1995).

Segre et al., "Receptors for Secretin, Calcitonin, Parathyroid Hormone (PTH)/PTH-Related Peptide, Vasoactive Intestinal Peptide, Glucagonlike Peptide 1, Growth Hormone-Releasing Hormone, and Glucagon Belong to a Newly Discovered G-protein-Linked Receptor Family," *Trends Endocrinol. Metab.* 4: 309-314 (1993).

Shigeno et al., "Parathyroid Hormone Receptors are Plasma Membrane Glycoproteins with Asparagine-Linked Oligosaccharides," *J. Biol. Chem.* 263: 3872-3878 (1988).

Shimizu et al., "Residue 19 of the Parathyroid Hormone (PTH) Modulates Ligand Interaction with the Juxtamembrane Region of the PTH-1 Receptor," *Biochemistry* 41: 13224-13233 (2002).

Shimizu et al., "Amino-Terminal Parathyroid Hormone Fragment Analogs Containing α,α-di-alkyl Amino Acids at Positions 1 and 3," *J. Bone Miner. Res.* 19: 2078-2086 (2004).

Shimizu et al., "Novel Parathyroid Hormone (Pth) Antagonists that Bind to the Juxtamembrane Portion of the PTH/PTH-Related Protein Receptor," *J. Biol. Chem.* 280: 1797-1807 (2005).

Siegfried et al., "Parathyroid Hormone Stimulates Ecto-5'-Nucleotidase Activity in Renal Epithelial Cells: Role of Protein Kinase-C," *Endocrinology* 136:1267-1275 (1995).

Simon et al., "Diversity of G Proteins in Signal Transduction," *Science* 252: 802-808 (1991).

Skolnick et al., "From Genes to Protein Structure and Function: Novel Applications of Computational Approaches in the Genomic Era," *Trends Biotechnol.* 18: 34-39 (2000).

Smith et al., "The Challenges of Genome Sequence Annotation or "The devil is in the details"," *Nat. Biotechnol.* 15: 1222-1223 (1997).

Strathman et al., "G Protein Diversity: A Distinct Class of alpha Subunits is Present in Vertebrates and Invertebrates," *Proc. Natl. Acad. Sci, USA* 87: 9113-9117 (1990).

Strojek et al., "The Use of Transgenic Animal Techniques for Livestock Improvement," in: *Genetic Engineering: Principles and Methods*, vol. 10 (eds. J.K. Setlow et al.), pp. 221-246 (Plenum Press, New York, NY, 1988).

Stroop et al., "Chimeric Human Calcitonin and Glucagon Receptors Reveal Two Dissociable Calcitonin Interaction Sites," *Biochemistry* 34: 1050-1057 (1995).

Sunyaev et al., "From Analysis of Protein Structrual Alignments Toward a Novel Approach to Align Protein Sequences," *Proteins* 54: 569-582 (2004).

Szabo, "In Situ Hybridization," in: *Human Chromosomes: Manual of Basic Techniques* (eds. R.S. Verma et al.), pp. 152-165 (Pergamon Press, New York, NY,1989).

Takasu et al., "Human PTH/PTHrP Receptors and Type-2 PTH Receptos Show Discordant Selectivity for Human PTH Analogs with Amino-Terminal Modifications," *Bone* 23:S255, Abstract No. T223 (1998).

Takasu et al., "Phospholipase C Activation via the Human PTH/PTHrP Receptor Requires an Intact Amino-Terminus of Human PTH," *Bone* 23: S447, Abstract No. F148 (1998).

Tan et al., "Peptide Agonist Docking in the N-Terminal Ectodomain of a Class II G Protein-Coupled Receptor, the VPAC1 Receptor. Photoaffinity, NMR, and Molecular Modeling," *J. Biol. Chem.* 281: 12792-12798 (2006).

Treanor et al., "Characterization of a Multicomponent Receptor for GDNF," *Nature* 382: 80-83 (1996).

Tsomaia et al., "Cooperative Interaction of Arginine-19 and the N-Terminal Signaling Domain in the Affinity and Potency of Parathyroid Hormone," *Biochemistry* 43: 3459-3470 (2004).

Tsomaia et al., "Toward Parathyroid Hormone Minimization: Conformational Studies of Cyclic PTH(1-14) Analogues," *Biochemistry* 43: 690-699 (2004).

Turner et al., "A Putative Selectivity Filter in the G-Protein-Coupled Receptors for Parathyroid Hormone and Secretin," *J. Biol. Chem.* 271: 9205-9208 (1996).

Ullrich et al., "Signal Transduction by Receptors with Tyrosine Kinase Activity," *Cell* 61: 203-212 (1990).

Unson et al., "Characterization of Deletion and Truncation Mutants of the Rat Glucagon Receptor. Seven Transmembrane Segments are Necessary for Receptor Transport to the Plasma Membrane and Glucagon Binding," *J. Biol. Chem.* 270: 27720-27727 (1995).

Verma et al. "Gene Therapy- Promises, Problems and Prospects," *Nature* 389: 239-242 (1997).

Voet et al., "3. Chemical Evolution," in: *Biochemistry* (eds. D. Voet et al.), pp. 126-128 and 228-234 (Wiley, New York, NY, 1990).

Vogt et al., "An Assessment of Amino Acid Exchange Matrices in Aligning Protein Sequences: The Twilight Zone Revisited," *J. Mol. Biol.* 249: 816-831 (1995).

Wall, "Transgenic Livestock: Progress and Prospects for the Future," *Theriogenology* 45: 57-68 (1996).

Wang et al., "Rapid Analysis of Gene Expression (RAGE) Facilitates Universal Expression Profiling," *Nucleic Acids Res.* 27: 4609-4618 (1999).

Wells, "Additivity of Mutational Effects in Proteins," *Biochemistry* 29: 8509-8517 (1990).

Wells, "Hormone Mimicry," *Science* 273: 449-450 (1996).

Whitfield et al., "Small Bone-Building Fragments of Parathyroid Hormone: New Therapeutic Agents for Osteoporosis," *Trends Pharmacol. Sci.* 16: 382-386 (1995).

Wigley et al., "Site-Specific Transgene Insertion: An Approach," *Reprod. Fertil. Dev.* 6: 585-588 (1994).

Wittelsberger et al., "The Mid-Region of Parathyroid Hormone (1-34) Serves as a Functional Docking Domain in Receptor Activation," *Biochemistry* 45: 2027-2034 (2006).

Wrighton et al., "Small Peptides as Potent Mimetics of the Protein Hormone Erythropoietin," *Science* 273: 458-463 (1996).

Yamaguchi et al., "Parathyroid Hormone-Activated Calcium Channels in an Osteoblast-Like Clonal Osteosarcoma Cell Line: cAMP-Dependent and cAMP-Independent Calcium Channels," *J. Biol. Chem.* 262: 7711-7718 (1987).

Yamamoto et al., "Characterization and Agonist-Induced Down-Regulation of Parathyroid Hormone Receptors in Clonal Rat Osteosarcoma Cells," *Endocrinology* 122:1208-1217 (1988).

Yan et al., "Two-Amino Acid Molecular Switch in an Epithelial Morphogen that Regulates Binding to Two Distinct Receptors," *Science* 290: 523-527 (2000).

International Search Report for PCT/US03/08261 (mailed Oct. 24, 2003).

* cited by examiner

SEQUENCE LISTING

```
<160> NUMBER OF SEQ ID NOS: 52

<210> SEQ ID NO 1
<211> LENGTH: 14
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (1)..(1)
<223> OTHER INFORMATION: Xaa can represent an alpha helix stabilizing
      residue, Gly, Ser or Ala
<220> FEATURE:
<221> NAME/KEY: MISC_FEATURE
<222> LOCATION: (1)..(14)
<223> OTHER INFORMATION: At least one Xaa is an alpha helix stabilizing
      residue
<220> FEATURE:
<221> NAME/KEY: MISC_FEATURE
<222> LOCATION: (1)..(14)
<223> OTHER INFORMATION: At least one Xaa is 1 aminocyclopropane 1
      carboxylic acid, 1 amino cyclobutane carboxylic acid,
      1 aminocyclopentane 1 carboxylic acid,
      1 amino cyclohexane carboxylic acid or alpha, alpha diethylglycine
<220> FEATURE:
<221> NAME/KEY: MISC_FEATURE
<222> LOCATION: (1)..(14)
<223> OTHER INFORMATION: At least one Xaa is 1 aminocyclopropane 1
      carboxylic acid, 1 amino cyclobutane carboxylic acid,
      1 aminocyclopentane 1 carboxylic acid, 1 amino cyclohexane
      carboxylic acid or alpha, alpha diethylglycine
<220> FEATURE:
<221> NAME/KEY: MISC_FEATURE
<222> LOCATION: (3)..(3)
<223> OTHER INFORMATION: Xaa can represent an alpha helix stabilizing
      residue, Ala or Ser
<220> FEATURE:
<221> NAME/KEY: MISC_FEATURE
<222> LOCATION: (10)..(10)
<223> OTHER INFORMATION: Xaa can represent Ala, Gln or Asn
<220> FEATURE:
<221> NAME/KEY: MISC_FEATURE
<222> LOCATION: (11)..(11)
<223> OTHER INFORMATION: Xaa can represent Arg, Har or Leu
<220> FEATURE:
<221> NAME/KEY: MISC_FEATURE
```

```
<222> LOCATION: (12)..(12)
<223> OTHER INFORMATION: Xaa can represent alpha helix stabilizing
      residue, Ala or Gly
<220> FEATURE:
<221> NAME/KEY: MISC_FEATURE
<222> LOCATION: (13)..(13)
<223> OTHER INFORMATION: Xaa can represent alpha helix stabilizing
      residue or Lys
<220> FEATURE:
<221> NAME/KEY: MISC_FEATURE
<222> LOCATION: (14)..(14)
<223> OTHER INFORMATION: Xaa can represent alpha helix stabilizing
      residue, Trp or His
<220> FEATURE:
<221> NAME/KEY: MOD_RES
<222> LOCATION: (14)..(14)
<223> OTHER INFORMATION: AMIDATION

<400> SEQUENCE: 1

Xaa Val Xaa Glu Ile Gln Leu Met His Xaa Xaa Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (1)..(1)
<223> OTHER INFORMATION: Xaa can represent an alpha stabilizing residue,
      Gly, Ser or Ala
<220> FEATURE:
<221> NAME/KEY: MISC_FEATURE
<222> LOCATION: (1)..(3)
<223> OTHER INFORMATION: At least one Xaa is an alpha helix stabilizing
      residue
<220> FEATURE:
<221> NAME/KEY: MISC_FEATURE
<222> LOCATION: (1)..(3)
<223> OTHER INFORMATION: At least one Xaa is 1 aminocyclopropane 1
      carboxylic acid, 1 amino cyclobutane carboxylic acid,
      1 aminocyclopentane 1 carboxylic acid,
      1 amino cyclohexane carboxylic acid or alpha, alpha diethylglycine
<220> FEATURE:
<221> NAME/KEY: MISC_FEATURE
<222> LOCATION: (3)..(3)
<223> OTHER INFORMATION: Xaa can represent an alpha stabilizing residue,
      Ala or Ser
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 2

Xaa Val Xaa Glu Ile Gln Leu Met His Gln Xaa Ala Lys Trp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: [Aib 1,3, M]PTH(1 14)
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
```

```
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 3

Xaa Val Xaa Glu Ile Gln Leu Met His Gln Xaa Ala Lys Trp
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: [Ac5c 1, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 4

Xaa Val Ala Glu Ile Gln Leu Met His Gln Xaa Ala Lys Trp
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (1)..(1)
<223> OTHER INFORMATION: Xaa can represent an alpha helix stabilizing
      residue, Gly, Ser or Ala
<220> FEATURE:
<221> NAME/KEY: MISC_FEATURE
<222> LOCATION: (1)..(14)
<223> OTHER INFORMATION: At least one Xaa is an alpha helix stabilizing
      residue
<220> FEATURE:
<221> NAME/KEY: MISC_FEATURE
<222> LOCATION: (1)..(14)
<223> OTHER INFORMATION: At least one Xaa is 1 aminocyclopropane 1
      carboxylic acid, 1 amino cyclobutane carboxylic acid,
      1 aminocyclopentane 1 carboxylic acid, 1 amino cyclohexane
      carboxylic acid or alpha, alpha diethylglycine
<220> FEATURE:
<221> NAME/KEY: MISC_FEATURE
<222> LOCATION: (3)..(3)
<223> OTHER INFORMATION: Xaa can represent alpha helix stabilizing
      residue, Ala or Ser
<220> FEATURE:
<221> NAME/KEY: MISC_FEATURE
<222> LOCATION: (6)..(6)
<223> OTHER INFORMATION: Xaa can represent Ala, Gln or Asn
<220> FEATURE:
<221> NAME/KEY: MISC_FEATURE
<222> LOCATION: (10)..(10)
<223> OTHER INFORMATION: Xaa can represent Ala, Gln or Asn
```

```
<220> FEATURE:
<221> NAME/KEY: MISC_FEATURE
<222> LOCATION: (11)..(11)
<223> OTHER INFORMATION: Xaa can represent an alpha helix stabilizing
      residue, Har or Arg
<220> FEATURE:
<221> NAME/KEY: MISC_FEATURE
<222> LOCATION: (12)..(12)
<223> OTHER INFORMATION: Xaa can represent an alpha helix stabilizing
      residue or Lys
<220> FEATURE:
<221> NAME/KEY: MISC_FEATURE
<222> LOCATION: (14)..(14)
<223> OTHER INFORMATION: Xaa can represent an alpha helix stabilizing
      residue, Trp or His
<220> FEATURE:
<221> NAME/KEY: MOD_RES
<222> LOCATION: (14)..(14)
<223> OTHER INFORMATION: AMIDATION

<400> SEQUENCE: 5

Xaa Val Xaa Glu Ile Xaa Leu Met His Xaa Xaa Xaa Lys Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Mutated hPTH
<220> FEATURE:
<221> NAME/KEY: MISC_FEATURE
<222> LOCATION: (1)..(1)
<223> OTHER INFORMATION: Xaa can represent an alpha helix stabilizing
      residue, Gly, Ser or Ala
<220> FEATURE:
<221> NAME/KEY: MISC_FEATURE
<222> LOCATION: (1)..(14)
<223> OTHER INFORMATION: At least one Xaa is 1 aminocyclopropane 1
      carboxylic acid, 1 amino cyclobutane carboxylic acid,
      1 aminocyclopentane 1 carboxylic acid, 1 amino cyclohexane
      carboxylic acid or alpha, alpha diethylglycine
<220> FEATURE:
<221> NAME/KEY: MISC_FEATURE
<222> LOCATION: (3)..(3)
<223> OTHER INFORMATION: Xaa can represent an alpha helix stabilizing
      residue, Ala or Ser
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 6

Xaa Val Xaa Glu Ile Gln Leu Met His Gln Xaa Ala Lys Trp
1               5                   10

<210> SEQ ID NO 7
<211> LENGTH: 14
<212> TYPE: PRT
<213> ORGANISM: Artificial Sequence
<220> FEATURE:
<223> OTHER INFORMATION: [Ac4c 1, Aib 3, M]PTH(1 14)
<220> FEATURE:
<221> NAME/KEY: MISC_FEATURE
<222> LOCATION: (1)..(1)
<223> OTHER INFORMATION: Xaa represents 1 amino cyclobutane carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
```

```
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 7

Xaa Val Xaa Glu Ile Gln Leu Met His Gln Xaa Ala Lys Trp
1               5                   10

<210> SEQ ID NO 8
<211> LENGTH: 14
<212> TYPE: PRT
<213> ORGANISM: Artificial Sequence
<220> FEATURE:
<223> OTHER INFORMATION: [Ac6c 1, Aib 3, M]PTH(1 14)
<220> FEATURE:
<221> NAME/KEY: MISC_FEATURE
<222> LOCATION: (1)..(1)
<223> OTHER INFORMATION: Xaa represents 1 amino cyclohexane carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 8

Xaa Val Xaa Glu Ile Gln Leu Met His Gln Xaa Ala Lys Trp
1               5                   10

<210> SEQ ID NO 9
<211> LENGTH: 14
<212> TYPE: PRT
<213> ORGANISM: Artificial Sequence
<220> FEATURE:
<223> OTHER INFORMATION: [Ac5c 1, Ac4c 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents 1 amino cyclobutane carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 9

Xaa Val Xaa Glu Ile Gln Leu Met His Gln Xaa Ala Lys Trp
1               5                   10

<210> SEQ ID NO 10
<211> LENGTH: 14
<212> TYPE: PRT
```

<213> ORGANISM: Artificial Sequence
<220> FEATURE:
<223> OTHER INFORMATION: [Ac5c 1, Ac6c 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents 1 amino cyclohexane carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 10

Xaa Val Xaa Glu Ile Gln Leu Met His Gln Xaa Ala Lys Trp
1               5                   10

<210> SEQ ID NO 11
<211> LENGTH: 14
<212> TYPE: PRT
<213> ORGANISM: Artificial Sequence
<220> FEATURE:
<223> OTHER INFORMATION: [Ac4c 1,3, M]PTH(1 14)
<220> FEATURE:
<221> NAME/KEY: MISC_FEATURE
<222> LOCATION: (1)..(1)
<223> OTHER INFORMATION: Xaa represents 1 amino cyclobutane carboxylic
      acid
<220> FEATURE:
<221> NAME/KEY: MISC_FEATURE
<222> LOCATION: (3)..(3)
<223> OTHER INFORMATION: Xaa represents 1 amino cyclobutane carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 11

Xaa Val Xaa Glu Ile Gln Leu Met His Gln Xaa Ala Lys Trp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: [Ac6c 1,3, M]PTH(1 14)
<220> FEATURE:
<221> NAME/KEY: MISC_FEATURE
<222> LOCATION: (1)..(1)
<223> OTHER INFORMATION: Xaa represents 1 amino cyclohexane carboxylic
      acid
<220> FEATURE:
<221> NAME/KEY: MISC_FEATURE
<222> LOCATION: (3)..(3)
<223> OTHER INFORMATION: Xaa represents 1 amino cyclohexane carboxylic
      acid
<220> FEATURE:
<221> NAME/KEY: MISC_FEATURE
<222> LOCATION: (11)..(11)
<223> OTHER INFORMATION: Xaa represents homoarginine

```
<220> FEATURE:
<221> NAME/KEY: MOD_RES
<222> LOCATION: (14)..(14)
<223> OTHER INFORMATION: AMIDATION

<400> SEQUENCE: 12

Xaa Val Xaa Glu Ile Gln Leu Met His Gln Xaa Ala Lys Trp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: [M]PTH(1 14)
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 13

Ala Val Ala Glu Ile Gln Leu Met His Gln Xaa Ala Lys Trp
1               5                   10

<210> SEQ ID NO 14
<211> LENGTH: 34
<212> TYPE: PRT
<213> ORGANISM: Artificial Sequence
<220> FEATURE:
<223> OTHER INFORMATION: [Nle 8,21, Tyr 34]rPTH(1 34)amide
<220> FEATURE:
<221> NAME/KEY: MISC_FEATURE
<222> LOCATION: (8)..(8)
<223> OTHER INFORMATION: Xaa represents Norleucine
<220> FEATURE:
<221> NAME/KEY: MISC_FEATURE
<222> LOCATION: (21)..(21)
<223> OTHER INFORMATION: Xaa represents Norleucine
<220> FEATURE:
<221> NAME/KEY: MOD_RES
<222> LOCATION: (34)..(34)
<223> OTHER INFORMATION: AMIDATION

<400> SEQUENCE: 14

Ala Val Ser Glu Ile Gln Leu Xaa His Asn Leu Gly Lys His Leu Ala
1               5                   10                  15

Ser Val Glu Arg Xaa Gln Trp Leu Arg Lys Lys Leu Gln Asp Val His
            20                  25                  30

Asn Tyr

<210> SEQ ID NO 15
<211> LENGTH: 14
<212> TYPE: PRT
<213> ORGANISM: Artificial Sequence
<220> FEATURE:
<223> OTHER INFORMATION: [Ac5c 1, Aib 3, M]PTH(1 14)amide
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
```

```
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 15

Xaa Val Xaa Glu Ile Gln Leu Met His Gln Xaa Ala Lys Trp
1               5                   10

<210> SEQ ID NO 16
<211> LENGTH: 11
<212> TYPE: PRT
<213> ORGANISM: Artificial Sequence
<220> FEATURE:
<223> OTHER INFORMATION: [Ala 1,3, Gln 10, Har 11]PTH(1 11)amide
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (11)..(11)
<223> OTHER INFORMATION: AMIDATION

<400> SEQUENCE: 16

Ala Val Ala Glu Ile Gln Leu Met His Gln Xaa
1               5                   10

<210> SEQ ID NO 17
<211> LENGTH: 14
<212> TYPE: PRT
<213> ORGANISM: Rattus sp.
<220> FEATURE:
<221> NAME/KEY: MOD_RES
<222> LOCATION: (14)..(14)
<223> OTHER INFORMATION: AMIDATION

<400> SEQUENCE: 17

Ala Val Ser Glu Ile Gln Leu Met His Asn Leu Gly Lys His
1               5                   10

<210> SEQ ID NO 18
<211> LENGTH: 84
<212> TYPE: PRT
<213> ORGANISM: Homo sapiens
<220> FEATURE:
<221> NAME/KEY: MOD_RES
<222> LOCATION: (84)..(84)
<223> OTHER INFORMATION: AMIDATION

<400> SEQUENCE: 18

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 19
```

```
<211> LENGTH: 34
<212> TYPE: PRT
<213> ORGANISM: Homo sapiens
<220> FEATURE:
<221> NAME/KEY: MOD_RES
<222> LOCATION: (34)..(34)
<223> OTHER INFORMATION: AMIDATION

<400> SEQUENCE: 19

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 20
<211> LENGTH: 21
<212> TYPE: PRT
<213> ORGANISM: Artificial Sequence
<220> FEATURE:
<223> OTHER INFORMATION: [M]PTH(1 21)
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 20

Ala Val Ala Glu Ile Gln Leu Met His Gln Xaa Ala Lys Trp Leu Asn
1               5                   10                  15

Ser Met Glu Arg Val
            20

<210> SEQ ID NO 21
<211> LENGTH: 21
<212> TYPE: PRT
<213> ORGANISM: Artificial Sequence
<220> FEATURE:
<223> OTHER INFORMATION: [Aib 1,3, M]PTH(1 21)
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION

<400> SEQUENCE: 21

Xaa Val Xaa Glu Ile Gln Leu Met His Gln Xaa Ala Lys Trp Leu Asn
1               5                   10                  15

Ser Met Glu Arg Val
            20

<210> SEQ ID NO 22
<211> LENGTH: 10
<212> TYPE: PRT
<213> ORGANISM: Artificial Sequence
```

```
<220> FEATURE:
<223> OTHER INFORMATION: [Ac5c 1, Aib 3, Gln 10]PTH(1 10)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MOD_RES
<222> LOCATION: (10)..(10)
<223> OTHER INFORMATION: AMIDATION

<400> SEQUENCE: 22

Xaa Val Xaa Glu Ile Gln Leu Met His Gln
1               5                   10

<210> SEQ ID NO 23
<211> LENGTH: 14
<212> TYPE: PRT
<213> ORGANISM: Artificial Sequence
<220> FEATURE:
<223> OTHER INFORMATION: [Ac5c 1, Trp 2, Aib 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 23

Xaa Trp Xaa Glu Ile Gln Leu Met His Gln Xaa Ala Lys Trp
1               5                   10

<210> SEQ ID NO 24
<211> LENGTH: 14
<212> TYPE: PRT
<213> ORGANISM: Artificial Sequence
<220> FEATURE:
<223> OTHER INFORMATION: [Deg 1, M]PTH(1 14)
<220> FEATURE:
<221> NAME/KEY: MISC_FEATURE
<222> LOCATION: (1)..(1)
<223> OTHER INFORMATION: Xaa represents alpha, alpha diethylglycine
<220> FEATURE:
<221> NAME/KEY: MISC_FEATURE
<222> LOCATION: (11)..(11)
<223> OTHER INFORMATION: Xaa represents homoarginine

<400> SEQUENCE: 24

Xaa Val Ala Glu Ile Gln Leu Met His Gln Xaa Ala Lys Trp
1               5                   10

<210> SEQ ID NO 25
<211> LENGTH: 14
<212> TYPE: PRT
<213> ORGANISM: Artificial Sequence
<220> FEATURE:
<223> OTHER INFORMATION: [Ac3c 1, M]PTH(1 14)
```

```
<220> FEATURE:
<221> NAME/KEY: MISC_FEATURE
<222> LOCATION: (1)..(1)
<223> OTHER INFORMATION: Xaa represents 1 aminocyclopropane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 25

Xaa Val Ala Glu Ile Gln Leu Met His Gln Xaa Ala Lys Trp
1               5                   10

<210> SEQ ID NO 26
<211> LENGTH: 14
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: AMIDATION

<400> SEQUENCE: 26

Ser Val Ser Glu Ile Gln Leu Met His Asn Leu Gly Lys His
1               5                   10

<210> SEQ ID NO 27
<211> LENGTH: 14
<212> TYPE: PRT
<213> ORGANISM: Artificial Sequence
<220> FEATURE:
<223> OTHER INFORMATION: [Deg 1,3, M]PTH(1 14)
<220> FEATURE:
<221> NAME/KEY: MISC_FEATURE
<222> LOCATION: (1)..(1)
<223> OTHER INFORMATION: Xaa represents alpha, alpha diethylglycine
<220> FEATURE:
<221> NAME/KEY: MISC_FEATURE
<222> LOCATION: (3)..(3)
<223> OTHER INFORMATION: Xaa represents alpha, alpha diethylglycine
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 27

Xaa Val Xaa Glu Ile Gln Leu Met His Gln Xaa Ala Lys Trp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: [Ac3c 1,3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopropane 1 carboxylic
      acid
<220> FEATURE:
<221> NAME/KEY: MISC_FEATURE
<222> LOCATION: (3)..(3)
<223> OTHER INFORMATION: Xaa represents 1 aminocyclopropane 1 carboxylic
```

```
                            acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 28

Xaa Val Xaa Glu Ile Gln Leu Met His Gln Xaa Ala Lys Trp
1               5                   10

<210> SEQ ID NO 29
<211> LENGTH: 14
<212> TYPE: PRT
<213> ORGANISM: Artificial Sequence
<220> FEATURE:
<223> OTHER INFORMATION: [Ac5c 1,3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents 1 aminocyclopentane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 29

Xaa Val Xaa Glu Ile Gln Leu Met His Gln Xaa Ala Lys Trp
1               5                   10

<210> SEQ ID NO 30
<211> LENGTH: 14
<212> TYPE: PRT
<213> ORGANISM: Artificial Sequence
<220> FEATURE:
<223> OTHER INFORMATION: [Ac5c 1, Aib 3, Gln 10, Ala 12,
      Trp 14]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MOD_RES
<222> LOCATION: (14)..(14)
<223> OTHER INFORMATION: AMIDATION

<400> SEQUENCE: 30

Xaa Val Xaa Glu Ile Gln Leu Met His Gln Arg Ala Lys Trp
1               5                   10

<210> SEQ ID NO 31
<211> LENGTH: 9
<212> TYPE: PRT
<213> ORGANISM: Artificial Sequence
<220> FEATURE:
```

```
<223> OTHER INFORMATION: [Ac5c 1, Aib 3, M]PTH(1 9)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MOD_RES
<222> LOCATION: (9)..(9)
<223> OTHER INFORMATION: AMIDATION

<400> SEQUENCE: 31

Xaa Val Xaa Glu Ile Gln Leu Met His
1               5

<210> SEQ ID NO 32
<211> LENGTH: 14
<212> TYPE: PRT
<213> ORGANISM: Artificial Sequence
<220> FEATURE:
<223> OTHER INFORMATION: [Aib 1, Ac5c 3]PTH(1 14)
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents 1 aminocyclopentane 1 carboxylic
      acid
<220> FEATURE:
<221> NAME/KEY: MOD_RES
<222> LOCATION: (14)..(14)
<223> OTHER INFORMATION: AMIDATION

<400> SEQUENCE: 32

Xaa Val Xaa Glu Ile Gln Leu Met His Asn Leu Gly Lys His
1               5                   10

<210> SEQ ID NO 33
<211> LENGTH: 9
<212> TYPE: PRT
<213> ORGANISM: Artificial Sequence
<220> FEATURE:
<223> OTHER INFORMATION: native hPTH(1 9)amide
<220> FEATURE:
<221> NAME/KEY: MOD_RES
<222> LOCATION: (9)..(9)
<223> OTHER INFORMATION: AMIDATION

<400> SEQUENCE: 33

Ser Val Ser Glu Ile Gln Leu Met His
1               5

<210> SEQ ID NO 34
<211> LENGTH: 9
<212> TYPE: PRT
<213> ORGANISM: Artificial Sequence
<220> FEATURE:
<223> OTHER INFORMATION: [Aib 1,3]PTH(1 9)amide
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
```

```
<221> NAME/KEY: MOD_RES
<222> LOCATION: (9)..(9)
<223> OTHER INFORMATION: AMIDATION

<400> SEQUENCE: 34

Xaa Val Xaa Glu Ile Gln Leu Met His
1               5

<210> SEQ ID NO 35
<211> LENGTH: 10
<212> TYPE: PRT
<213> ORGANISM: Artificial Sequence
<220> FEATURE:
<223> OTHER INFORMATION: [Aib 1,3, Gln 10]PTH(1 10)amide
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MOD_RES
<222> LOCATION: (10)..(10)
<223> OTHER INFORMATION: AMIDATION

<400> SEQUENCE: 35

Xaa Val Xaa Glu Ile Gln Leu Met His Gln
1               5                   10

<210> SEQ ID NO 36
<211> LENGTH: 21
<212> TYPE: PRT
<213> ORGANISM: Artificial Sequence
<220> FEATURE:
<223> OTHER INFORMATION: [Aib 1,3, Nle 8, Gln 10, Har 11, Ala 12,
      Trp 14, Arg 19, Tyr 21]rPTH(1 21)amide radiolabeled with Iodine
      isotope 125
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (8)..(8)
<223> OTHER INFORMATION: Xaa represents norleucine
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (21)..(21)
<223> OTHER INFORMATION: AMIDATION
<220> FEATURE:
<221> NAME/KEY: MISC_FEATURE
<222> LOCATION: (21)..(21)
<223> OTHER INFORMATION: Radiolabeled with Iodine isotope 125

<400> SEQUENCE: 36

Xaa Val Xaa Glu Ile Gln Leu Xaa His Gln Xaa Ala Lys Trp Leu Ala
1               5                   10                  15

Ser Val Arg Arg Tyr
            20

<210> SEQ ID NO 37
<211> LENGTH: 14
```

```
<212> TYPE: PRT
<213> ORGANISM: Artificial Sequence
<220> FEATURE:
<223> OTHER INFORMATION: [Deg 3, M]PTH(1 14)
<220> FEATURE:
<221> NAME/KEY: MISC_FEATURE
<222> LOCATION: (3)..(3)
<223> OTHER INFORMATION: Xaa represents alpha, alpha diethylglycine
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 37

Ala Val Xaa Glu Ile Gln Leu Met His Gln Xaa Ala Lys Trp
1               5                   10

<210> SEQ ID NO 38
<211> LENGTH: 14
<212> TYPE: PRT
<213> ORGANISM: Artificial Sequence
<220> FEATURE:
<223> OTHER INFORMATION: [Ac3c 3, M]PTH(1 14)
<220> FEATURE:
<221> NAME/KEY: MISC_FEATURE
<222> LOCATION: (3)..(3)
<223> OTHER INFORMATION: Xaa represents 1 aminocyclopropane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 38

Ala Val Xaa Glu Ile Gln Leu Met His Gln Xaa Ala Lys Trp
1               5                   10

<210> SEQ ID NO 39
<211> LENGTH: 14
<212> TYPE: PRT
<213> ORGANISM: Artificial Sequence
<220> FEATURE:
<223> OTHER INFORMATION: [Ac5c 3, M]PTH(1 14)
<220> FEATURE:
<221> NAME/KEY: MISC_FEATURE
<222> LOCATION: (3)..(3)
<223> OTHER INFORMATION: Xaa represents 1 aminocyclopentane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 39

Ala Val Xaa Glu Ile Gln Leu Met His Gln Xaa Ala Lys Trp
1               5                   10

<210> SEQ ID NO 40
<211> LENGTH: 14
<212> TYPE: PRT
<213> ORGANISM: Artificial Sequence
```

```
<220> FEATURE:
<223> OTHER INFORMATION: [Deg 1, Ac3c 3, M]PTH(1 14)
<220> FEATURE:
<221> NAME/KEY: MISC_FEATURE
<222> LOCATION: (1)..(1)
<223> OTHER INFORMATION: Xaa represents alpha, alpha diethylglycine
<220> FEATURE:
<221> NAME/KEY: MISC_FEATURE
<222> LOCATION: (3)..(3)
<223> OTHER INFORMATION: Xaa represents 1 aminocyclopropane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 40

Xaa Val Xaa Glu Ile Gln Leu Met His Gln Xaa Ala Lys Trp
1               5                   10

<210> SEQ ID NO 41
<211> LENGTH: 14
<212> TYPE: PRT
<213> ORGANISM: Artificial Sequence
<220> FEATURE:
<223> OTHER INFORMATION: [Deg 1, Ac5c 3, M]PTH(1 14)
<220> FEATURE:
<221> NAME/KEY: MISC_FEATURE
<222> LOCATION: (1)..(1)
<223> OTHER INFORMATION: Xaa represents alpha, alpha diethylglycine
<220> FEATURE:
<221> NAME/KEY: MISC_FEATURE
<222> LOCATION: (3)..(3)
<223> OTHER INFORMATION: Xaa represents 1 aminocyclopentane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 41

Xaa Val Xaa Glu Ile Gln Leu Met His Gln Xaa Ala Lys Trp
1               5                   10

<210> SEQ ID NO 42
<211> LENGTH: 14
<212> TYPE: PRT
<213> ORGANISM: Artificial Sequence
<220> FEATURE:
<223> OTHER INFORMATION: [Deg 1, Aib 3, M]PTH(1 14)
<220> FEATURE:
<221> NAME/KEY: MISC_FEATURE
<222> LOCATION: (1)..(1)
<223> OTHER INFORMATION: Xaa represents alpha, alpha diethylglycine
<220> FEATURE:
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION
```

```
<400> SEQUENCE: 42

Xaa Val Xaa Glu Ile Gln Leu Met His Gln Xaa Ala Lys Trp
1               5                   10

<210> SEQ ID NO 43
<211> LENGTH: 14
<212> TYPE: PRT
<213> ORGANISM: Artificial Sequence
<220> FEATURE:
<223> OTHER INFORMATION: [Ac3c 1, Deg 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopropane 1 carboxylic
      acid
<220> FEATURE:
<221> NAME/KEY: MISC_FEATURE
<222> LOCATION: (3)..(3)
<223> OTHER INFORMATION: Xaa represents alpha, alpha diethylglycine
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 43

Xaa Val Xaa Glu Ile Gln Leu Met His Gln Xaa Ala Lys Trp
1               5                   10

<210> SEQ ID NO 44
<211> LENGTH: 14
<212> TYPE: PRT
<213> ORGANISM: Artificial Sequence
<220> FEATURE:
<223> OTHER INFORMATION: [Ac3c 1, Ac5c 3, M]PTH(1 14)
<220> FEATURE:
<221> NAME/KEY: MISC_FEATURE
<222> LOCATION: (1)..(1)
<223> OTHER INFORMATION: Xaa represents 1 amino cyclopropane 1
      carboxylic acid
<220> FEATURE:
<221> NAME/KEY: MISC_FEATURE
<222> LOCATION: (3)..(3)
<223> OTHER INFORMATION: Xaa represents 1 amino cyclopentane 1
      carboxylic acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 44

Xaa Val Xaa Glu Ile Gln Leu Met His Gln Xaa Ala Lys Trp
1               5                   10

<210> SEQ ID NO 45
<211> LENGTH: 14
<212> TYPE: PRT
<213> ORGANISM: Artificial Sequence
<220> FEATURE:
<223> OTHER INFORMATION: [Ac3c 1, Aib 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopropane 1 carboxylic
      acid
<220> FEATURE:
```

```
<221> NAME/KEY: MISC_FEATURE
<222> LOCATION: (3)..(3)
<223> OTHER INFORMATION: Xaa represents alpha aminoisobutyric acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 45

Xaa Val Xaa Glu Ile Gln Leu Met His Gln Xaa Ala Lys Trp
1               5                   10

<210> SEQ ID NO 46
<211> LENGTH: 14
<212> TYPE: PRT
<213> ORGANISM: Artificial Sequence
<220> FEATURE:
<223> OTHER INFORMATION: [Ac5c 1, Deg 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents alpha, alpha diethylglycine
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MISC_FEATURE
<222> LOCATION: (51)..(51)
<223> OTHER INFORMATION: Xaa represents homoarginine

<400> SEQUENCE: 46

Xaa Val Xaa Glu Ile Gln Leu Met His Gln Xaa Ala Lys Trp
1               5                   10

<210> SEQ ID NO 47
<211> LENGTH: 14
<212> TYPE: PRT
<213> ORGANISM: Artificial Sequence
<220> FEATURE:
<223> OTHER INFORMATION: [Ac5c 1, Ac3c 3, M]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (3)..(3)
<223> OTHER INFORMATION: Xaa represents 1 aminocyclopropane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 47

Xaa Val Xaa Glu Ile Gln Leu Met His Gln Xaa Ala Lys Trp
1               5                   10
```

```
<210> SEQ ID NO 48
<211> LENGTH: 14
<212> TYPE: PRT
<213> ORGANISM: Artificial Sequence
<220> FEATURE:
<223> OTHER INFORMATION: [Aib 1, Deg 3, M]PTH(1 14)
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents alpha, alpha diethylglycine
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 48

Xaa Val Xaa Glu Ile Gln Leu Met His Gln Xaa Ala Lys Trp
 1               5                  10

<210> SEQ ID NO 49
<211> LENGTH: 14
<212> TYPE: PRT
<213> ORGANISM: Artificial Sequence
<220> FEATURE:
<223> OTHER INFORMATION: [Aib 1, Ac3c 3, M]PTH(1 14)
<220> FEATURE:
<221> NAME/KEY: MISC_FEATURE
<222> LOCATION: (1)..(1)
<223> OTHER INFORMATION: Xaa represents alpha aminoisobutyric acid
<220> FEATURE:
<221> NAME/KEY: MISC_FEATURE
<222> LOCATION: (3)..(3)
<223> OTHER INFORMATION: Xaa represents 1 aminocyclopropane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 49

Xaa Val Xaa Glu Ile Gln Leu Met His Gln Xaa Ala Lys Trp
 1               5                  10

<210> SEQ ID NO 50
<211> LENGTH: 14
<212> TYPE: PRT
<213> ORGANISM: Artificial Sequence
<220> FEATURE:
<223> OTHER INFORMATION: [Aib 1, Ac5c 3]PTH(1 14)
<220> FEATURE:
<221> NAME/KEY: MISC_FEATURE
<222> LOCATION: (1)..(1)
<223> OTHER INFORMATION: Xaa represents alpha aminosiobutyric acid
<220> FEATURE:
<221> NAME/KEY: MISC_FEATURE
<222> LOCATION: (3)..(3)
<223> OTHER INFORMATION: Xaa represents 1 aminocyclopentane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
```

```
<221> NAME/KEY: MOD_RES
<222> LOCATION: (14)..(14)
<223> OTHER INFORMATION: AMIDATION

<400> SEQUENCE: 50

Xaa Val Xaa Glu Ile Gln Leu Met His Gln Xaa Ala Lys Trp
1               5                   10

<210> SEQ ID NO 51
<211> LENGTH: 14
<212> TYPE: PRT
<213> ORGANISM: Artificial Sequence
<220> FEATURE:
<223> OTHER INFORMATION: [Ac5c 1, Gln 10, Har 11, Ala 12,
      Trp 14]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MISC_FEATURE
<222> LOCATION: (11)..(11)
<223> OTHER INFORMATION: Xaa represents homoarginine
<220> FEATURE:
<221> NAME/KEY: MOD_RES
<222> LOCATION: (14)..(14)
<223> OTHER INFORMATION: AMIDATION

<400> SEQUENCE: 51

Xaa Val Ser Glu Ile Gln Leu Met His Gln Xaa Ala Lys Trp
1               5                   10

<210> SEQ ID NO 52
<211> LENGTH: 14
<212> TYPE: PRT
<213> ORGANISM: Artificial Sequence
<220> FEATURE:
<223> OTHER INFORMATION: [Ac5c 1]PTH(1 14)
<220> FEATURE:
<221> NAME/KEY: MISC_FEATURE
<222> LOCATION: (1)..(1)
<223> OTHER INFORMATION: Xaa represents 1 aminocyclopentane 1 carboxylic
      acid
<220> FEATURE:
<221> NAME/KEY: MOD_RES
<222> LOCATION: (14)..(14)
<223> OTHER INFORMATION: AMIDATION

<400> SEQUENCE: 52

Xaa Val Ser Glu Ile Gln Leu Met His Asn Leu Gly Lys His
1               5                   10
```

CONFORMATIONALLY CONSTRAINED PARATHYROID HORMONES WITH ALPHA-HELIX STABILIZERS

STATEMENT REGARDING FEDERALLY-SPONSORED RESEARCH AND DEVELOPMENT

Statement under MPEP 310. The U.S. Government has a paid-up license in this invention and the right in limited circumstances to require the patent owner to license others on reasonable terms as provided for by the terms of Grant No. DK-11794 awarded by the National Institute of Health.

CROSS-REFERENCE TO RELATED APPLICATIONS

This application is a national phase of International Appl. No. PCT/US2003/008261, filed Mar. 19, 2003, which published under PCT Article 21(2) in English and which is herein incorporated by reference.

BACKGROUND OF THE INVENTION

1. Field of the Invention

The present invention relates to conformationally constrained parathyroid hormone (PTH) analogs, and methods of preparing and using the PTH analogs.

2. Background Art

Parathyroid Hormone

Parathyroid hormone (PTH), an 84 amino acid peptide, is the principal regulator of ionized blood calcium in the human body (Kronenberg, H. M., et al., In *Handbook of Experimental Pharmacology*, Mundy, G. R., and Martin, T. J., (eds), pp. 185-201, Springer-Verlag, Heidelberg (1993)). Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH is thought to exert these effects primarily through receptor-mediated activation of adenylate cyclase and/or phospholipase C.

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcemia, humoral hypercalcemia of malignancy (HHM) is the most common paraneoplastic syndrome. It appears to result in most instances from the production by tumors (e.g., squamous, renal, ovarian, or bladder carcinomas) of a class of protein hormone which shares amino acid homology with PTH. These PTH-related proteins (PTHrP) appear to mimic certain of the renal and skeletal actions of PTH and are believed to interact with the PTH receptor in these tissues.

Osteoporosis

Osteoporosis is a potentially crippling skeletal disease observed in a substantial portion of the senior adult population, in pregnant women and even in juveniles. The term osteoporosis refers to a heterogeneous group of disorders. Clinically, osteoporosis is separated into type I and type II. Type I osteoporosis occurs predominantly in middle aged women and is associated with estrogen loss at menopause, while osteoporosis type II is associated with advancing age. Patients with osteoporosis would benefit from new therapies designed to promote fracture repair, or from therapies designed to prevent or lessen the fractures associated with the disease.

The disease is marked by diminished bone mass, decreased bone mineral density (BMD), decreased bone strength and an increased risk of bone fracture. At present, there is no effective cure for osteoporosis, though estrogen, calcitonin and the bisphosphonates, etidronate and alendronate are used to treat the disease with varying levels of success. These agents act to decrease bone resorption. Since parathyroid hormone regulates blood calcium and the phosphate levels, and has potent anabolic (bone-forming) effects on the skeleton, in animals (Shen, V., et al., *Calcif. Tissue Int.* 50:214-220 (1992); Whitefild, J. F., et al., *Calcif. Tissue Int.* 56:227-231 (1995) and Whitfield, J. F., et al., *Calcif Tissue Int.* 60:26-29 (1997)) and humans (Slovik, D. M., et al., *J. Bone Miner. Res.* 1:377-381 (1986); Dempster, D. W., et al., *Endocr. Rev.* 14:690-709 (1993) and Dempster, D. W., et al., *Endocr. Rev.* 15:261 (1994)) when administered intermittently, PTH, or PTH derivatives, are prime candidates for new and effective therapies for osteoporosis.

PTH Derivatives

PTH derivatives include polypeptides that have amino acid substitutions or are truncated relative to the full length molecule. Both a 14 and a 34 amino acid amino-terminal truncated form of PTH, as well as a C-terminal truncated form have been studied. Additionally, amino acid substitutions within the truncated polypeptides have also been investigated.

Synthetic PTH(1-34) exhibits full bioactivity in most cell-based assay systems, has potent anabolic effects on bone mass in animals and has been shown to reduce the risk of bone fracture in postmenopausal osteoporotic women (Neer, R. M., et al., *N.E.J.M.* 344:1434-1441 (2001); Dempster, D. W., et al., *Endocr Rev* 14:690-709 (1993)). PTH acts on the PTH/PTHrP receptor P1R), a class II G protein-coupled heptahelical receptor that couples to the adenylyl cyclase/cAMP and phospolipase C/inositol phosphate (IP) signaling pathway (Rippner, H., et al., *Science* 254:1024-1026 (1991)). Deletion analysis studies have shown that the amino-terminal residues of PTH play a crucial role in stimulating the P1R to activate the cAMP and IP signaling pathways (Tregear, G. W., et al., *Endocrinology* 93:1349-1353 (1973); Takasu, H., et al., *Biochemistry* 38:13453-13460 (1999)). Crosslinking and receptor mutagenesis studies have indicated that residues in the amino-terminal portion of PTH interact with the extracellular loops and extracellular ends of the seven transmembrane helices, which reside within the juxtamembrane region of the receptor (Bergwitz, C., et al., *J. Biol. Chem.* 271:26469-26472 (1996); Hoare, S. R. J., et al., *J. Biol. Chem* 276:7741-7753 (2001); Behar, V., et al., *J. Biol. Chem.* 275:9-17 (1999);

Shimizu, M., et al., *J. Biol. Chem.* 275:19456-19460 (2000); Luck, M. D., et al., *Molecular Endocrinology* 13:670-680 (1999)).

α-Helix Stabilizers

The first 34 amino acids of PTH and PTHrP contain sufficient information for high affinity P1R binding and potent induction of P1R-mediated signaling responses (Neer, R M, et al., *N.E.J.M.* 344: 1434-1441 (2001)). Short N-terminal fragments of PTH, such as PTH(1-14) and PTH(1-11) exhibit extremely weak binding affinities (Kd>>100 μM) but are nonetheless capable of eliciting cAMP-signaling responses, albeit with potencies (EC50s≧100 μM) that are substantially weaker than that of PTH(1-34)(EC50~2 nM) (Luck, M D et al., *Molecular Endocrinology* 13:670-680 (1999)). It has been reported that a series of modified PTH(1-14) and PTH (1-11) analogs exhibit signaling potencies that are nearly, or even fully, equal to that of PTH(1-34) (Shimizu, M et al., *Endocrinology* 142: 3068-3074 (2001); Shimizu, M. et al., *J. Biol. Chem.* 276:490003-49012 (2001); Shimizu, M. et al., *J. Biol. Chem.* 275: 21836-21843 (2000)).

Recently, it was also reported that PTH(1-14) analogs containing the α,α-disubstitued amino acid, α-aminoisobutyric acid (Aib) at positions 1 and/or 3, have 10- to 100-fold higher affinities and cAMP signaling potencies than do their counterpart peptides containing alanine at these positions (Shimizu, N. et al. *J. Biol. Chem.* 276: 49003-49012 (2001)).

BRIEF SUMMARY OF THE INVENTION

The invention provides novel PTH polypeptide derivatives containing amino acid substitutions at selected positions in the polypeptides. The derivatives function as full, or nearly full, agonists of the PTH-1 receptor. Because of their unique properties, these polypeptides have utility as drugs for treating human diseases of the skeleton, such as osteoporosis.

The invention provides derivatives of PTH(1-14), PTH(1-13), PTH(1-12), PTH(1-11), PTH(1-10) and PTH (1-9) polypeptides, wherein at least one residue in each polypeptide is an α,α-di-substituted amino acid. These polypeptides may also contain a residue which is a helix, preferably an α-helix, stabilizing residue. These α-helix stabilizing residues include, but are not limited to α,α-di-alkyl amino acids with structurally varied sidechains, such as: α-aminoisobutyric acid (Aib), α,α-diethyl-glycine (Deg), 1-aminocyclopropane-1-carboxylic acid ($Ac_3c$), 1-aminocyclopentane-1-carboxylic acid ($Ac_5c$), amino-cyclobutane-1-carboxylic acid ($Ac_4c$), and 1-amino-cyclohexane-1-carboxylic acid ($Ac_6c$). The invention also provides methods of making such peptides. Further, the invention encompasses compositions and methods for use in limiting undesired bone loss in a vertebrate at risk of such bone loss, in treating conditions that are characterized by undesired bone loss or by the need for bone growth, e.g. in treating fractures or cartilage disorders and for raising cAMP levels in cells where deemed necessary.

In one aspect, the invention is directed to a biologically active peptide consisting essentially of $X_{01}VaIX_{02}GluIleGlnLeuMetHisX_{03}X_{04}X_{05}X_{06}X_{07}$(SEQ. ID. NO. 1), wherein $X_{01}$ is an α-helix-stabilizing residue, Gly, Ser or Ala; $X_{02}$ is an α-helix-stabilizing residue, Ala or Ser; $X_{03}$ is Ala, Gln or Asn; $X_{04}$ is Arg, Har or Leu; $X_{05}$ is an α-helix stabilizing residue, Ala or Gly; $X_{06}$ is an α-helix stabilizing residue or Lys; $X_{07}$ is an α-helix stabilizing residue, Trp or His; wherein at least one of $X_{01}$, $X_{02}$, $X_{03}$, $X_{04}$, $X_{05}$, $X_{06}$, or $X_{07}$ is an α-helix stabilizing residue, and wherein at least one of said α-helix stabilizing residues is Aib (α-aminoisobutyric acid), $Ac_3c$ (1-aminocyclopropane-1-carboxylic acid), $Ac_4c$ (1-amino-cyclobutane-1-carboxylic acid), $Ac_5c$ (1-aminocyclopentane-1-carboxylic acid), $Ac_6c$(1-amino-cyclohexane-1-carboxylic acid), or Deg (α,α-diethylglycine).

The invention is further drawn to fragments of the peptide having the sequence of SEQ. ID. NO. 1, in particular $X_{01}VaIX_{02}GluIleGlnLeuMetHisX_{03}X_{04}X_{05}X_{06}$ (part of SEQ. ID. NO. 1), $X_{01}VaIX_{02}GluIleGlnLeuMetHisX_{03}X_{04}X_{05}$ (part of SEQ. ID. NO. 1), $X_{01}VaIX_{02}GluIleGlnLeuMetHisX_{03}X_{04}$ (part of SEQ. ID. NO. 1), $X_{01}VaIX_{02}GluIleGlnLeuMetHisX_{03}X_{04}$ (part of SEQ. ID. NO. 1), and $X_{01}VaIX_{02}GluIleGlnLeuMetHis$ (part of SEQ. ID. NO. 1). The invention further encompasses pharmaceutically acceptable salts of the above-described peptides, and N- or C-derivatives of the peptides, wherein at least one of $X_{01}$, $X_{02}$, $X_{02}$, $X_{03}$, $X_{04}$, $X_{05}$, or $X_{06}$ is an α-helix-stabilizing residue. One or more of the α-helix-stabilizing residue may be selected from the group consisting of Aib, $Ac_3c$, $Ac_4c$, $Ac_5c$, $Ac_6c$, or Deg.

In addition, the invention is drawn to a biologically active polypeptide consisting essentially of $X_{01}VaIX_{02}GluIleGlnLeuMetHisGlnHarAlaLysTrp$ (SEQ. ID. NO. 2) as well as fragment peptides containing amino acids 1-13, 1-12, 1-11, 1-10, or 1-9. The invention further encompasses pharmaceutically acceptable salts of the above-described peptides and N- or C-derivatives of the peptides, wherein $X_{01}$ is an α-helix-stabilizing residue, Gly, Ser or Ala; and $X_{02}$ is an α-helix-stabilizing residue, Ala, or Ser. α-helix stabilizing residues include, but are not limited to, the group consisting of Aib, $Ac_3c$, $Ac_4c$, $Ac_5c$, $Ac_6c$, and Deg as defined above.

Preferred embodiments of the biologically active peptide include:
$Ac_5$cValAibGluIleGlnLeuMetHisGlnArgAlaLysTrpNH$_2$ (SEQ. ID. NO. 30),
$Ac_5$cValAlaGluIleGlnLeuMetHisGlnHarAlaLysTrpNH$_2$ (SEQ. ID. NO. 4),
AibValAc$_5$cGluIleGlnLeuMetHisAsnLeuGlyLysHisNH$_2$ (SEQ. ID. NO. 32), and
$Ac_5$cValAibGluIleGlnLeuMetHisNH$_2$ (SEQ. ID. NO. 31). It is contemplated that fragments of the above mentioned peptides, containing amino acids 1-9, 1-10, 1-11, 1-12 or 1-13, are also embodiments of the present invention. The invention further encompasses pharmaceutically acceptable salts of the above-described peptides, and N- or C-derivatives of the peptides.

In another aspect, the invention is directed to a biologically active peptide consisting essentially of $X_{01}VaIX_{02}GluIleX_{03}LeuMetHisX_{04}X_{05}X_{06}LysX_{07}$ (SEQ. ID. NO. 5), wherein $X_{01}$ is an α-helix-stabilizing residue, Gly, Ser or Ala; $X_{02}$ is an α-helix-stabilizing residue, Ala or Ser; $X_{03}$ is Ala, Gln or Asn; $X_{04}$ is Ala, Gln or Asn; $X_{05}$ is an α-helix-stabilizing residue, Ala, Gly, Har or Arg; $X_{06}$ is an α-helix-stabilizing residue or Lys; and $X_{07}$ is an α-helix-stabilizing residue, Trp or His; wherein at least one of $X_{01}$, $X_{02}$, $X_{03}$, $X_{04}$, $X_{05}$, $X_{06}$ or $X_{07}$ is an α-helix-stabilizing residue, and wherein at least one of said α-helix stabilizing residues is Aib, $Ac_3c$, $Ac_4c$, $Ac_5c$, $Ac_6C$, or Deg.

The invention is further drawn to fragments of the peptide having the sequence of SEQ. ID. NO. 5, in particular $X_{01}VaIX_{02}GluIleX_{03}LeuMetHisX_{04}X_{05}X_{06}Lys$ (part of SEQ. ID. NO. 5), $X_{01}VaIX_{02}GluIleX_{03}LeuMetHisX_{04}X_{05}X_{06}$ (part of SEQ. ID. NO. 5), $X_{01}VaIX_{02}GluIleX_{03}LeuMedHisX_{04}X_{05}$ (part of SEQ. ID. NO. 5), $X_{01}VaIX_{02}GluIleX_{03}LeuMetHisX_{04}$ (part of SEQ. ID. NO. 5), and $X_{01}VaIX_{02}GluIleX_{03}LeuMetHis$ (part of SEQ. ID. NO. 5), wherein $X_{01}$ is an α-helix-stabilizing residue, Gly, Ser or Ala; $X_{02}$ is an α-helix-stabilizing residue, Ala, or Ser; $X_{03}$ is Ala, Gln or Asn; $X_{04}$ is Ala, Gln or Asn; $X_{05}$ is an α-helix-stabilizing residue, Ala, Gly, Har or Arg; $X_{06}$ is an α-helix-stabilizing residue or Lys; and $X_{07}$ is an α-helix-stabilizing residue, Trp or His; wherein at least one of $X_{01}$, $X_{02}$, $X_{03}$, $X_{04}$, $X_{05}$, $X_{06}$ or $X_{07}$ is an α-helix-stabilizing residue, and wherein at least one of said α-helix stabilizing residues is Aib, $Ac_3c$, $Ac_4c$, $Ac_5c$, $Ac_6c$, or Deg. The invention further encompasses pharmaceutically acceptable salts of the above-described peptides, and N- or C-derivatives of the peptides.

In addition, the invention is drawn to a biologically active polypeptide consisting essentially of $X_{01}$ValX$_{02}$GluIleGlnLeuMetHisGlnHarAlaLysTrp-amide (SEQ. ID. NO. 6) and fragment peptides containing amino acids 1-13, 1-12, 1-11, 1-10, or 1-9. The invention further encompasses pharmaceutically acceptable salts of the above-described peptides, and N- or C-derivatives of the peptides, wherein $X_{01}$ is an α-helix-stabilizing residue, Gly, Ser or Ala; and $X_{02}$ is an α-helix-stabilizing residue, Ala or Ser, and wherein at least one of said α-helix stabilizing residues is Aib, $Ac_3c$, $Ac_4c$, $Ac_5c$, $Ac_6c$, or Deg.

Preferred embodiments of the biologically active peptide include:
$Ac_4c$ValAibGluIleGlnLeuMetHisGlnHarAlaLysTrp (SEQ. ID. NO. 7), $Ac_6c$ValAibGluIleGlnLeuMetHisGlnHarAlaLysTrp (SEQ. ID. NO. 8), $Ac_5c$Val $Ac_4c$GluIleGlnLeuMetHisGlnHarAlaLysTrp (SEQ. ID. NO. 9), $Ac_5c$ValAc$_6$cGluIleGlnLeuMetHisGlnHarAlaLysTrp (SEQ. ID. NO. 10), $Ac_4c$Val $Ac_4c$GluIleGlnLeuMetHisGlnHarAlaLysTrp (SEQ. ID. NO. 11), and $Ac_6c$Val $Ac_6c$GluIleGlnLeuMetHisGlnHarAlaLysTrp (SEQ. ID. NO. 12). It is contemplated that fragments of the above mentioned peptides, containing amino acids 1-9, 1-10, 1-11, 1-12, or 1-13, are also embodiments of the present invention. The invention further encompasses pharmaceutically acceptable salts of the above-described peptides, and N- or C-derivatives of the peptides.

This invention also provides pharmaceutical compositions comprising any of the PTH derivatives described herein and a pharmaceutically acceptable excipient and/or a pharmaceutically acceptable solution such as saline or a physiologically buffered solution.

In one aspect, the invention is directed to a pharmaceutical composition comprising the biologically active peptide having the sequence of SEQ. ID. NOs. 1, 5 or any of the above peptides, and a pharmaceutically acceptable carrier.

In another aspect, the invention is directed to a method of making SEQ. ID: NO. 1, 5 or any of the above peptides, wherein the peptide is synthesized by solid phase synthesis, liquid phase synthesis, or solution phase synthesis.

In another aspect, the invention is directed to a method of making SEQ. ID. NO. 1,5 or any of the above peptides, wherein the peptide is protected by FMOC.

This invention also provides a method for treating mammalian conditions characterized by decreases in bone mass, the method of which comprises administering to a subject in need thereof an effective bone mass-increasing amount of a biologically active PTH polypeptide derivative. A preferable embodiment of the invention is drawn to conditions such as osteoporosis, hyperparathyroidism and hypercalcemia. The types of osteoporosis include, but are not limited to old age osteoporosis and postmenopausal osteoporosis.

In another aspect, the invention is directed to a method for treating mammalian conditions characterized by decreases in bone mass, the method comprising administering to a subject in need thereof an effective bone mass-increasing amount of a biologically active peptide of having the sequence of SEQ. ID. NO. 1 or 5, or any of the above peptides and a pharmaceutically acceptable carrier. Additional preferable embodiments include using an effective amounts of the polypeptide of about 0.01 μg/kg/day to about 1.0 μg/kg/day wherein the polypeptide is administered parenterally, subcutaneously or by nasal insufflation.

This invention also provides a method for determining rates of bone reformation, bone resorption and/or bone remodeling comprising administering to a patient an effective amount of a labeled PTH polypeptide, such as for example, a peptide having the sequence of SEQ. ID. NO. 1, 5 or derivatives thereof and determining the uptake of the peptide into the bone of the patient. The peptide may be labeled with a label selected from the group consisting of: radiolabels, fluorescent labels, bioluminescent labels, or chemiluminescent labels. In a preferable embodiment the radiolabel is $^{125}$I or $^{99m}$Tc.

DETAILED DESCRIPTION OF THE INVENTION

Definitions

Figure 1:
FIG. 1. α,α-disubstituted amino acid analog structures Aib, Deg, $Ac_3c$, $Ac_5c$. Note the restricted φ/ψ rotation favors helix formation. (modified from R. Kau. and P. Balaram, *Bioorganic Medicinal Chemistry*, 7 105-117(1999)).
Figure 1:
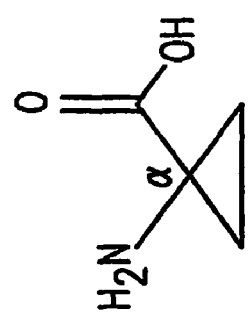
Figure 1:
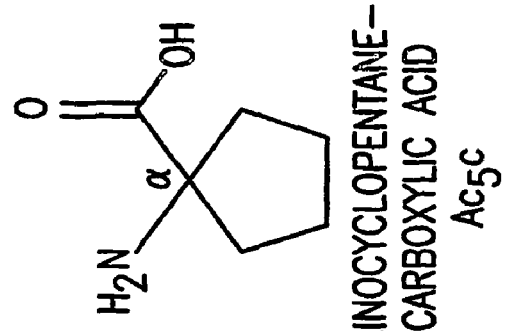
Figure 1:
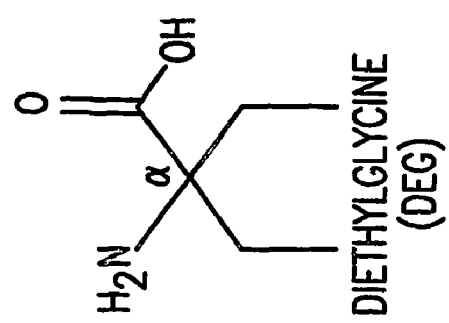
Figure 2A:
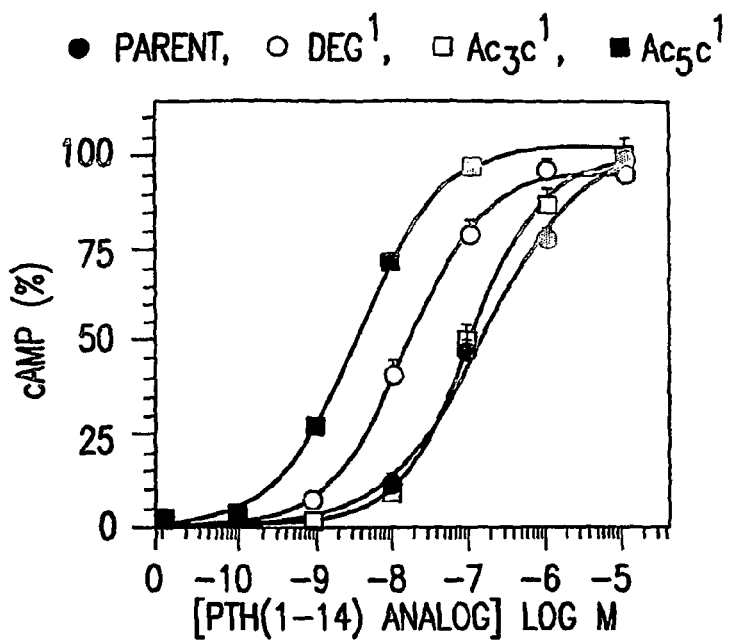
FIG. 2. Effect of single α,α-substituted amino acid substitutions at position 1 or 3 in a PTH(1-14) analog on cAMP-stimulating potency and P1R-binding affinity in HKRK-B28 cells. The peptide [Ala$^{1,3,12}$, Gln$^{10}$, Har$^{11}$, Trp$^{14}$]PTH(1-14)NH$_2$(parent)(SEQ. ID. NO. 13) and analogs thereof in which alanine-1 or alanine-3 were substituted with 1-aminocyclopropane-1-carboxylic acid ($Ac_3c$); 1-aminocyclopentane-1-carboxylic acid ($Ac_5c$) or α,α-diethylglycine (Deg) were evaluated in HKRK-B28 cells for their capacity to stimulate intracellular cAMP accumulation (A), (C) and the capacity to inhibit binding of $^{125}$I-[Aib$^{1,3}$,Nle$^8$, Gln$^{10}$,Har$^{11}$,Ala$^{12}$, Trp$^{14}$,Arg$^{19}$,Tyr$^{21}$]rPTH(1-21)NH$_2$ (SEQ. ID. NO. 36) (B), (D). The cAMP responses are expressed as a percent of the maximum response observed in each experiment for the parent peptide, the average of which was 225±21 picomoles of cAMP per well (n=7); the corresponding basal cAMP level was 3.8±0.1 picomoles per well. Peptides and their corresponding symbols are identified in the key.
Figure 2B:
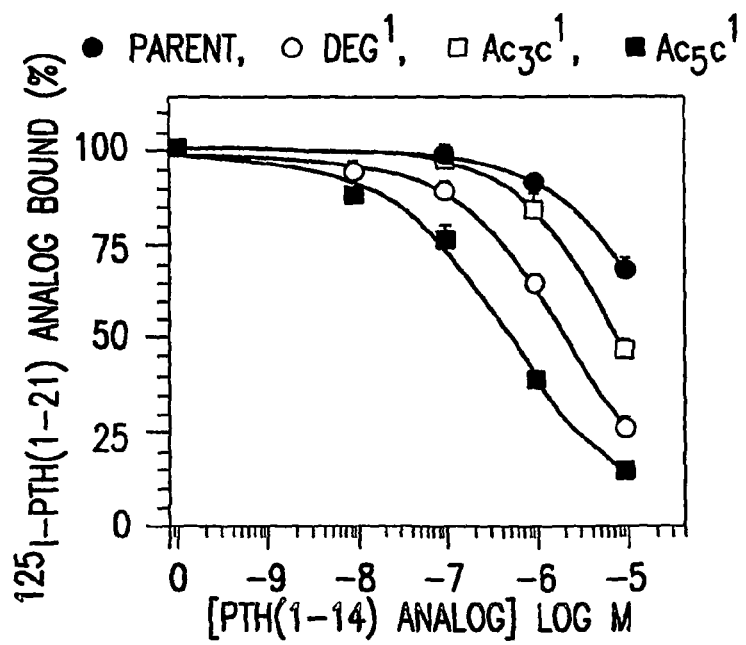
Figure 2C:
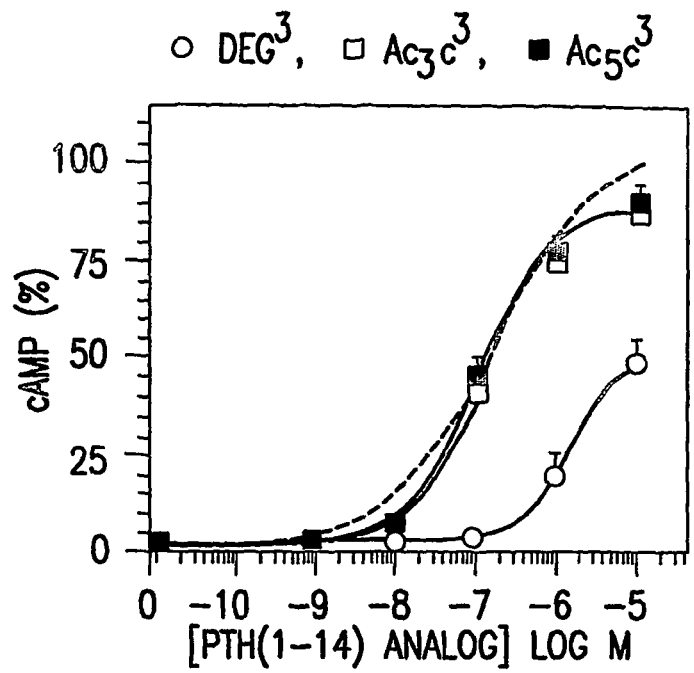
Figure 2D:
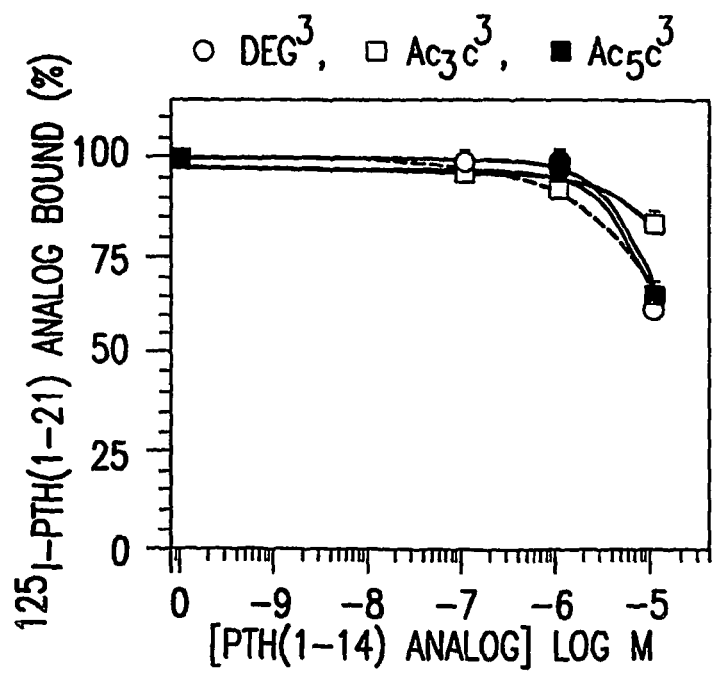
Figure 3A:
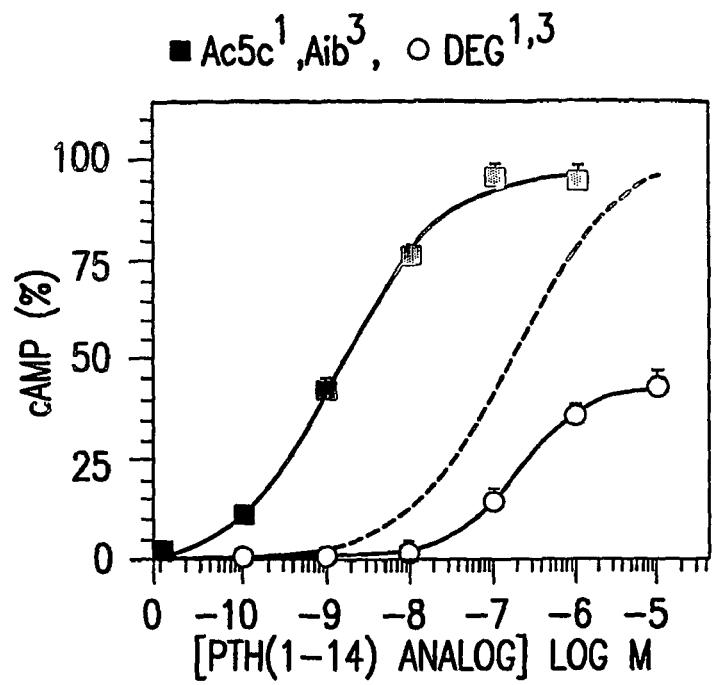
FIG. 3. Effects of combined α,α-disubstituted amino acid substitutions at positions 1 and 3 in a PTH(1-14) analog on cAMP-stimulating potency and binding affinity in HKRK-B28 cells. The peptide [$Ac_5c^1$,Aib$^3$,Gln$^{10}$,Har$^{11}$,Ala$^{12}$,Trp$^{14}$] PTH(1-14)NH$_2$ (SEQ. ID. NO. 15) and [Deg$^{1,3}$,Gln$^{10}$,Har$^{11}$, Ala$^{12}$,Trp$^{14}$]PTH(1-14)NH$_2$ (SEQ. ID. NO. 27) were evaluated in HKRK-B28 cells for the capacity to stimulate intracellular cAMP accumulation (A) and the capacity to inhibit the binding of $^{125}$I-[Aib$^{1,3}$,Nle$^8$,Gln$^{10}$,Har$^{11}$,Ala$^{12}$, Trp$^{14}$,Arg$^{19}$,Tyr$^{21}$]rPTH(1-21)NH$_2$ (SEQ. ID. NO. 36) (B). Also shown is the response observed with the parent peptide [Ala$^{1,3,12}$,Gln$^{10}$,Har$^{11}$,Trp$^{14}$]PTH(1-14)NH$_2$(SEQ. ID. NO. 13). The cAMP responses are expressed as a percent of the maximum response observed in each experiment for the parent peptide. Peptides and corresponding symbols are identified in the key.
Figure 3B:
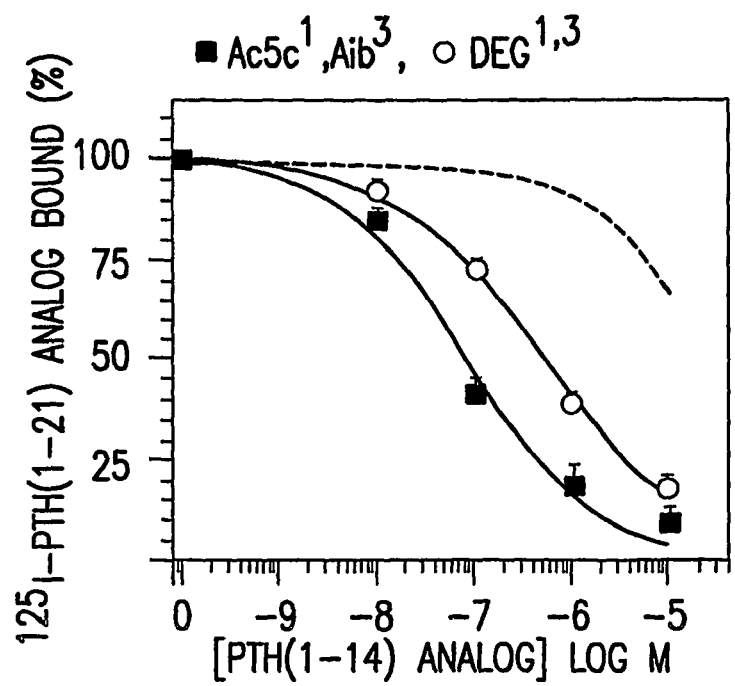
Figure 4:
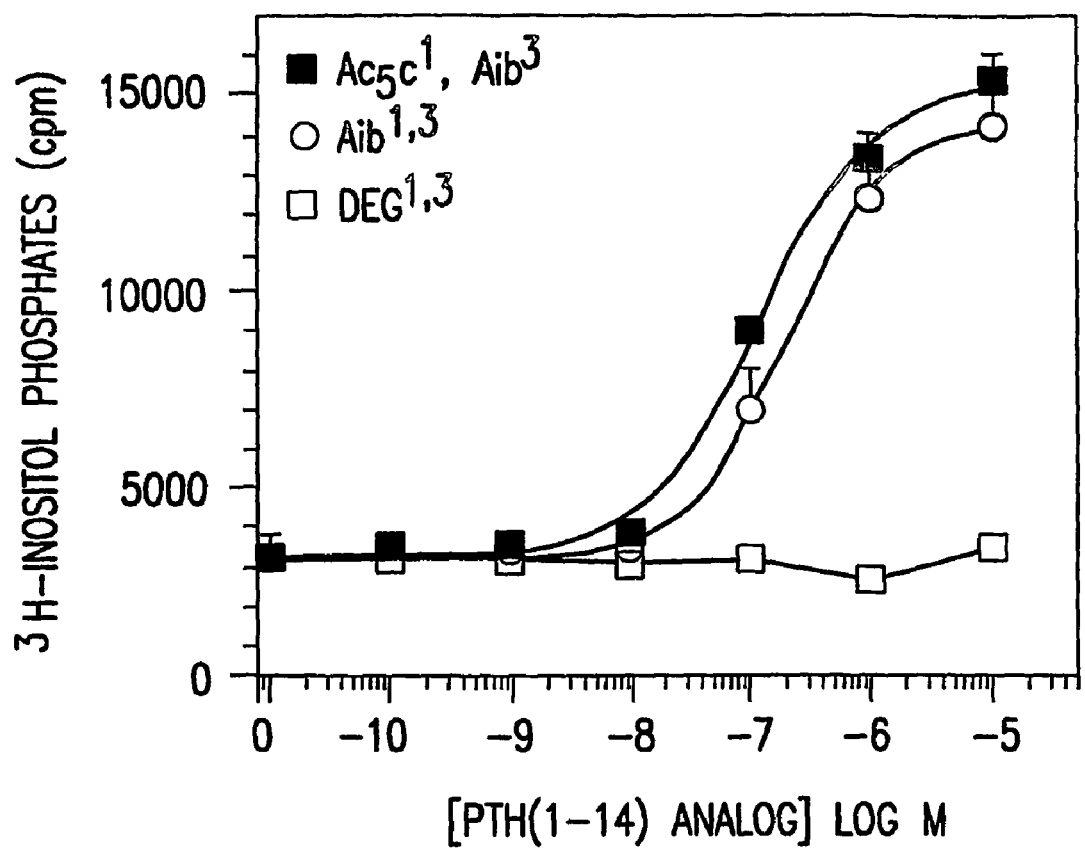
FIG. 4. Phospholipase-C signaling properties of PTH(1-14) analogs in COS-7 cells expressing the hP1R. The capacities of [$Ac_5c^1$,Aib$^3$,Gln$^{10}$,Har$^{11}$,Ala$^{12}$,Trp$^{14}$]PTH(1-14)NH$_2$ (SEQ. ID. NO. 15), [Aib$^{1,3}$,Gln$^{10}$,Har$^{11}$,Ala$^{12}$,Trp$^{14}$]PTH(1-14)NH$_2$ (SEQ. ID. NO. 3), and [Deg$^{1,3}$,Gln$^{10}$,Har$^{11}$,Ala$^{12}$, Trp$^{14}$]PTH(1-14)NH$_2$ (SEQ. ID. NO. 27) To stimulate formation of 3H-inositol phosphates (IP$^1$+IP$^2$+IP$^3$) in COS-7 cells transiently transfected with the hP1R, were evaluated. Peptides and corresponding symbols are defined in the key.
Figure 5A:
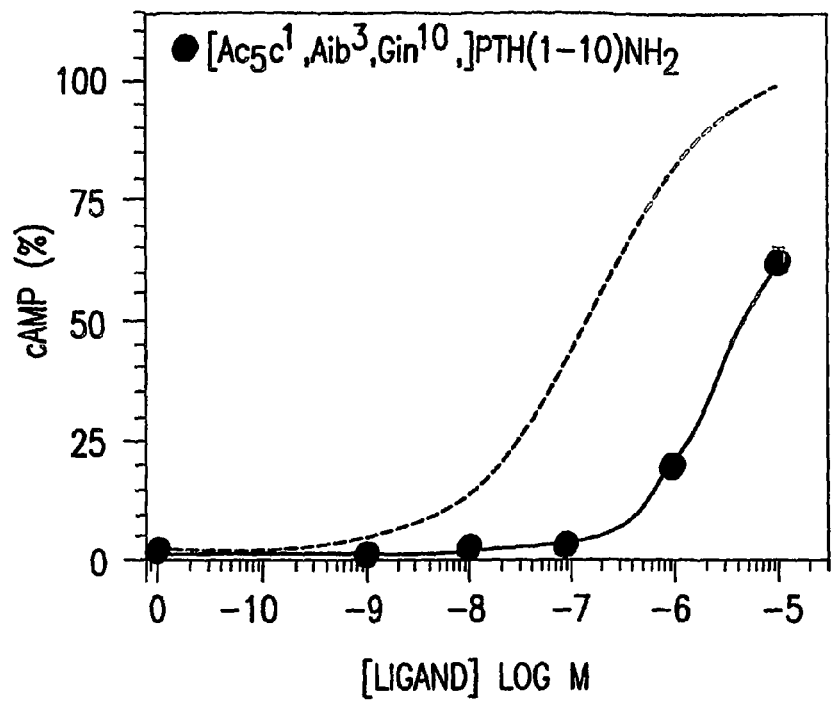
FIG. 5. Stimulation of cAMP formation by PTH(1-9) and PTH(1-10) analogs in HKRK-B28 cells. Panel A shows the capacity of varying concentrations of [Ac$_5$c$^1$,Aib$^3$,Gln$^{10}$] PTH(1-10)NH$_2$ (SEQ. ID. 22) to stimulate intracellular cAMP accumulation in HKRK-B28 cells. The response to [Ala$^{1,3,12}$,Gln$^{10}$,Har$^{11}$,Trp$^{14}$]PTH(1-14)NH$_2$ (SEQ. ID. NO. 13) is reshown from FIG. 2A. Panel B shows the cAMP levels in cells treated with buffer alone (basal) or buffer containing either native PTH(1-9)NH$_2$, [Aib$^{1,3}$]PTH(1-9)NH$_2$ (SEQ. ID. NO. 37) or [Ac$_5$c$^1$,Aib$^3$]PTH(1-9)NH$_2$ (SEQ. ID. NO. 34), each at a concentration of 100 μM (P versus basal=0.052(*) or <0.0001(a); P versus [Aib$^{1,3}$]PTH(1-9)NH$_2$=0.001(b)(SEQ. ID. NO. 37). Also analyzed were [Ac$_5$c$^1$,Aib$^3$,Gln$^{10}$]PTH(1-10)NH$_2$ (SEQ. ID. NO. 22) at 10 μM, and [Ac$_5$c$^1$,Aib$^3$,Gln$^{10}$, Har$^{11}$,Ala$^{12}$,Trp$^{14}$]PTH(1-14)NH$_2$ (SEQ. ID. 15) at 10 nM, for which 33-fold (P=0.0003) and 38-fold (P=0.006) increases in cAMP levels, relative to basal, were observed, respectively. Peptides and corresponding symbols are identified in the key.
Figure 5B:
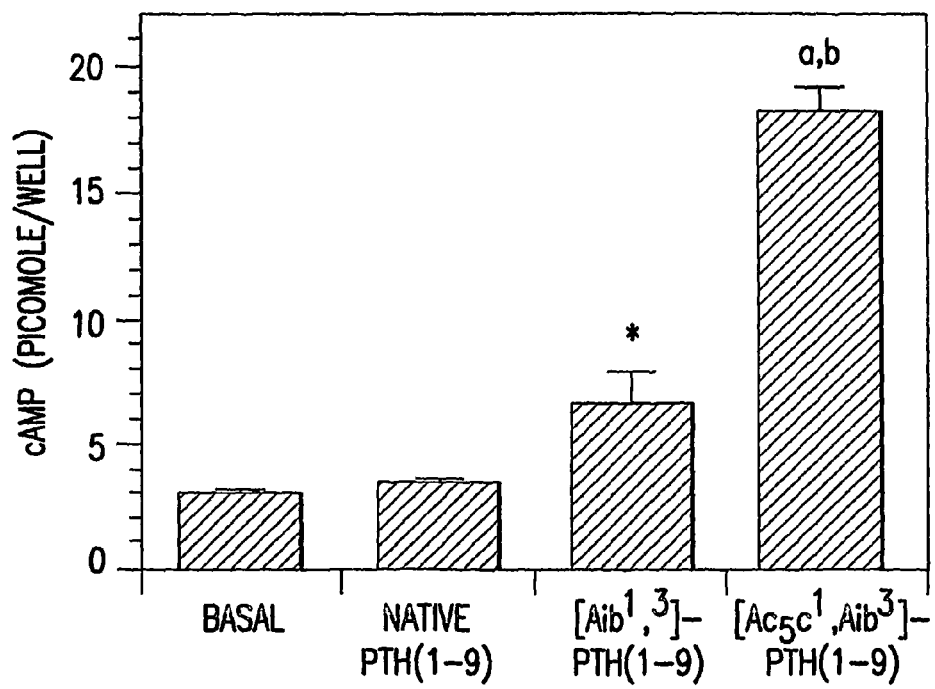
Figure 6:
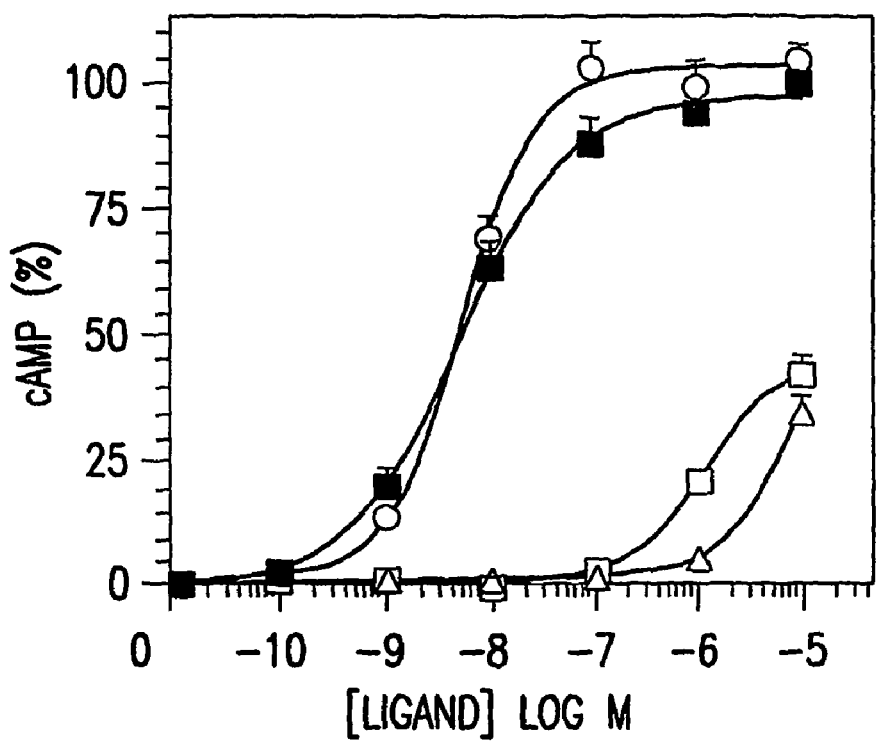
FIG. 6. cAMP-stimulating capacities of PTH(1-14) and a PTH(1-10) analogs in LdelNt-2 cells. The peptides [Aib$^{1,3}$, Gln$^{10}$,Har$^{11}$,Ala$^{12}$,Trp$^{14}$]PTH(1-14)NH$_2$(SEQ. ID. NO. 3), [Ac$_5$c$^1$,Aib$^3$,Gln$^{10}$,Har$^{11}$,Ala$^{12}$,Trp$^{14}$]PTH(1-14)NH$_2$(SEQ. ID. NO. 15), [Deg$^{1,3}$,Gln$^{10}$,Har$^{11}$,Ala$^{12}$,Trp$^{14}$]PTH(1-14)NH$_2$(SEQ. ID. NO. 27) and [Ac$_5$c$^1$,Aib$^3$,Gln$^{10}$]PTH(1-10)NH$_2$ (SEQ. ID. NO. 22) were evaluated for cAMP-stimulating potency in LdelNt-2 cells, which are clonal, LLC-PK1-derived cells that express hP1R-deINt via stable transfection. The data are expressed as a percent of the maximum response observed in each experiment for [Ac$_5$c$^1$,Aib$^3$,Gln$^{10}$,Har$^{11}$, Ala$^{12}$,Trp$^{14}$]PTH(1-14)NH$_2$(SEQ. ID. NO. 15), which was 125±19 picomoles of cAMP per well; the basal cAMP levels were 1.8±0.3 picomoles per well. The corresponding EC$_{50}$ values were 6.4±1.6 nM ([Aib$^{1,3}$,Gln$^{10}$,Har$^{11}$,Ala$^{12}$,Trp$^{14}$] PTH(1-14)NH$_2$)(SEQ. ID. NO. 3); 6.4±2.3 nM([Ac$_5$c$^1$,Aib$^3$, Gln$^{10}$,Har$^{11}$,Ala$^{12}$,Trp$^{14}$]PTH(1-14)NH$_2$(SEQ. ID. NO. 15); 1.4±0.5 μM ([Deg$^{1,3}$,Gln$^{10}$,Har$^{11}$,Ala$^{12}$,Trp$^{14}$]PTH(1-14) NH$_2$) (SEQ. ID. NO. 27) and 37±22 μM([Ac$_5$c$^1$,Aib$^3$,Gln$^{10}$] PTH(1-10)NH$_2$) (SEQ. ID. NO. 22). Peptides and corresponding symbols are identified in the key.
Figure 7:
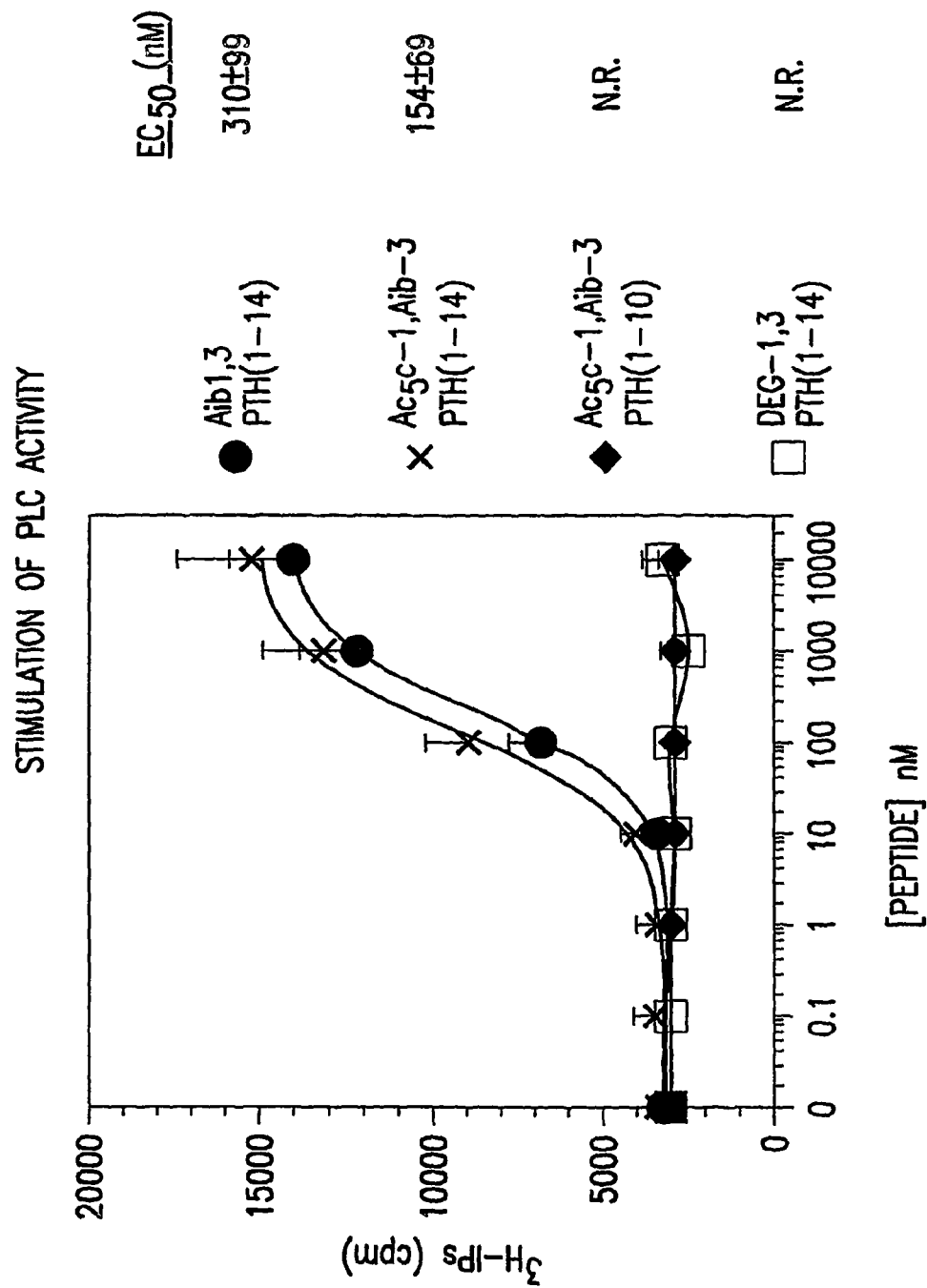
FIG. 7. Stimulation of PLC activity. The PTH(1-14) analog stimulated PLC activity in COS-7 cells transiently expressing hP1R-WT. Peptides and corresponding symbols are identified in the key.
Figure 8:
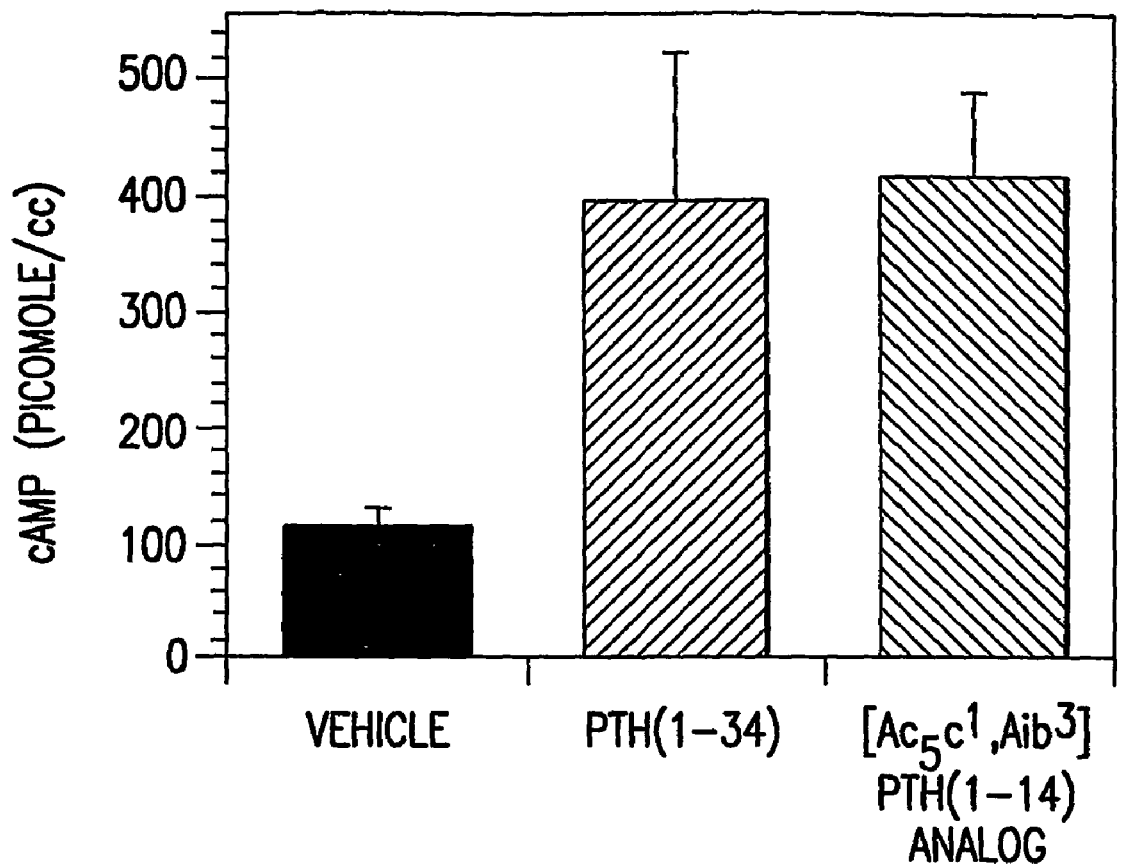
FIG. 8. Agonist activity of PTH analogs in vivo. Mice were injected intra-peritoneally with vehicle or vehicle containing either [Nle$^{8,21}$,Tyr$^{34}$]ratPTH(1-34)NH$_2$ (SEQ. ID. NO. 14), or [Ac$_5$c$^1$,Aib$^3$,Gln$^{10}$,Har$^{11}$,Ala$^{12}$,Trp$^{14}$]humanPTH(1-14) NH$_2$ (SEQ. ID. NO. 15) and 3 minutes later blood samples were withdrawn and plasma cAMP levels were determined by radioimmunoassay. The effective PTH peptide concentrations were 20×10$^{-9}$ mole per kilogram of body-weight for PTH(1-34) analog and 200×10$^{-9}$ mole per kilogram of body-weight for PTH(1-14) analog. Each bar represents the mean (±s.e.m.) cAMP value of data obtained from 4 mice.

Amino Acid Sequences: The amino acid sequences in this application use either the single letter or three letter designations for the amino acids. These designations are well known to one of skill in the art and can be found in numerous readily available references, such as for example in Cooper, G. M., *The Cell* 1997, ASM Press, Washington, D.C. or Ausubel et al., *Current Protocols in Molecular Biology*, 1994. Where substitutions in a sequence are referred to, for example, as Ser-3-->Ala or [Ala$^3$]peptide, this means that the serine in the third position from the N-terminal end of the polypeptide is replaced with another amino acid, Alanine in this instance.

Scaffold peptide: [M]PTH(1-14) is defined as [Ala$^{1,3,12}$, Gln$^{10}$,Har$^{11}$,Trp$^{14}$]PTH(1-14)amide (SEQ. ID. NO. 13). [M]PTH(1-11) is defined as [Ala$^{1,3}$,Gln$^{10}$,Har$^{11}$]PTH(1-11) NH$_2$ (SEQ. ID. NO. 16). [Aib$^{1,3}$,M]PTH(1-14) is defined as [Aib$^{1,3}$,Gln$^{10}$,Har$^{11}$,Ala$^{12}$,Trp$^{14}$]PTH(1-14)NH$_2$ (SEQ. ID. NO. 3).

α,α-dialkyl amino acids: "Aib" refers to α-aminoisobutyric acid; "Har" refers to homoarginine; "Nle" refers to norleucine; Ac$_3$c refers to 1-aminocyclopropane-1-carboxylic acid; Ac$_4$c refers to 1-amino-cyclobutane-carboxylic acid; Ac$_5$c refers to 1-aminocyclopentane-1-carboxylic acid; Ac$_6$c refers to 1-amino-cyclohexane-1-carboxylic acid; Deg refers to α,α-diethylglycine; IBMX refers to 3-isobutyl-1-methylxanthine; and other amino acids are in either the conventional one- or three-letter codes.

Biological Activity of the Protein: This expression refers to any biological activity of the polypeptide. Examples of these activities include, but are not limited to metabolic or physiologic function of compounds of a peptide having the sequence of SEQ. ID. NO. 1 or derivatives thereof, including similar activities or improved activities, or those activities with decreased undesirable side-effects. Also included are antigenic and immunogenic activities of the above-described compounds.

Derivative or Functional Derivative: The term "derivative" or "functional derivative" is intended to include "variants," the "derivatives," or "chemical derivatives" of the PTH molecule. A "variant" of a molecule such as for example, a compound of a peptide having the sequence of SEQ. ID. NO. 1 or derivative thereof is meant to refer to a molecule substantially similar to either the entire molecule, or a fragment thereof An "analog" of a molecule such as for example, a compound having the sequence of SEQ. ID. NO. 1 or derivative thereof is meant to refer to a non-natural molecule substantially similar to either the peptide having the sequence of SEQ. ID. NO. 1 molecules or fragments thereof.

PTH derivatives contain changes in the polypeptide relative to the native PTH polypeptide of the same size. The sequence of the native human ("hPTH") PTH (1-14) polypeptide is SerValSerGluIleGlnLeuMetHisAsnLeuGlyLysHis (part of SEQ. ID. NO. 26), or native rat ("rPTH") PTH (1-14) is AlaValSerGluIleGlnLeuMetHisAsnLeuGly LysHis (SEQ. ID. NO. 17). A molecule is said to be "substantially similar" to another molecule if the sequence of amino acids in both molecules is substantially the same, and if both molecules possess a similar biological activity. Thus, two molecules that possess a similar activity, may be considered variants, derivatives, or analogs as that term is used herein even if one of the molecules contains additional amino acid residues not found in the other, or if the sequence of amino acid residues is not identical. PTH derivatives, however, need not have substantially similar biological activity to the native molecule. In some instances PTH derivatives have substantially different activity than the native PTH. For example, a derivative may be either an antagonist or an agonist of the PTH receptor.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

Fragment: A "fragment" of a molecule such as for example, $X_{01}ValX_{02}GluIleGlnLeuMetHisX_{03}X_{04}X_{05}X_{06}$ (1-13) (part of SEQ. ID. NO. 1) or derivative thereof is meant to refer to any polypeptide subset of these molecules, including N- or C-derivatives thereof.

Fusion protein: As used herein, a "fusion protein" is a protein comprising compounds such as for example, $X_{01}ValX_{02}GluIleGlnLeuMetHisX_{03}X_{04}X_{05}X_{06}X_{07}$ (SEQ. ID. NO. 1), or derivatives thereof, either with or without a "selective cleavage site" linked at its N-terminus, which is in turn linked to an additional amino acid leader polypeptide sequence.

Polypeptide: Polypeptide and peptide are used interchangeably. The term polypeptide refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids and include amino acid sequences modified either by natural processes, such as post-translational processing, or by chemical modification techniques which are well known in the art. Such modifications are well described in basic texts and in more detailed monographs, as well as in the research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched and they may be cyclic, with or without branching. Cyclic, branched and branched cyclic polypeptides may result from post-translational modifications or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins,* B. C. Johnson, Ed., Academic Press, New York, 1983; Seifter et al., "Analysis for protein modifications and nonprotein cofactors", *Methods in Enzymol.* 182:626-646 (1990) and Rattan et al., "Protein Synthesis: Posttranslational Modifications and Aging", *Ann NY Acad Sci* 663:48-62 (1992).

PTH Receptor: PTH-1 receptor (P1R) is a class IIG protein coupled receptor, the amino-terminal extracellular (N)domain of which is thought to bind with the C-terminal portion of PTH.

PTH Analogs—Structural and Functional Properties

α-aminoisobutyric acid (Aib) and α,α-disubstituted amino acids distinct from Aib were introduced into short N-terminal PTH peptide analogs. The numerous NMR studies of PTH(1-34) analogs, performed in a variety of polar or non-polar solvents, have generally indicated two domains of secondary structure: a stable C-terminal helix extending approximately from Ser-17 to Val-31, and a shorter and less stable amino-terminal helix, extending variably from Ser-3 to Lys-13, the two domain being connected by a bend or turn region (Marx, U. C., et al., *Biochem. Biophys. Res. Commun.* 267:213-220 (2000); Chen, Z., et al., *Biochemistry* 39:12766-12777 (2000); Marx, U. C., et al., *J. Biol. Chem.* 270:15194-15202 (1995); Marx, U. C., et al., *J. Biol. Chem.* 273:4308-4316 (1998); Pellegrini, M., et al., *Biochemistry* 37:12737-12743 (1998); Gronwald, W., et al., *Biol. Chem. Hoppe Seyler* 377: 175-186 (1996); Barden, J. A., and Kemp, B. E., *Biochemistry* 32:7126-7132 (1993)). The recent crystallographic study of PTH(1-34) indicated a continuous α-helix extending from Ser-3 to His-32 and containing only a slight 15° bend at the mid-section. However, NMR data indicates that the N-terminal α-helix is relatively weak. Helix-stabilizing modifications, such as the introduction of Aib residues, offer significant benefits in terms of peptide potency, and result in short peptides (<14 amino acids) with activity comparable to PTH (1-34).

Described herein are novel "minimized" variants of PTH that are small enough to be deliverable by simple non-injection methods. The variants of the present invention contain substitutions in the first 14 amino acids of the polypeptide. The new polypeptides correspond to the 1-14,1-13, 1-12, 1-11, 1-10 and 1-9 amino acid sequence of the mature PTH polypeptide, unless otherwise noted. The shorter variants ($\leq$PTH1-14) have a molecular weight of less than 2,000 daltons.

As protein products, compounds described herein are amenable to production by the techniques of solution- or solid-phase peptide synthesis. The solid phase peptide synthesis technique, in particular, has been successfully applied in the production of human PTH and can be used for the production of these compounds (for guidance, see Kimura et al., supra, and see Fairwell et al., *Biochem.* 22:2691 (1983)). Success with producing human PTH on a relatively large scale has been reported by Goud et al., in *J. Bone Min. Res.* 6(8):781 (1991). The synthetic peptide synthesis approach generally entails the use of automated synthesizers and appropriate resin as solid phase, to which is attached the C-terminal amino acid of the desired compounds of peptides having the sequence of SEQ. ID. NO. 1 or derivatives thereof. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984). It will be appreciated that the peptide synthesis approach is required for production of such as for example, a peptide having the sequence of SEQ. ID. NO. 1 and derivatives thereof which incorporate amino acids that are not genetically encoded, such as Aib.

Substituents may be attached to the free amine of the N-terminal amino acid of compounds of the present invention standard methods known in the art. For example, alkyl groups, e.g., $C_{1-12}$ alkyl, are attached using reductive alkylation. Hydroxyalkyl groups, e.g. $C_{1-12}$ hydroxyalkyl, are also attached using reductive alkylation wherein the free hydroxy group is protected with a t-butyl ester. Acyl groups, e.g., $COE_1$, are attached by coupling the free acid, e.g., $E_1COOH$, to the free amino of the N-terminal amino acid. Additionally, possible chemical modifications of the C-terminal end of the polypeptide are encompassed within the scope of the invention. These modifications may modify binding affinity to the receptor.

Also contemplated within the scope of this invention are those compounds such as for example, a peptide having the sequence of SEQ. ID. NO. 1 and derivatives thereof with altered secondary or tertiary structure, and/or altered stability, which still retain biological activity. Such derivatives might be achieved through lactam cyclization, disulfide bonds, or other means known to a person of ordinary skill in the art. A preferable embodiment of the invention is drawn to any of the above recited polypeptides, wherein the polypeptide contains a C-terminal amide.

Utility and Administration of Compounds of the Invention

Compounds of the invention or derivatives thereof have multiple uses. These include, inter alia, agonists or antagonists of the PTH receptor, prevention and treatment of a variety of mammalian conditions manifested by loss of bone mass, diagnostic probes, antigens to prepare antibodies for use as diagnostic probes and even as molecular weight markers. Being able to specifically substitute one or more amino acids in the PTH polypeptide permits construction of specific molecular weight polypeptides.

In particular, the compounds of this invention are indicated for the prophylaxis and therapeutic treatment of osteoporosis and osteopenia in humans. Furthermore, the compounds of this invention are indicated for the prophylaxis and therapeutic treatment of other bone diseases. The compounds of this invention are also indicated for the prophylaxis and therapeutic treatment of hypoparathyroidism. Finally, the compounds of this invention are indicated for use as agonists for fracture repair and as antagonists for hypercalcemia.

In general, compounds of the present invention, or salts thereof, are administered in amounts between about 0.01 and 1 µg/kg body weight per day, preferably from about 0.07 to about 0.2 µg/kg body weight per day. For a 50 kg human female subject, the daily dose of biologically active compound is from about 0.5 to about 50 µgs, preferably from about 3.5 to about 10 µgs. In other mammals, such as horses, dogs, and cattle, higher doses may be required. This dosage may be delivered in a conventional pharmaceutical composition by a single administration, by multiple applications, or via controlled release, as needed to achieve the most effective results, preferably one or more times daily by injection. For example, this dosage may be delivered in a conventional pharmaceutical composition by nasal insufflation or by orally active means. Another method of administration includes subcutaneous injection, at least once daily, for potential anabolic effects on the skeleton.

The selection of the exact dose and composition and the most appropriate delivery regimen will be influenced by, inter alia, the pharmacological properties of the selected compounds of the invention, the nature and severity of the condition being treated, and the physical condition and mental acuity of the recipient.

Representative preferred delivery regimens include, without limitation, oral, parenteral, subcutaneous, transcutaneous, intramuscular and intravenous, rectal, buccal (including sublingual), transdermal, and intranasal insufflation.

Pharmaceutically acceptable salts retain the desired biological activity of the compounds of the invention without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Pharmaceutically acceptable buffers include but are not limited to saline or phosphate buffered saline. Also included in these solutions may be acceptable preservative known to those of skill in the art.

A further aspect of the present invention relates to pharmaceutical compositions comprising as an active ingredient compounds of the invention or derivatives thereof of the present invention, or pharmaceutically acceptable salt thereof, in admixture with a pharmaceutically acceptable, non-toxic carrier. As mentioned above, such compositions may be prepared for parenteral (subcutaneous, transcutaneous, intramuscular or intravenous) administration, particularly in the form of liquid solutions or suspensions; for oral or buccal administration, particularly in the form of tablets or capsules; for rectal, transdermal administration; and for intranasal administration, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985), incorporated herein by reference. Formulations for parenteral administration may contain as excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts or acylcarnitines. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

When formulated for one preferred route of administration, nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

One form of controlled release formulation contains the polypeptide or its salt dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189. The compounds or, preferably, their relatively insoluble salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J. R. Robinson ed., Marcel Dekker, Inc., New York, 1978, and R. W. Baker, Controlled Release of Biologically Active Agents, John Wiley & Sons, New York, 1987.

Like PTH, the PTH variants may be administered in combination with other agents useful in treating a given clinical condition. When treating osteoporosis and other bone-related disorders for example, the PTH variants may be administered in conjunction with a dietary calcium supplement or with a vitamin D analog (see U.S. Pat. No. 4,698,328). Alternatively, the PTH variant may be administered, preferably using a cyclic therapeutic regimen, in combination with bisphosphonates, as described for example in U.S. Pat. No. 4,761,406, or in combination with one or more bone therapeutic agents such as, without limitation, calcitonin and estrogen.

PTH Analog Receptor-Signaling Activities

A crucial step in the expression of hormonal action is the interaction of hormones with receptors on the plasma membrane surface of target cells. The formation of hormone-receptor complexes allows the transduction of extracellular signals into the cell to elicit a variety of biological responses.

Polypeptides described herein can be screened for their agonistic or antagonistic properties using the cAMP accumulation assay. Cells expressing PTH-1 receptor on the cell surface are incubated with native PTH(1-84) (SEQ. ID. NO. 18) for 5-60 minutes at 37° C., in the presence of 2 mM IBMX (3-isobutyl-1-methyl-xanthine, Sigma, St. Louis, Mo.). Cyclic AMP accumulation is measured by specific radioimmunoassay. A compound that competes with native PTH (1-84) or PTH(1-34) (SEQ. ID. NO. 19) for binding to the PTH-1 receptor, and that inhibits the effect of native PTH(1-84) or PTH(1-34) on cAMP accumulation, is considered a competitive antagonist. Such a compound would be useful for treating hypercalcemia.

Conversely, a PTH analog described herein or a derivative thereof that does not compete with native PTH(1-84) or PTH (1-34) for binding to the PTH-1 receptor, but which still prevents native PTH(1-84) or PTH(1-34) activation of cAMP accumulation (presumably by blocking the receptor activation site) is considered a non-competitive antagonist. Such a compound would also be useful for treating hypercalcemia.

The compounds described herein that compete with native PIH(1-84) or PTH(1-34)) for binding to the PTH-1 receptor, and which stimulates cAMP accumulation in the presence or absence of native PTH(1-84) or PTH(1-34) are competitive agonists. A compound that does not compete with native PTH(1-84) or PTH(1-34) for binding to the PTH-1 receptor but which is still capable of stimulating cAMP accumulation in the presence or absence of native PTH(1-84) or PTH(1-34), or which stimulates a higher cAMP accumulation than that observed by a compound of the invention or a derivative thereof alone, would be considered a non-competitive agonist.

Therapeutic Uses of PTH Analogs

Some forms of hypercalcemia and hypocalcemia are related to the interaction between PTH and PTHrP and the PTH-1 and receptors. Hypercalcemia is a condition in which there is an abnormal elevation in serum calcium level; it is often associated with other diseases, including hyperparathyroidism, osteoporosis, carcinomas of the breast, lung and prostate, epidermoid cancers of the head and neck and of the esophagus, multiple myeloma, and hypemephroma. Hypocalcemia, a condition in which the serum calcium level is abnormally low, may result from a deficiency of effective PTH, e.g., following thyroid surgery.

By "agonist" is intended a ligand capable of enhancing or potentiating a cellular response mediated by the PTH-1 receptor. By "antagonist" is intended a ligand capable of inhibiting a cellular response mediated by the PTH-1 receptor. Whether any candidate "agonist" or "antagonist" of the present invention can enhance or inhibit such a cellular response can be determined using art-known protein ligand/receptor cellular response or binding assays, including those described elsewhere in this application.

In accordance with yet a further aspect of the invention, there is provided a method for treating a medical disorder that results from altered or excessive action of the PTH-1 receptor, comprising administering to a patient therapeutically effective amount of a compound of the invention or a derivative thereof sufficient to inhibit activation of the PTH-1 receptor of said patient.

In this embodiment, a patient who is suspected of having a disorder resulting from altered action of the PTH-1 receptor can be treated using compounds of the invention or derivatives thereof of the invention which are a selective antagonists of the PTH-1 receptor. Such antagonists include compounds of the invention or derivatives thereof of the invention which have been determined (by the assays described herein) to interfere with PTH-1 receptor-mediated cell activation or other derivatives having similar properties.

To administer the antagonist, the appropriate compound of the invention or a derivative thereof is used in the manufacture of a medicament, generally by being formulated in an appropriate carrier or excipient such as, e.g., physiological saline, and preferably administered intravenously, intramuscularly, subcutaneously, orally, or intranasally, at a dosage that provides adequate inhibition of a compound of the invention or a derivative thereof binding to the PTH-1 receptor. Typical dosage would be 1 ng to 10 mg of the peptide per kg body weight per day.

In accordance with yet a further aspect of the invention, there is provided a method for treating osteoporosis, comprising administering to a patient a therapeutically effective amount of a compound of the invention or a derivative thereof, sufficient to activate the PTH-1 receptor of said patient. Similar dosages and administration as described above for the PTH/PnkrP antagonist, can be used for administration of a PTH/PTHrP agonist, e.g., for treatment of conditions such as osteoporosis, other metabolic bone disorders, and hypoparathyroidism and related disorders.

It will be appreciated by those skilled in the art that the invention can be performed within a wide range of equivalent parameters of composition, concentration, modes of administration, and conditions without departing from the spirit or scope of the invention or any embodiment thereof.

Having now fully described the invention, the same will be more readily understood by reference to specific examples which are provided by way of illustration, and are not intended to be limiting of the invention, unless herein specified.

EXAMPLES

The following protocols and experimental details are referenced in the examples that follow.

Example 1

Materials and Methods

Peptides. The amino acid sequences of the peptides used in the study were all derived from human or rat PTH sequences and contain a free amino-terminus and an amidated C-terminus. The parent peptide used as a starting scaffold was [M]PTH(1-14), which is defined as [Ala$^{1,3,12}$,Gln$^{10}$,Har$^{11}$, Trp$^{14}$]PTH(1-14)NH$_2$ (SEQ. ID. NO. 13). Peptides were prepared on automated peptide synthesizers (model 430A PE, Applied Biosystems, Foster City, Calif., or Model 396 MBS Advanced Chem Tect, Louisville, Ky.) using FMOC mainchain protecting group chemistry, HBTU/HOBt/DIEA (1:1:2 molar ratio) for coupling reactions, and TFA-mediated cleavage/sidechain-deprotection (MGH Biopolymer Synthesis Facility, Boston, Mass.). All peptides were desalted by adsorption on a C18-containing cartridge, and purified further by HPLC. The dry peptide powders were reconstituted in 10 mM acetic acid and stored at −80° C. The purity, identity, and stock concentration for each peptide was secured by analytical HPLC, Matrix-assisted laser desorption/ionization (MALDI) mass spectrometry and amino acid analysis. Radiolabeling of [M]PTH(1-21) (SEQ. ID. NO. 20) and [Aib$^{1,3}$,M]PTH(1-21) (SEQ. ID. NO. 21) was performed using $^{125}$I—Na (2,200 Ci/mmol, NEN) and chloramine-T; the resultant radioligands were purified by HPLC.

Cell Culture. The cell line HKRK-B28 (Takasu, H., et al., J. Bone Miner. Res. 14:11-20 (1999)) was derived from the porcine kidney cell line, LLC-PK$_1$ by stable transfection with plasmid DNA encoding a recombinant P1R chimera comprised of the opposum P1R from the N-terminus to the mid region of TM3 and the rat P1R from the mid region of TM3 to the C-terminus. The surface density of the P1R in these cells is ~280,000 receptors per cell. The clonal cell line LdelNt-2 was derived from LLC-PK, cells via stable transfection with a plasmid encoding P1R-delNt, a recombinant human PTH-1 receptor construct in which most of the amino-terminal extracellular domain is deleted. These cells, as well as COS-7 cells and SaOS-2-B10 cells, were cultured at 27° C. in T-75 flasks (75 mm$^2$) in Dulbecco's modified Eagle's medium (DMEM) supplemented with fetal bovine serum (10%), penicillin G (20 units/ml), streptomycin sulfate (20 µg/ml) and amphotericin B (0.05 µg/ml) in a humidified atmosphere containing 5% CO$_2$. Stock solutions of EGTA/trypsin and antibiotics were from GLBCO; fetal bovine serum was from Hyclone Laboratories (Logan, Utah). COS-7 cells sub-cultured in 24-well plates were transfected with plasmid DNA (200 ng per well) encoding the wild-type human P1R or truncated human P1R deleted for residues (24-181) (Shimizu, M., et al., J. Biol. Chem. 275:21836-21843 (2000)) that was purified by cesium chloride/ethidium bromide density gradient centrifugation, and FuGENE 6 transfection reagent (Roche Indianapolis Ind.) according to the manufacturer's recommended procedure. All cells, in 24-well plates, were treated with fresh media and shifted to 33° C. for 12 to 24 h prior to assay.

cAMP Stimulation. Stimulation of cells with peptide analogs was performed in 24-well plates. Cells were rinsed with 0.5 mL of binding buffer (50 mM Tris-HCl, 100 mM NaCl, 5 mM KCl, 2 mM CaCl$_2$, 5% heat-inactivated horse serum, 0.5% fetal bovine serum, adjusted to pH 7.5 with HCl) and treated with 200 µL of cAMP assay buffer (Delbecco's modified Eagle's medium containing 2 mM 3-isobutyl-1-methylxanthine, 1 mg/mL bovine serum albumin, 35 mM Hepes-NaOH, pH 7.4) and 100 µL of binding buffer containing varying amounts of peptide analog (final volume=300 µL). The medium was removed after incubation for 30 to 60 minutes at room temperature, and the cells were frozen on dry ice, lysed with 0.5 mL 50 mM HCl, and refrozen (~80° C.). The cAMP content of the diluted lysate was determined by radioimmunoassay. The EC$_{50}$ response values were calculated using nonlinear regression (see below).

FMOC. (Fluorenylnethoxycarbonyl group) A group used for linkage to amino groups for the purpose either of forming fluorescent amino-acid derivatives that can readily be detected after column chromatography, or to protect the amino groups of amino acids or nucleotides while other functional groups are undergoing reaction. Reagents useful for introducing the group are 9-fluorenylmethyl chloroformate and 9-fluorenyl-methyl succinimidyl carbonate.

Competition Binding. Binding reactions were performed with HKRK-B28 cells or in COS-7 cells in 24-well plates. The cells were rinsed with 0.5 mL of binding buffer, and then treated successively with 100 µL binding buffer, 100 µL of binding buffer containing various amounts of unlabeled competitor ligand, and 100 µL of binding buffer containing ca. 100,000 cpm of $^{125}$I-[Aib$^{1,3}$,Nle$^8$,Gln$^{10}$,Har$^{11}$,Ala$^{12}$,Trp$^{14}$, Arg$^{19}$,Tyr$^{21}$]rPTH(1-21) (SEQ. ID. NO. 36) (ca. 26 fmol; final volume=300 µL). Incubations were 4 to 6 h at 4° C., at which time near equilibrium conditions were attained. Cells were then placed on ice, the binding medium was removed, and the monolayer was rinsed three times with 0.5 mL of cold binding buffer. The cells were subsequently lysed with 0.5 mL 5N NaOH and counted for radioactivity. For each tracer and in each experiment, the non-specific binding was determined as the radioactivity that bound in the presence of the same unlabeled peptide at a concentration of 1 µM, and was ~1% of total radioactivity added for each tracer. The maximum specific binding (B$_0$) was the total radioactivity bound in the absence of competing ligand, corrected for nonspecific binding, and for each tracer, ranged from 8% to 20% of the total radioactivity added. Nonlinear regression was used to calculate binding IC$_{50}$ values (see below). Scatchard transformations of homologous competition binding data derived from studies with 26 fmol of $^{125}$I-[Aib$^{1,3}$,Nle$^8$,Gln$^{10}$,Har$^{11}$, Ala$^{12}$,Trp$^{14}$, Arg$^{19}$,Tyr$^{21}$]rPTH(1-21) (SEQ. ID. NO. 36) were employed for estimations of apparent equilibrium dissociation constant (k$_{Dapp}$s) and total number of ligand binding sites (B$_{max}$), assuming a single class of binding sites and equal affinities of the iodinated and non iodinated ligand.

Stimulation of Inositol Phosphate Production. COS-7 cells transfected as above with P 1R-WT were treated with serum-free, inositol-free DMEM containing 0.1% bovine serum albumin and [$^3$H]myo-inositol (NEN, Boston, Mass.) (2 µCi/ mL) for 16 h prior to assay. At the time of the assay, the cells were rinsed with binding buffer containing LiCl (30 mM) and treated with the same buffer with or without a PTH analog. The cells were then incubated at 37° C. for 40 min, after which the buffer was removed and replaced by 0.5 mL of ice cold 5% trichloroacetic acid solution. After 3 h on ice, the lysate was collected and extracted twice with ethyl ether. The lysate was then applied to an ion exchange column (0.5 mL resin bed) and the total inositol phosphates were eluted as described previously (Berridge, M. J., et al., *Biochem. J.* 212:473-482 (1983)), and counted in liquid scintillation cocktail.

Inhibition of Chondrocyte Differentiation in Embryonic Mouse Metatarsals. Metatarsals from embryonic day (E) 15.5 mouse embryos were excised and cultured in a 37° C. humidified incubator (5% $CO_2$) in serum-free αMEM media in 24 well plates. Sixteen hours later, a PTH analog or vehicle was added, and the samples were incubated for an additional 48 h in 37° C. with peptide or vehicle added again at the 24 h time point. At the end of the 64 h incubation period, the samples were fixed with 10% formalin/phosphate-buffered saline, then directly visualized on a dissecting microscope using white light. Sections were processed for in-situ hybridization analysis using $^{35}$S-labeled riboprobes specific for collagen type X mRNA, a developmental marker gene expressed only in hypertrophic chrondrocytes of the growth plate.

Circular Dichroism. Circular Dichroism spectra were recorded on a Jasco model 710 spectropolarimeter; peptides were analyzed at a concentration of 20 μM in 50 mM sodium phosphate buffer pH 7.4, or the same buffer containing 2,2, 2-trifluoroethanol at 20% (v/v). Spectroscopic scans were performed at 20° C. and at wavelengths between 185 and 255 nM, with data recored at each 1 nM interval. The spectral bandwidth was 1.5 nM and 8 scans were accumulated and averaged for each sample. At each wavelength, the mean residue elipticity [θ×100/l×C×n); where θ is the raw elipticity value (in dimensions of millidegree), 1 is the sample path length, C=is the molar peptide concentration, and n is the number of residues in the peptide (Bowen, W. P., and Jerman, J. C., *Trends in Pharmacol. Sci.* 16: 413-417 (1995)). The helical content of each peptide was estimated by dividing [θ] observed at 222 nM for that peptide by −28,100, which is the reported $[θ]_{222}$obs for a model helical decapeptide (Bowen, W. P., and Jerman, J. C., *Trends in Pharmacol. Sci.* 16: 413-417 (1995)).

Data Calculation. Calculations were performed using Microsoft® Excel. Nonlinear regression analyses of binding and cAMP dose-response data were performed using the four-parameter equation: $y_p$=Min+[(Max−Min)/(1+($IC_{50}$/x)$^{slope}$)]. The Excel Solver function was utilized for parameter optimization, as described previously (Carter, P. H., et al., *Endocrinology* 140: 4972-4981 (1999); Bowen, W. P., and Jerman, J. C., *Trends in Pharmacol. Sci.* 16: 413-417 (1995)). Differences between paired data sets were statistically evaluated using a one-tailed Student's t-test, assuming unequal variances for the two sets.

Example 2

P1R Binding Affinity of Analogs Containing α,α-Disubstituted Amino Acids

The effects of introducing α,α-disubstituted amino acids distinct from Aib at positions 1 and/or 3 of [M]PTH(1-14) (M=$Ala^{1,3,12}$, $Gln^{10}$, $Har^{11}$,$Trp^{14}$) (SEQ. ID. NO. 13) were analyzed. Six amino acids were chosen: α-Amino-isobutyric acid (Aib), α,α-diethylglycine (Deg); 1-aminocyclopropane-1-carboxylic acid ($Ac_3c$); 1-amino-cyclobutane-carboxylic acid ($Ac_4c$), 1-aminocyclopentane-1-carboxylic acid ($Ac_5c$), and 1-amino-cyclohexane-carboxylic acid ($Ac_6c$) (some of which are shown in FIG. 1).

In competition binding assays performed in an LLC-PK1-derived cell line (B28) that stably expresses the hPTH receptor using $^{125}$I-[$Aib^{1,3}$,$Nle^8$,$Gln^{10}$,$Har^{11}$,$Ala^{12}$,$Trp^{14}$, $Arg^{19}$, $Tyr^{21}$]rPTH(1-21) (SEQ. ID. NO. 36) tracer, the affinities of the $Deg^3$- and $Ac_5c^3$-containing analog were comparable to that of [M]PTH(1-14)($IC_{50}$s~3 μM). The affinity of $Ac_3c^3$-containing analog was 14-fold lower than that of [M]PTH(1-14), and the affinities of the Deg-, $Ac_3c$- and $Ac_5c$-substituted peptides were 3-50 fold higher than that of [M]PTH(1-14) ($C_{50}$=0.6 μM).

The analog [$Ac_5c^1$,$Aib^3$,M]PTH(1-14) (SEQ. ID. NO. 15) exhibited one of the highest binding affinities ($IC_{50}$=100 nM) and one of the highest cAMP potencies {$EC_{50}$=0.9 nM, compared to 200 nM for [M]PTH(1-14)} of any PTH(1-14) analogs studied to date. The $Ac_5c^1$ modification improved affinity 50-fold relative to the parent [M]PTH(1-14) analog {[$Ala^{1,3,12}$,$Gln^{10}$,$Har^{11}$, $Trp^{14}$]humanPTH(1-14)-$NH_2$} (SEQ. ID. NO. 13), and it improved cAMP potency ~35 fold. A cyclopentane ring at position −1 therefore enables a more favorable interaction with the P1R than do the two $C^α$-methyl of Aib. That each of these structurally distinct amino acids at position 1 improves affinity/potency suggests that their enhancing effects are not due to their specific side chain topologies, but rather to their effects on backbone conformation, that is stabilization of α-helix structure. $Deg^3$ substitution showed marginal improvement of affinity by around 1.5 fold, but markedly diminished signaling potency by ~40 fold.

Example 3

$Ac_5c$ Peptide Agonist Activity

The peptide [$Ac_5C^1$, $Aib^3$, M]PTH(1-14)(SEQ. ID. NO. 15) was 2-fold more potent than [$Aib^{1,3}$,M]PTH(1-14) (SEQ. ID. NO. 3) for inhibiting $^{125}$I-[$Aib^{1,3}$,$Nle^8$,$Gln^{10}$,$Har^{11}$, $Ala^{12}$,$Trp^{14}$, $Arg^{19}$,$Tyr^{21}$]rPTH(1-21) (SEQ. ID. NO. 36) binding to B28 cells, and for stimulating adenylyl cyclase, as well as for stimulating phospholipase C (FIG. 2). This peptide is thus one of the most potent PTH(1-14) analog identified so far. Combining $Deg^1$ and $Deg^3$ yielded a peptide that bound with adequate affinity (FIG. 1A) but was a true partial agonist for cAMP formation (FIG. 1B).

The peptide [$Ac_5c^1$, $Aib^3$, $Gln^{10}$]PTH(1-10) (SEQ. ID. NO. 22) was a fall cAMP agonist, albeit with micromolar potency at $10^{-4}$M, [$Ac_5c^1$, $Aib^3$]PTH (1-9) (SEQ. ID. NO. 31) exhibited clear agonist activity making it the shortest PTH analog peptide with reliable cAMP agonist activity.

Example 4

$Ac_5c$ Peptide Antagonist Activity

Ligands that function as antagonists can be useful for treating hyperparathyroidism. Analogs of [$Ac_5c^1$, $Aib^3$, M]PTH (1-14)(parent) (SEQ. ID. NO. 15) containing N-terminal modifications predicted to dissociate signaling and binding affinity (e.g. desamino-1, Trp-2, Bpa-2, Arg-2, Deg-1,3). Most of the substitutions moderately reduced P1R binding affinity and strongly reduced cAMP-stimulating potency.

The $Trp^2$ analog [$Ac_5c^1$,$Trp^2$,$Aib^3$, M]PTH(1-14) (SEQ. ID. NO. 23) at $10^{-5}$ M inhibits the agonist activity of [$Aib^{1,3}$,M]PTH(1-14) (SEQ. ID. NO. 3) at $10^{-9}$ M by 50%.

Example 5

Single Substitutions at Positions 1 and 3 in PTH (1-14)

Single substitutions of di-alkyl amino acids were introduced at positions 1 and 3 in the parent scaffold peptide

[Ala$^{1,3,12}$,Gln$^{10}$,Har$^{11}$,Trp$^{14}$]PTH(1-14)NH$_2$ (SEQ. ID. NO. 13). Schematic structures of the amino acids utilized at positions 1 and 3 in these studies are shown in FIG. 1, and the peptide sequences are presented in Table 1. The parent peptide [Ala$^{1,3,12}$,Gln$^{10}$,Har$^{11}$,Trp$^{14}$]PTH(1-14)NH$_2$ (SEQ. ID. NO. 13), which contains alanine at positions 1 and 3, stimulated cAMP accumulation in HKRK-B28 cells with a potency (EC$_{50}$) value of 220±80 nM, and it inhibited the binding of $^{125}$I-[Aib$^{1,3}$,Nle$^8$,Gln$^{10}$,Har$^{11}$,Ala$^{12}$,Trp$^{14}$, Arg$^{19}$,Tyr$^{21}$] rPTH(1-21) (SEQ. ID. NO. 36) tracer radioligand to these cells with an apparent affinity (IC$_{50}$) value of 27±3 µM. Relative to the parent analog, the analogs substituted at position 1 were ~two-fold (Ac$_3$c, P=0.1), 11-fold (Deg, P=0.02) or 61-fold (Ac5c, P=0.02) more potent for stimulating cAMP accumulation, and these increases in potency were accompanied by commensurate effects on apparent binding affinity. At position 3, substitution with either cycloalkane amino acid, Ac$_3$c or Ac$_5$c, increased cAMP-stimulating potency modestly (<two-fold), whereas substitution with the linear amino acid, Deg, diminished potency approximately 10-fold; Ac$_5$c-3 and Deg-3 had little or no effect on binding affinity, whereas Ac$_3$c-3 reduced affinity approximately 10-fold.

Example 6

Combined Substitutions at Positions 1 and 3 is PTH(1-14) Analogs

Di-alkyl amino acids were introduced at both positions 1 and 3 of the parent scaffold peptide [Ala$^{1,3,12}$,Gln$^{10}$,Har$^{11}$,Trp$^{14}$]PTH(1-14)NH$_2$ (SEQ. ID. NO. 13). Introducing Ac$_3$c at positions 1 and 3 yielded the analog [Ac$_3$c$^{1,3}$,Gln$^{10}$,Har$^{11}$,Ala$^{12}$,Trp$^{14}$]PTH(1-14)NH$_2$ (SEQ. ID. NO. 28), which was comparable to the parent peptide in terms of binding affinity and signaling potency. Introducing Ac$_5$c at these positions yielded the analog [Ac$_5$c$^{1,3}$,Gln$^{10}$,Har$^{11}$,Ala$^{12}$,Trp$^{14}$]PTH(1-14)NH$_2$ (SEQ. ID. NO. 29), which bound to the P1R with 20-fold higher affinity than did the parent peptide (P=0.001) and was 30-fold more potent for cAMP signaling (P=0.02; Table 2). Combining the Deg substitutions at positions 1 and 3 yielded [Deg$^{1,3}$,Gln$^{10}$,Har$^{11}$,Ala$^{12}$,Trp$^{14}$]pTH(1-14)NH$_2$ (SEQ. ID. NO. 27), which bound to the P1R with an affinity 50-fold higher than that of the parent (P=0.001) but elicited only a partial agonist response which attained a maximum that was only 45% of that attained by the parent peptide.

Example 7

PTH(1-9) and PTH(1-10) Analogs

Minimum-length active analogs were developed to be used to functionally probe the PTH.PTH receptor interaction mechanism. Native N-terminal PTH analogs that are shorter than PTH(1-14) are inactive in cell-based assays, measurable cAMP responses can be detected in P1R-transfected cells for the analog [Aib$^{1,3}$,Gln$^{10}$]PTH(1-10)NH$_2$(SEQ. ID. NO. 35). [Ac$_5$c$^1$,Aib$^3$,Gln$^{10}$]PTH(1-10)NH$_2$(SEQ. ID. NO. 22) and [Ac$_5$c$^1$,Aib$^3$]PTH(1-9)NH$_2$ (SEQ. ID. NO. 31) were prepared and their activity was assessed in HKRK-B28 cells. When tested at concentrations as high as 1×10$^{-4}$M, neither peptide inhibited the binding of P(1-21) tracer radioligand. Each analog induced a clear cAMP response in these cells. From dose-response analysis of [Ac$_5$c$^1$,Aib$^3$,Gln$^{10}$]PTH(1-10)NH$_2$ (SEQ. ID. NO. 22), EC$_{50}$ value was estimated at approximately 3 µM. The PTH(1-19) analog was assayed at a single high concentration (1×10$^{-4}$M) and found to induce a six-fold increase in cAMP levels, relative to the basal levels (P=0.001); at the same concentrations, [Aib$^{1,3}$,Gln$^{10}$]PTH(1-10)NH$_2$ (SEQ. ID. NO. 35) induced a two-fold increase in cAMP accumulation (P=0.52) and native PTH(1-9) (SEQ. ID. NO. 33) was inactive.

Example 8

Analog Activity in P1R-delNT Cells

Agonist activities of selected analogs in cells expressing P1R-delNt were examined. This PTH-1 receptor construct lacks most of the N domain, but nevertheless mediates full agonist responses to N-terminally modified PTH analogs, and thus enables the relative roles of the receptor's N and J domains to the ligand interaction process to be evaluated. The clonal cell line LdelNT-2 was used, which was derived from LLC-PK, cells by stable transfection with a plasmid encoding the human P1R-delNt construct. In these cells, [Ac$_5$c$^1$, Aib$^3$, Gln$^{10}$,Har$^{11}$,Ala$^{12}$,Trp$^{14}$]PTH(1-14)NH$_2$ (SEQ. ID. NO. 15) induced a 70-fold increase in cAMP accumulation with high potency (EC$_{50}$=6.4±2.3 nM); [Ac$_5$c$^1$,Aib$^3$,Gln$^{10}$]PTH(1-10)NH$_2$ (SEQ. ID. NO. 22) exhibited weaker potency (EC$_{50}$~40 µM) and [Deg$^{1,3}$,Gln$^{10}$,Har$^{11}$,Ala$^{12}$,Trp$^{14}$]PTH(1-14)NH$_2$ (SEQ. ID. NO. 27) exhibited partial agonist behavior (E$_{max}$=23-fold over basal; EC$_{50}$=1.4±0.5 µM).

TABLE 1

PTH Peptide Sequences

| | 1      5      10   14 |
|---|---|
| PTH(1-14)NH$_2$ | Ser-V-Ser-E-I-Q-L-M-H-N-Leu-G-K-H(SEQ. ID. NO. 26) |
| [M]PTH(1-14) (Parent) | A-V-A-E-I-Q-L-M-H-Q-Har-A-K-W (SEQ. ID. NO. 13) |
| [Deg$^1$,M]PTH(1-14) | Deg-V-A-E-I-Q-L-M-H-Q-Har-A-K-W(SEQ. ID. NO. 24) |
| [Ac$_3$c$^1$,M]PTH(1-14) | Ac$_3$c-V-A-E-I-Q-L-M-H-Q-Har-A-K-W(SEQ. ID. NO. 25) |
| [Ac$_5$c$^1$,M]PTH(1-14) | Ac$_5$c-V-A-E-I-Q-L-M-H-Q-Har-A-K-W(SEQ. ID. NO. 4) |
| [Deg$^{1,3}$,M]PTH(1-14) | Deg-V-Deg-E-I-Q-L-M-H-Q-Har-A-K-W(SEQ. ID. NO. 27) |
| [Ac$_3$c$^{1,3}$,M]PTH(1-14) | Ac$_3$c-V-Ac$_3$c-E-I-Q-L-M-H-Q-Har-A-K-W (SEQ. ID. NO. 28) |
| [Ac$_5$c$^{1,3}$,M]PTH(1-14) | Ac$_5$c-V-Ac$_5$c-E-I-Q-L-M-H-Q-Har-A-K-W (SEQ. ID. NO. 29) |
| [Aib$^{1,3}$,M]PTH(1-14) | Aib-V-Aib-E-I-Q-L-M-H-Q-Har-A-K-W ( SEQ.ID. NO. 3) |
| [Ac$_5$c$^1$,Aib$^3$,M]PTH(1-14) | Ac$_5$c-V-Aib-E-I-Q-L-M-H-Q-Har-A-K-W (SEQ ID. NO. 15) |
| [Ac$_5$c$^1$,Aib$^3$,M]PTH(1-10) | Ac$_5$c-V-Aib-E-I-Q-L-M-H-Q (SEQ. ID. NO. 22) |

TABLE 1-continued

PTH Peptide Sequences

| | |
|---|---|
| [Ac$_5$c$^1$,Aib$^3$,M]PTH(1-9) | Ac$_5$c-V-Aib-E-I-Q-L-M-H (SEQ. ID. NO. 31) |
| [Ac$_4$c$^1$, Aib$^3$,M]PTH(1-14) | Ac$_4$c-V-Aib-E-I-Q-L-M-H-Q-Har-A-K-W (SEQ. ID. NO. 7) |
| [Ac$_6$c$^1$, Aib$^3$,M]PTH(1-14) | Ac$_6$c-V-Aib-E-I-Q-L-M-H-Q-Har-A-K-W (SEQ. ID. NO. 8) |
| [Ac$_5$c$^1$, Ac$_4$c$^3$,M]PTH(1-14) | Ac$_5$c-V-Ac$_4$c-E-I-Q-L-M-H-Q-Har-A-K-W (SEQ. ID. NO. 9) |
| [Ac$_5$c$^1$, Ac$_6$c$^3$,M]PTH(1-14) | Ac$_5$c-V-Ac$_6$c-E-I-Q-L-M-H-Q-Har-A-K-W (SEQ. ID. NO. 10) |
| [Ac$_4$c$^1$, Ac$_4$c$^3$,M]PTH(1-14) | Ac$_4$c-V-Ac$_4$c-E-I-Q-L-M-H-Q-Har-A-K-W (SEQ. ID. NO. 11) |
| [Ac$_6$c$^1$, Ac$_3$c$^3$,M]PTH(1-14) | Ac$_6$c-V-Ac$_6$c-E-I-Q-L-M-H-Q-Har-A-K-W (SEQ. ID. NO. 12) |
| Tracer Radioligands: | Aib-V-Aib-E-I-Q-L-Nle-H-Q-Har-A-K-W-L-A-S-V-R-R-Y* |
| $^{125}$I-[M*]PTH(1-21) | (SEQ. ID. NO. 36) |

*indicates the iodinated tyrosine

Having now fully described the present invention in some detail by way of illustration and example for purposes of clarity of understanding, it will be obvious to one of ordinary skill in the art that the same can be performed by modifying or changing the invention with a wide and equivalent range of conditions, formulations and other parameters thereof, and that such modifications or changes are intended to be encompassed within the scope of the appended claims.

All publications, patents and patent applications mentioned herein above are herein incorporated in their entirety and by reference to the same extent as if each individual publication, patent or patent application was specifically and individually indicated to be incorporated by reference.

What is claimed is:

1. A biologically active peptide comprising the formula:

$$X_{01}ValX_{02}GluIleGlnLeuMetHisX_{03}X_{04}X_{05}X_{06}X_{07};$$ (SEQ. ID. NO. 1)

a fragment thereof consisting of amino acids 1-9, 1-10, 1-11, 1-12, or 1-13;
a pharmaceutically acceptable salt thereof; or
(d) an N- or C-derivative thereof;
wherein:
$X_{01}$ is an α-helix-stabilizing residue, Gly, Ser or Ala;
$X_{02}$ is an α-helix-stabilizing residue, Ala or Ser;
$X_{03}$ is Ala, Gln or Asn;
$X_{04}$ is Arg, Har or Leu;
$X_{05}$ is an α-helix stabilizing residue, Ala or Gly;
$X_{06}$ is an α-helix stabilizing residue or Lys;
$X_{07}$ is an α-helix stabilizing residue, Trp or His;
wherein at least one of $X_{01}$, $X_{02}$, $X_{05}$, $X_{06}$ or $X_{07}$ is an α-helix stabilizing residue, and wherein at least one of said α-helix stabilizing residues is $Ac_4c$ or $Ac_6c$.

2. The peptide of claim 1, wherein said peptide comprises:

$$Ac_4cValAibGluIleGlnLeuMetHisGlnHarAlaLysTrp;$$ (SEQ. ID. NO. 7)

a fragment thereof consisting of amino acids 1-9, 1-10, 1-11, 1-12 or 1-13;

a pharmaceutically acceptable thereof; or
an N- or C-derivative thereof.

3. The peptide of claim 1, wherein said peptide comprises:

Ac$_6$cValAibGluIleGlnLeuMetHisGlnHarAlaLysTrp; (SEQ. ID. NO. 8)

a fragment thereof consisting of amino acids 1-9, 1-10, 1-11, 1-12 or 1-13;
a pharmaceutically acceptable salt thereof; or
an N- or C-derivative thereof.

4. The peptide of claim 1, wherein said peptide comprises:

Ac$_5$cValAc$_4$cGluIleGlnLeuMetHisGlnHarAlaLysTrp; (SEQ. ID. NO. 9)

a fragment thereof consisting of amino acids 1-9, 1-10, 1-11, 1-12 or 1-13;
a pharmaceutically acceptable salt thereof; or
an N- or C-derivative thereof.

5. The peptide of claim 1, wherein said peptide comprises:

Ac$_5$cValAc$_6$cGluIleGlnLeuMetHisGlnHarAlaLysTrp; (SEQ. ID. NO. 10)

a fragment thereof consisting of amino acids 1-9, 1-10, 1-11, 1-12 or 1-13;
a pharmaceutically acceptable salt thereof; or
an N- or C-derivative thereof.

6. The peptide of claim 1, wherein said peptide comprises:

Ac$_4$cValAc$_4$cGluIleGlnLeuMetHisGlnHarAlaLysTrp; (SEQ. ID. NO. 11)

a fragment thereof consisting of amino acids 1-9, 1-10, 1-11, 1-12 or 1-13;
a pharmaceutically acceptable salt thereof; or
an N- or C-derivative thereof.

7. The peptide of claim 1, wherein said peptide comprises:

Ac$_6$cValAc$_6$cGluIleGlnLeuMetHisGlnHarAlaLysTrp; (SEQ. ID. NO. 12)

a fragment thereof consisting of amino acids 1-9, 1-10, 1-11, 1-12 or 1-13;
a pharmaceutically acceptable salt thereof; or
an N- or C-derivative thereof.

8. The peptide of claim 1, wherein said peptide is labeled with a label selected from the group consisting of a fluorescent label, a chemiluminescent label, a bioluminescent label and a radioactive label.

9. The peptide of claim 1, wherein said peptide is labeled with $^{125}$I.

10. The peptide of claim 1, wherein said peptide is labeled, with $^{99m}$Tc.

11. A pharmaceutical composition comprising the biologically active peptide of claim 1, and a pharmaceutically acceptable carrier.

12. A method for treating a mammalian subject having a condition characterized by a decrease in bone mass, said method comprising administering to said subject in need thereof an effective bone-mass increasing amount of the biologically active peptide of claim 1.

13. A method for treating a mammalian subject having a condition characterized by a decrease in bone mass, said method comprising administering to said subject in need thereof an effective bone mass-increasing amount of a composition comprising the biologically active peptide of claim 1 and a pharmaceutically acceptable carrier.

14. The method of claim 12, wherein said condition to be treated is osteoporosis.

15. The method of claim 12, wherein said osteoporosis is postmenopausal osteoporosis or old-age osteoporosis.

16. The method of claim 12, wherein said effective amount of said peptide for increasing bone mass is from about 0.01 µg/kg/day to about 1.0 µg/kg/day.

17. The method of claim 12, wherein the method of administration is parenteral.

18. The method of claim 12, wherein the method of administration is subcutaneous.

19. The method of claim 12, wherein the method of administration is nasal insufflation.

20. The method of claim 12, wherein the method of administration is oral.

21. The biologically active peptide of claim 1, wherein said peptide is synthesized by solid phase synthesis.

22. The biologically active peptide of claim 1, wherein said peptide is synthesized by liquid phase synthesis.

23. The biologically active peptide of claim 1, wherein said peptide is protected by FMOC.

24. The peptide of claim 2, wherein said peptide consists of the amino acid sequence Ac$_4$cValAibGluIleGlnLeuMetHisGlnHarAlaLysTrp (SEQ. ID. NO. 7), or a pharmaceutically acceptable salt thereof.

25. The peptide of claim 3, wherein said peptide consists of the amino acid sequence Ac$_6$cValAibGluIleGlnLeuMetHisGlnHarAlaLysTrp (SEQ. ID. NO. 8), or a pharmaceutically acceptable salt thereof.

26. The peptide of claim 4, wherein said peptide consists of the amino acid sequence Ac$_5$cValAc$_4$cGluIleGlnLeuMetHisGlnHarAlaLysTrp (SEQ. ID. NO. 9), or a pharmaceutically acceptable salt thereof.

27. The peptide of claim 5, wherein said peptide consists of the amino acid sequence Ac$_5$cValAc$_6$cGluIleGlnLeuMetHisGlnHarAlaLysTrp (SEQ. ID. NO. 10), or a pharmaceutically acceptable salt thereof.

28. The peptide of claim 6, wherein said peptide consists of the amino acid sequence Ac$_4$cValAc$_4$cGluIleGlnLeuMetHisGlnHarAlaLysTrp (SEQ. ID. NO. 11), or a pharmaceutically acceptable salt thereof.

29. The peptide of claim 7, wherein said peptide consists of the amino acid sequence Ac$_6$cValAc$_6$cGluIleGlnLeuMetHisGlnHarAlaLysTrp (SEQ. ID. NO. 12), or a pharmaceutically acceptable salt thereof.

\* \* \* \* \*

UNITED STATES PATENT AND TRADEMARK OFFICE
CERTIFICATE OF CORRECTION

| | |
|---|---|
| PATENT NO. | : 7,795,220 B2 |
| APPLICATION NO. | : 10/549592 |
| DATED | : September 14, 2010 |
| INVENTOR(S) | : Gardella et al. |

It is certified that error appears in the above-identified patent and that said Letters Patent is hereby corrected as shown below:

Title Page 3, under Item (56) OTHER PUBLICATIONS, in Shimizu et al. (2001),
Replace "α-Aminosobutyric Acid" with --α-Aminoisobutyric Acid--.

Title Page 5, under Item (56) OTHER PUBLICATIONS, in Barden et al. (1989),
replace "Hormon-Related" with --Hormone-Related--.

Title Page 7, under Item (56) OTHER PUBLICATIONS, in Holtmann et al. (1996),
replace "Molecular Basis and Species Specificity of High
Affinity Binding of Vasoactive Intestinal Polypeptide by the
Rat Secretin Receptor. Effec of Receptor-G-Protein
Interaction on the Ligand Binding Mechanism and Receptor
Conformation" with --Molecular Basis and Species Specificity
of High Affinity Binding of Vasoactive Intestinal
Polypeptide by the Rat Secretin Receptor--.

Title Page 8, under Item (56) OTHER PUBLICATIONS, in Shimizu et al. (2005),
replace "(Pth)" with --(PTH)--.

Title Page 9, under Item (56) OTHER PUBLICATIONS, in Sunyaev et al., replace
"Structrual" with --Structural--;

Under item (56) OTHER PUBLICATIONS, in Takasu et al. (1998), replace
"Receptos" with --Receptors--.

Column 2, Line 54, replace "phospolipase" with --phospholipase--.

Column 3, Lines 18-19, replace "Shimizu, M. et al., *J. Biol.*
*Chem.* 276:490003-49012 (2001)" with --Shimizu, N. et al., *J.*
*Biol. Chem.* 276:49003-49012  (2001)--.

Signed and Sealed this
Twenty-eighth Day of February, 2012

David J. Kappos
*Director of the United States Patent and Trademark Office*

Column 10, Line 25, replace "<" with --≤--;

Column 13, Line 63, replace "PIH" with --PTH--.

Column 14, Line 16, replace "hypemephroma" with --hypernephroma--;

Line 61, replace "PTH/PnkrP" with --PTH/PTHrP--.

Column 15, Line 45, replace "opposum" with --opossum--;

Line 49, replace "LLC-PK," with --LLC-$PK_1$--;

Line 59, replace "GLBCO" with --GIBCO--.

Column 17, Line 19, replace "chrondrocytes" with --chondrocytes--;

Line 26, replace "recored" with --recorded--;

Line 29, replace "elipticity [θx100/1xCxn); where θ is the raw elipticity" with --ellipticity θx100/1xCxn); where θ is the raw ellipticity--.

Column 18, Line 7, replace "($C_{50}$=0 . 6μM)" with --($IC_{50}$=0 . 6μM)--;

Line 31, replace "was 2-fold" with --was ~ 2-fold--;

Line 59, replace "by 50%" with --by ~50%--.

Columns 19-20, under TABLE 1, in SEQ. ID. NO. 29, replace "[$Ac_5c^{1,3}$, M] IPTH (1-14)" with --[$Ac_5c^{1,3}$, M] PTH (1-14)-- .

Column 20, Line 7, replace "PTH.PTH" with --PTH•PTH--.

Column 61, Line 1, replace "a pharmaceutically acceptable thereof" with --a pharmaceutically acceptable salt thereof--.